United States Patent [19]

Beck et al.

[11] 4,179,277

[45] Dec. 18, 1979

[54] 4,5-DICHLOROIMIDAZOLE-2-CARBOXYLIC ACID DERIVATIVES

[75] Inventors: Gunther Beck, Leverkusen; Klaus Sasse, Schildgen; Helmut Heitzer; Ludwig Eue, both of Leverkusen; Robert R. Schmidt, Cologne; Hans Scheinpflug, Leverkusen; Ingeborg Hammann; Wilhelm Brandes, both of Cologne, all of Fed. Rep. of Germany

[73] Assignee: Bayer Aktiengesellschaft, Leverkusen, Fed. Rep. of Germany

[21] Appl. No.: 770,260

[22] Filed: Feb. 18, 1977

[30] Foreign Application Priority Data

Mar. 12, 1976 [DE] Fed. Rep. of Germany ....... 2610527
Jun. 2, 1976 [DE] Fed. Rep. of Germany ....... 2624759
Jul. 29, 1976 [DE] Fed. Rep. of Germany ....... 2634053

[51] Int. Cl.² ............... A01N 9/22; C07D 233/66
[52] U.S. Cl. ............................ 71/92; 548/337; 424/273 R
[58] Field of Search ................ 548/337; 260/293.7; 424/273, 273 R; 71/92

[56] References Cited

U.S. PATENT DOCUMENTS

| | | | |
|---|---|---|---|
| 3,435,050 | 3/1969 | Wasco | 548/337 |
| 3,501,286 | 3/1970 | Draber et al. | 548/337 |
| 3,759,945 | 9/1973 | Rutz | 548/337 |
| 3,772,315 | 11/1973 | Regel et al. | 548/337 |

FOREIGN PATENT DOCUMENTS 1485394 5/1967 France .................... 548/337

*Primary Examiner*—Alan L. Rotman
*Attorney, Agent, or Firm*—Sprung, Felfe, Horn, Lynch & Kramer

[57] ABSTRACT

4,5-Dichloroimidazole-2-carboxylic acid derivatives of the formula

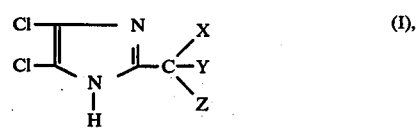

in which the group

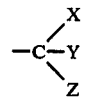

represents a carbon atom which has three bonds to hetero-atoms, and their salts with bases, possess insecticidal, acaricidal, fungicidal, nematicidal and herbicidal properties.

25 Claims, No Drawings

4,5-DICHLOROIMIDAZOLE-2-CARBOXYLIC ACID DERIVATIVES

The present invention relates to and has for its objects the provision of particular new 4,5-dichloroimidazole-2-carboxylic acid derivatives which possess insecticidal, acaricidal, fungicidal, nematicidal and herbicidal properties, active compositions in the form of mixtures of such compounds with solid and liquid dispersible carrier vehicles, and methods for producing such compounds and for using such compounds in a new way especially for combating pests, e.g. plants and animals located where they are not desired, with other and further objects becoming apparent from a study of the within specification and accompanying examples.

It has already been disclosed that derivatives of benzimidazole-2-carboxylic acids, for example benzimidazole-2-carboxylic acid nitrile, possess herbicidal properties (Netherlands Patent Application 7,004,376). However, the action of these compounds is not satisfactory, especially when low concentrations are applied.

The present invention now provides, as new compounds, the 4,5-dichloroimidazole-2-carboxylic acid derivatives of the general formula

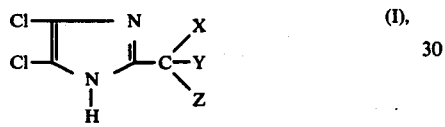

in which the group

represents a carbon atom which has three bonds to hetero-atoms,
and their salts with bases.

The compounds of the present invention have been found to possess a pesticidal action.

The present invention also provides a process for the preparation of a 4,5-dichloroimidazole-2-carboxylic acid derivative of the formula (I), in which (a) 4,5-dichloro-2-dichloromethylene-imidazole, of the formula

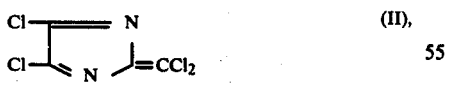

or (b) 4,5-dichloro-2-trichloromethylimidazole, of the formula

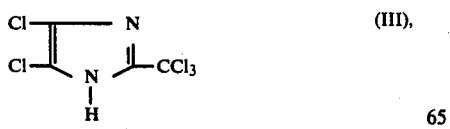

or (c) the dimeric ketene of 4,5-dichloroimidazole-2-carboxylic acid, of the formula

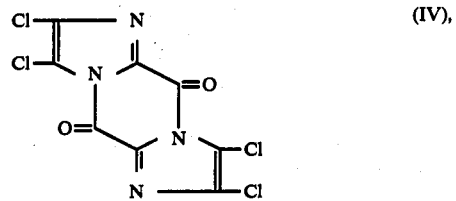

is reacted with a suitable nucleophilic reagent and the reaction product thus formed is optionally subjected to further subsequent reactions.

Preferably, in this reaction, salts are obtained in which the 4,5-dichloroimidazole derivative is present as the anion and the cation is either a metal cation $Me^{n+}{}_{1/n}$, in which n denotes the valency of the metal, or an optionally substituted ammonium cation $NR_4{}^+$
in which R denotes hydrogen or an organic radical, for example alkyl, aryl, cycloalkyl or aralkyl, and 2 or 3 of these radicals can also be linked to one another to form a 5-membered or 6-membered ring.

A preferred class of compounds of the formula (I) are those
in which X, Y and Z, independently of one another, each denote halogen (especially chlorine or fluorine) or one of the following groups:

in which $R^1$ denotes a saturated or unsaturated aliphatic or cycloaliphatic hydrocarbon radical, especially with 1-12 carbon atoms (optionally substituted by $C_{1-4}$-alkoxy, $C_{1-4}$-alkylmercapto or aryl, aryloxy or arylmercapto (in which the aryl group is preferably phenyl or naphthyl and is optionally substituted by halogen, $C_{1-4}$-alkyl, $CF_3$ or $C_{1-4}$-alkoxy), or by $C_{1-4}$-alkoxycarbonyl, aminocarbonyl, a cycloaliphatic radical, especially with 5 or 6 ring carbon atoms, or a heterocyclic radical, especially a 5-membered or 6-membered heterocyclic radical which contains O, S or N), or

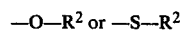

in which $R^2$ denotes aryl, especially phenyl or naphthyl (which aryl group is optionally substituted by $C_{1-4}$-alkyl, $C_{1-4}$-polyfluoroalkyl, especially $CF_3$, halogen, $C_{1-4}$-alkoxy, or aryloxy or arylmercapto (in which the aryl group is preferably phenyl or naphthyl which is optionally substituted by halogen, $C_{1-4}$-alkyl, $CF_3$, $C_{1-4}$-alkoxy, $NO_2$ or $C_{1-4}$-alkylmercapto) or by $C_{1-4}$-alkylmercapto, $C_{1-4}$-alkylsulphonyl, $C_{1-4}$-alkoxycarbonyl, aminocarbonyl, CN, $NO_2$ or dialkylamino, especially with 1–4 carbon atoms per alkyl radical), and the aryl group $R^2$ can also contain a fused cycloaliphatic or heterocyclic ring.

Another preferred class of compounds of the formula (I) are those
in which X and Y conjointly denote oxygen, sulphur or the group

in which $R^3$ denotes hydrogen, OH or $C_{1-12}$-alkyl (which alkyl group is optionally substituted by halogen, OH, $C_{1-4}$-alkoxy or aryloxy, especially phenoxy (which aryloxy group is optionally substituted by $C_{1-4}$-alkyl or halogen, such as chlorine), or by $C_{1-4}$-alkylmercapto, benzylmercapto, COOH, CONH$_2$, CONH—$C_{1-4}$-alkyl, CON($C_{1-4}$-alkyl)$_2$ or CONH-aryl (in which the aryl group is preferably phenyl or naphthyl and is optionally substituted by halogen, $C_{1-4}$-alkyl, especially methyl, trifluoromethyl, $C_{1-4}$-alkoxy or nitro) or by cycloalkyl with 5 or 6 ring carbon atoms (which is optionally substituted by $C_{1-4}$-alkyl), or by a 5-membered or 6-membered heterocyclic structure which contains O, S or N), or denotes $C_{3-8}$-alkenyl (which is optionally substituted by halogen or $C_{1-4}$-alkoxy), $C_{3-12}$-alkynyl (which is optionally substituted by aryl, especially phenyl (which aryl group is optionally substituted by halogen, $C_{1-4}$-alkyl, trifluoromethyl, $C_{1-4}$-alkoxy or nitro) or by cycloalkyl with 5 or 6 ring carbon atoms), cycloalkyl with 4–8 ring carbon atoms (which is optionally substituted by $C_{1-4}$-alkyl or CF$_3$ or contains a fused phenyl ring), aryl (especially phenyl or naphthyl, which may be optionally substituted) or a 5-membered or 6-membered heterocyclic structure which contains, O, S or N, or $R^3$ represents a group O—$R^4$ in which $R^4$ denotes $C_{1-4}$-alkyl, aralkyl (especially benzyl) or a group

in which $R^7$ denotes hydrogen or $C_{1-12}$-alkyl or $C_{2-8}$-alkenyl (which can each be substituted by halogen, especially chlorine, nitro, $C_{1-4}$-alkylmercapto or arylmercapto, especially phenylmercapto (which arylmercapto group is optionally substituted by halogen or $C_{1-4}$-alkyl), or by aryl, especially phenyl (which aryl group is optionally substituted by halogen or $C_{1-4}$-alkyl) or by cycloalkyl with 5 or 6 ring carbon atoms), or $R^7$ denotes $C_{2-8}$-alkynyl, cycloalkyl with 3–6 ring carbon atoms or aryl, especially phenyl or naphthyl (which is optionally substituted by halogen, $C_{1-4}$-alkyl, $C_{1-4}$-alkoxy, CF$_3$ or NO$_2$), or denotes a 5-membered or 6-membered heterocyclic structure, which contains O, S or N, or a group —O—$R^{26}$ or —S—$R^{26}$ in which $R^{26}$ denotes $C_{1-12}$-alkyl, $C_{3-12}$-alkenyl or $C_{3-12}$-alkynyl (which can optionally be substituted by halogen, $C_{1-4}$-alkoxy or phenyl (which is optionally substituted by halogen or $C_{1-4}$-alkyl) or by cycloalkyl, especially cyclohexyl, or by a 5-membered or 6-membered heterocyclic structure which contains O, S or N, especially furyl, thienyl or pyridyl), or denotes $C_{3-6}$-cycloalkyl or aryl, preferably phenyl or naphthyl (which is optionally substituted by halogen, $C_{1-4}$-alkyl, $C_{1-4}$-alkoxy or nitro), or $R^7$ denotes a group

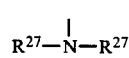

in which the $R^{27}$ moieties can be identical or different and each denote hydrogen or $C_{1-12}$-alkyl or $C_{3-8}$-alkenyl (which can be substituted by halogen, $C_{1-4}$-alkoxy or aryl, especially phenyl, which aryl group is optionally substituted by halogen or $C_{1-4}$-alkyl), or denote cycloalkyl with 5 or 6 ring carbon atoms or aryl, especially phenyl (which aryl group is optionally substituted by halogen, $C_{1-4}$-alkyl, $C_{1-4}$-alkoxy, $C_{1-4}$-alkyl-mercapto, CF$_3$ or NO$_2$).

Alternatively, $R^3$ may represent the group

in which $R^5$ and $R^6$ can be identical or different and each denote hydrogen, $C_{1-4}$-alkyl (which is optionally substituted by aryl, especially phenyl, which aryl substituent is optionally substituted by halogen or $C_{1-4}$-alkyl, especially methyl), aryl, especially phenyl (which aryl group is optionally substituted by halogen, NO$_2$, $C_{1-4}$-alkyl, especially methyl, $C_{1-4}$-alkoxy or CF$_3$) or the group

in which $R^7$ has the above-mentioned meaning, or $R^5$ and/or $R^6$ may denote the group —SO$_2$—$R^8$ in which $R^8$ denotes $C_{1-12}$-alkyl (which is optionally substituted by halogen, especially chlorine or fluorine) or aryl, especially phenyl (which aryl group is optionally substituted by halogen, especially chlorine, $C_{1-4}$-alkyl, $C_{1-4}$-alkoxy, CF$_3$ or NO$_2$) or denotes a secondary amino group, or $R^5$ or $R^6$ conjointly can denote the group

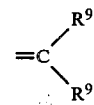

in which the $R^9$ moieties are identical or different and each denote $C_{1-12}$-alkyl (which is optionally substituted by OH, $C_{1-4}$-alkoxy, COOH or COO($C_{1-4}$-alkyl)), cycloalkyl with 5 or 6 ring carbon atoms, aralkyl with 1–4 carbon atoms in the alkyl part and, as the aryl part, preferably phenyl or naphthyl (which may be optionally substituted by halogen, NO$_2$, $C_{1-4}$-alkyl or $C_{1-4}$-alkoxy), aryl, especially phenyl or naphthyl (which aryl group is optionally substituted by OH, halogen, NO$_2$, $C_{1-4}$-alkyl, $C_{1-4}$-alkoxy, $C_{1-4}$-alkylmercapto or CF$_3$) or a 5-membered or 6-membered heterocyclic structure which contains O, S or N, or the two radicals $R^9$ can form, conjointly with the adjacent carbon atom, a carbocyclic or heterocyclic ring, or one of the radicals $R^9$ can also denote hydrogen, or $R^5$ and $R^6$ can form, with the adjacent N atom, a 5-membered or 6-membered heterocyclic structure which can contain at least one further hetero-atom, such as O, N or S.

Another preferred class of compounds of the formula (I) are those in which Z denotes a group —O—$R^{10}$ or —S—$R^{10}$ in which $R^{10}$ denotes hydrogen, a salt-forming cation (in which case the bond between O or S and $R^{10}$ does not represent a covalent bond, but indicates the formation of a salt), especially a metal cation or an ammonium cation NR$_4^{30}$ in which R has the above-mentioned meaning, or R[10] denotes alkyl or alkenyl, especially $C_{1-18}$-alkyl and $C_{3-12}$-alkenyl [either of which is optionally substituted by halogen, especially chlorine, fluorine or bromine, OH or acyloxy, in which the acyl group is of an aliphatic, cycloaliphatic, araliphatic or aromatic carboxylic acid or is the radical of a heterocyclic carboxylic acid, especially the radical

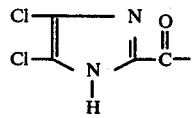

or by alkoxy, especially with 1–4 carbon atoms, alkoxyalkoxy with up to 4 carbon atoms in each alkoxy moiety, aryloxy, especially phenoxy or naphthoxy (which arloxy group is optionally substituted by halogen, $C_{1-4}$-alkyl, $CF_3$ or $NO_2$), alkylmercapto, especially with 1–4 carbon atoms (which is optionally substituted by aryl, especially phenyl which itself is optionally substituted by $C_{1-4}$-alkyl or halogen), or arylmercapto, arylsulphinyl or arylsulphonyl (wherein aryl is preferably phenyl or napthyl, each optionally substituted by $C_{1-4}$-alkyl or halogen), or alkulsulphonyl, especially with 1–4 carbon atoms, acylamino or diacylamino (in which the acyl radical is of an aliphatic, cycloaliphatic, araliphatic, aromatic or heterocyclic carboxylic acid or is the radical of a carbonic acid or thiocarbonic acid derivative), or CN, a carboxylic acid ester radical, cycloalkyl, especially with 5–6 ring carbon atoms, or aryl, especially phenyl (which is optionally substituted by halogen, $C_{1-4}$-alkyl or $C_{1-4}$-alkoxy) or a 5-membered or 6-membered heterocyclic structure which contains O, S or N], or R[10] represents alkynyl, especially with 3–12 atoms, cycloalkyl, especially with 3–6 ring carbon atoms (which cycloalkyl group is optionally substituted by halogen, $C_{1-4}$-alkyl or $C_{1-4}$-alkoxy or contains a fused ring) or aryl, especially phenyl or naphthyl [which aryl group is optionally substituted by $C_{1-4}$-alkyl, polyhalogeno($C_{1-4}$-alkyl), especially $CF_3$, halogen, $C_{1-4}$-alkoxy, aryloxy or arylmercapto (especially phenoxy or phenylmercapto which are optionally substituted by halogen, $C_{1-4}$-alkyl, $CF_3$, $C_{1-4}$-alkoxy or $NO_2$), $C_{1-4}$-alkylmercapto, $C_{1-4}$-alkylsulphonyl, $C_{1-4}$-alkoxycarbonyl, aminocarbonyl, CN, $NO_2$ or monoalkylamino or dialkylamino, especially with 1–4 carbon atoms per alkyl part, or contains fused cycloaliphatic or heterocyclic radicals].

Alternatively, Z may represent a group

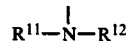

in which R[11] and R[12] are identical or different and each denote hydrogen or alkyl, especially with 1–12 carbon atoms, or alkenyl, especially with 3–8 carbon atoms [which are optionally substituted by halogen, especially chlorine, fluorine or bromine, OH, alkoxy, especially $C_{1-4}$-alkoxy, or aryloxy, especially phenoxy (which aryloxy group is optionally substituted by $C_{1-4}$-alkyl, halogen or $C_{1-4}$-alkoxy) or by acyloxy in which the acyl radical is of an aliphatic, cycloaliphatic, araliphatic or aromatic carboxylic acid or is the radical of a heterocyclic carboxylic acid, especially the radical

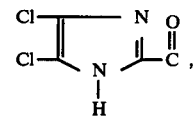

or by alkylmercapto, especially $C_{1-4}$-alkylmercapto (which alkylmercapto group is optionally substituted by aryl, especially phenyl) or by arylmercapto, especially phenylmercapto (which arylmercapto is optionally substituted by halogen or $C_{1-4}$-alkyl), or by CN, COOH, COOR, $CONH_2$, $CONH(C_{1-4}$-alkyl), $CON(C_{1-4}$-alkyl)$_2$ or CONH-aryl in which aryl preferably denotes phenyl or naphthyl (which are optionally substituted by halogen, $C_{1-4}$-alkyl, $CF_3$, $C_{1-4}$-alkoxy or $NO_2$), or by cycloalkyl, especially with 5–12 ring carbon atoms, or by a 5-membered or 6-membered heterocyclic structure which contains O, S or N, or by a group of the formula

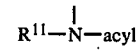

in which R[11] has the above-mentioned meaning and acyl denotes the radical of an aliphatic, cycloaliphatic, araliphatic or aromatic carboxylic acid or the radical of a heterocyclic carboxylic acid, especially the radical

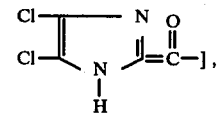

or R[11] and R[12] denote alkynyl, especially with 3–12 carbon atoms (which is optionally substituted by optionally substituted aryl, especially phenyl, or cycloalkyl, especially with 5–6 ring carbon atoms) or denote cycloalkyl, especially with 4–8 ring carbon atoms, which is optionally substituted by $C_{1-4}$-alkyl, $CF_3$, $C_{1-4}$-alkenyl or $C_{1-4}$-alkynyl or optionally contains a fused aromatic or cycloaliphatic ring, or denote a heterocyclic structure, especially a 5-membered or 6-membered heterocyclic structure, which contains S, O or N and can also contain a fushed cycloaliphatic or aromatic or additional heterocyclic ring and can also optionally be substituted, or R[11] or R[12] also represent aryl, preferably phenyl or naphthyl, either of which is optionally substituted [Possible substituents for the aforementioned groups are $C_{1-4}$-alkyl, $C_{1-4}$-halogenoalkyl, especially $CF_3$, halogen, $C_{1-4}$-alkoxy and halogenoalkoxy with 1–4 carbon atoms, acetyl or aryloxy or arylmercapto in which aryl in particular represents phenyl or naphthyl (which can optionally be substituted by halogen, $C_{1-4}$-alkyl, $CF_3$, $C_{1-4}$-alkoxy, $NO_2$ or $C_{1-4}$-alkylmercapto); further substituents are $C_{1-4}$-alkylmercapto and halogenoalkylmercapto with 1–4 carbon atoms, $C_{1-4}$-alkylsulphonyl, $C_{1-4}$-alkoxycarbonyl, aminocarbonyl, CN, $NO_2$ and monoalkylamino and dialkylamino, especially with 1–4 carbon atoms in each alkyl radical; and the aryl radicals can also contain fused cycloaliphatic or heterocyclic rings], or $R^{11}$ or $R^{12}$ form, conjointly with the adjacent N atom, a 3–7-membered heterocyclic ring which can also contain further O, S or N hetero-atoms, can optionally be substituted and can optionally contain fused aromatic or heterocyclic rings, or $R^{12}$ can also additionally denote OH, alkoxy, especially $C_{1-4}$-alkoxy (which alkoxy group is optionally substituted by aryl, especially phenyl, which can itself be optionally substituted), or an acyl group

in which $R^{13}$ denotes hydrogen or alkyl, especially $C_{1-12}$-alkyl, or alkenyl, especially $C_{2-8}$-alkenyl [which are each optionally substituted by halogen, $C_{1-4}$-alkoxy, aryloxy (especially phenoxy which is optionally substituted by halogen, methyl or $NO_2$), alkylmercapto, especially $C_{1-4}$-alkylmercapto, arylmercapto (especially phenylmercapto which is optionally substituted by halogen or methyl) or aryl (especially phenyl which is substituted by halogen or $C_{1-4}$-alkyl)], alkynyl, especially $C_{2-8}$-alkynyl, cycloalkyl, especially with 3–6 ring carbon atoms, aryl, especially phenyl or naphthyl (which aryl group is optionally substituted by halogen, $C_{1-4}$-alkoxy, $C_{1-4}$-alkyl, $CF_3$ or $NO_2$), or a heterocyclic structure, especially a 5-membered or 6-membered heterocyclic structure, which contains O, S or N and can optionally contain a fused cycloaliphatic, cycloaromatic or heterocyclic radical, or $R^{12}$ can denote a carboxylic acid ester group

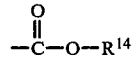

in which $R^{14}$ denotes alkyl, especially $C_{1-12}$-alkyl, alkenyl, especially $C_{3-12}$ alkenyl, or alkynyl, especially $C_{3-12}$ alkynyl [which groups are optionally substituted by halogen, $C_{1-4}$-alkoxy, aryl (especially phenyl which is optionally substituted by halogen or $C_{1-4}$-alkyl), cycloalkyl, especially with 5–6 ring carbon atoms, or a heterocyclic structure, especially a 5- or 6-membered heterocyclic structure, which contains Q, S or N] or denotes cycloalkyl, especially with 5–6 ring carbon atoms (which is optionally substituted by $C_{1-4}$-alkyl) or aryl, especially phenyl or naphthyl (which aryl group is optionally substituted by halogen, $C_{1-4}$-alkyl, $CF_3$, $C_{1-4}$-alkoxy, $C_{1-4}$-alkylmercapto, $NO_2$ or CN), or $R^{12}$ can denote a carboxylic acid amide group

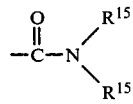

in which the $R^{15}$ moieties are identical or different and denote hydrogen or alkyl, especially $C_{1-12}$-alkyl, or alkenyl, especially $C_{3-8}$-alkenyl, (which groups are optionally substituted by halogen, $NO_2$, $C_{1-4}$-alkyl, $CF_3$ or $C_{1-4}$-alkoxy), or denote aryl, especially phenyl (which aryl group is optionally substituted by halogen, $C_{1-4}$-alkyl, $CF_3$, $C_{1-4}$-alkoxy, $C_{1-4}$-alkylmercapto or $NO_2$), or cycloalkyl, especially with 5–6 ring carbon atoms, or a sulphonyl group $—SO_2—R^8$ in which $R^8$ has the above-mentioned meaning, or $R^{12}$ can denote the group

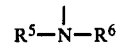

in which $R^5$ and $R^6$ have the above-mentioned meanings. If X and Y conjointly represent the group $=N—R^3$, $R^3$ can, conjointly with Z and the adjacent carbon atom, form a heterocyclic structure of one of the following formulas

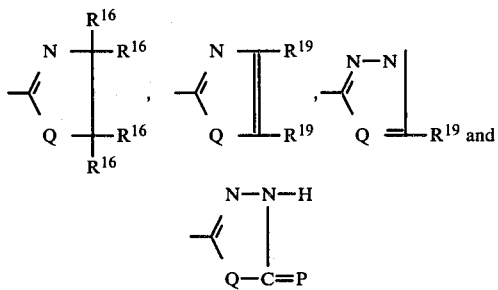

in which the $R^{16}$ moieties are identical or different and denote hydrogen, $C_{1-4}$-alkyl, $C_{1-4}$-halogenoalkyl (especially with Cl or Br as the halogen), $C_{1-4}$-alkoxy or aryloxy, especially phenoxy(which aryloxy group is optionally substituted by halogen, $C_{1-4}$-alkyl, $C_{1-4}$-alkoxy or $NO_2$), Q denotes O, S or the group

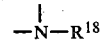

in which R denotes hydrogen, $C_{1-6}$-alkyl, cycloalkyl with 3–7 ring carbon atoms or aryl (especially phenyl which is optionally substituted by Cl, $C_{1-4}$-alkoxy, $C_{1-4}$-alkyl or $NO_2$), $R^{19}$ denotes hydrogen or alkyl, especially $C_{1-12}$-alkyl [which alkyl is optionally substituted by $C_{1-4}$-alkoxy, aryloxy (especially phenoxy which is optionally substituted by methyl or halogen), $C_{1-4}$-alkylmercapto, arylmercapto (especially phenylmercapto which is optionally substituted by methyl or halogen) or aryl (especially phenyl or naphthyl which are optionally substituted by $C_{1-4}$-alkyl, $C_{1-4}$-alkoxy or halogen)], or denotes cycloalkyl, especially with 5–6 ring carbon atoms (which cycloalkyl group is optionally substituted by $C_{1-4}$-alkyl or halogen), aryl, especially phenyl or naphthyl (which aryl group is optionally substituted by $C_{1-4}$-alkoxy, $C_{1-4}$-alkylmercapto or $NO_2$), a heterocyclic structure, especially a 5-membered or 6-membered heterocyclic structure which contains O, S or N and optionally contains fused cycloaliphatic, cycloaromatic or heterocyclic radicals (and can optionally be substituted, especially by halogen), alkoxy, especially $C_{1-12}$-alkoxy, aryloxy, especially phenoxy (which aryloxy group is optionally substituted by halogen, $C_{1-4}$-alkyl, $CF_3$, $C_{1-4}$-alkoxy, $C_{1-4}$-alkylmercapto, $C_{1-4}$-alkylsulphonyl, $NO_2$, CN, $COO(C_{1-4}$-alkyl), CONH₂ or N(C₁₋₄-alkyl)₂), alkylmercapto, especially C₁₋₁₂-alkylmercapto (which is optionally substituted by C₁₋₄-alkoxy, cycloalkyl, especially cyclohexyl, or aryl, especially phenyl which is optionally substituted by chlorine, nitro, methoxy or methyl), or amino (which is optionally substituted by C₁₋₁₂-alkyl, cycloalkyl with 3 to 7 ring carbon atoms, aralkyl or aryl, especially benzyl or phenyl (which are optionally substituted by halogen, C₁₋₄-alkyl, CF₃, NO₂ or C₁₋₄-alkylmercapto)), or optionally, two radicals R¹⁹ can also conjointly form a ring, preferably an aromatic ring, which is fused onto the heterocyclic structure mentioned, and P denotes O or S.

Z can also denote an azide group.

X, Y and Z can also, conjointly with the adjacent carbon atom, denote a nitrile group.

A further preferred class of compounds of the formula (I) are those
in which X and Y represent the radical =N-aryl, especially =N-phenyl, and Z represents halogen, C₁₋₄-alkoxy or alkylmercapto, aryloxy, arylmercapto, the radical -NH-aryl or the radical

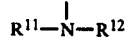

in which R¹¹ and R¹² are identical or different and have the meanings stated above.

Compounds in which X, Y and Z independently of one another denote fluorine, chlorine, phenoxy which is optionally substituted by Cl, or methylmercapto are particularly preferred.

Also particularly preferred are those compounds
in which X and Y conjointly denote oxygen and Z denotes OH, N₃ or O—R¹⁰
in which R¹⁰ denotes alkyl with 1–12 carbon atoms (which is optionally substituted by chlorine, OH, CN, C₁₋₄-alkoxy, C₁₋₂-alkoxy-C₁₋₂-alkoxy or phenyl) or cyclohexyl or denotes alkenyl or alkynyl with 3 carbon atoms, or
Z denotes the radical

in which R¹¹ and R¹² independently of one another denote hydrogen, C₁₋₁₂-alkyl (which is optionally substituted by CN, OH, CONH₂, COOH, phenyl or N-4,5-dichloroimidazole-2-carboxamide), cyclohexyl, alkenyl or alkynyl with 3–6 carbon atoms or aryl, in particular phenyl or naphthyl which are optionally substituted [possible substituents here are C₁₋₄-alkyl, C₁₋₄-halogenoalkyl, especially CF₃, halogen, C₁₋₄-alkoxy and C₁₋₄-halogenoalkoxy, acetyl or aryloxy or arylmercapto in which aryl in particular represents phenyl or naphthyl (which can optionally be substituted by halogen, C₁₋₄-alkyl, CF₃, C₁₋₄-alkoxy, NO₂ or C₁₋₄-alkylmercapto); further substituents are C₁₋₄-alkylmercapto and C₁₋₄-halogenoalkylmercapto, C₁₋₄-alkylsulphonyl, C₁₋₄-alkoxycarbonyl, aminocarbonyl, CN, NO₂ and monoalkylamino and dialkylamino, especially with 1–4 carbon atoms in each alkyl radical;

the aryl radicals can also contain fused cycloaliphatic or heterocyclic rings], or
R¹¹ and R¹² can, conjointly with the adjacent nitrogen atom, form a 5-membered to 7-membered heterocyclic ring which can optionally contain a further N or O atom, or R¹¹ and R¹² can denote the radical CHO or

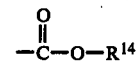

in which R¹⁴ denotes C₁₋₄-alkyl,
or can denote the radical

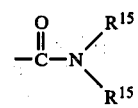

in which the R¹⁵ moieties, independently of one another, each denote hydrogen, C₁₋₄-alkyl or phenyl, or can denote the radical

in which R⁵ and R⁶ independently of one another each denote hydrogen, phenyl, COCCl₃ or COOC₂H₅ or form, conjointly with the adjacent nitrogen atom, the radical

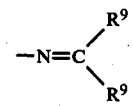

in which the R⁹ moieties independently of one another each denote hydrogen, C₁₋₄-alkyl or phenyl which is optionally substituted by OH.

Another class of preferred compounds are those in which
X and Y conjointly denote oxygen and
Z denotes S—R¹⁰
in which R¹⁰ denotes C₁₋₄-alkyl, especially methyl.

Another preferred class of compounds are those in which X and Y conjointly denote sulphur and Z denotes methylmercapto and amino.

Yet another preferred class of compounds are those in which X and Y conjointly denote the radical =N—R³
in which R³ denotes hydrogen, OH, C₁₋₄-alkyl, benzoyloxy or pyridyl or aryl, especially phenyl or naphthyl which are optionally substituted [possible substituents being C₁₋₄-alkyl, C₁₋₄-halogenoalkyl, especially CF₃, halogen, C₁₋₄-alkoxy and C₁₋₄-halogenoalkoxy, acetyl or aryloxy or arylmercapto in which aryl preferably represents phenyl or naphthyl (which can optionally be substituted by halogen, C₁₋₄-alkyl, CF₃, C₁₋₄-alkoxy, NO₂ or C₁₋₄-alkylmercapto), further substituents being C₁₋₄-alkylmercapto, C₁₋₄-halogenoalkylmercapto, C₁₋₄-alkylsulphonyl, C₁₋₄-alkoxycarbonyl, aminocarbonyl, CN, NO₂ and monoalkylamino and dialkylamino, especially with 1–4 carbon atoms in each alkyl radical; the aryl radicals also possibly containing a fused cycloaliphatic or heterocyclic ring], and Z preferably denotes alkoxy with 1–4 carbon atoms, chlorine or arylmercapto (especially phenylmercapto which is optionally substituted by Cl or $C_{1-4}$-alkyl), or denotes

in which $R^{11}$ and $R^{12}$ independently of one another each denote hydrogen, $C_{1-4}$-alkyl, pyridyl or aryl, preferably phenyl (which is optionally substituted by $C_{1-4}$-alkyl, halogen, $C_{1-4}$-halogenoalkyl, $C_{1-4}$-alkoxy, $C_{1-4}$-alkylmercapto, $C_{1-4}$-halogenoalkylmercapto or $C_{1-4}$-halogenoalkoxy).

Compounds in which X, Y and Z conjointly with the adjacent carbon atom denotes an oxazole, thiazole, imidazole, oxadiazole, thiadiazole or 1,2,4-triazolone radical are also particularly preferred. These radicals can also contain a fused benzene ring and can also be substituted by amino or $C_{1-4}$-alkyl or by phenyl or phenoxy (which are optionally substituted by $NO_2$), or by furyl or pyridyl or by thiazole (which is optionally substituted by chlorine).

Furthermore, salts with the following cations are particularly preferred: sodium or $NR_4$
in which the R's independently of one another each denote hydrogen, alkyl with 1 to 4 carbon atoms (which is optionally substituted by hydroxyl) or benzyl, and two of the R's may be linked together to form a morpholine ring or three of the R's may be linked together to form a pyridine ring.

The compound of the formula (I) in which

forms the CN group is also particularly preferred. 4,5-Dichloroimidazole-2-carboxylic acid derivatives of the general formula

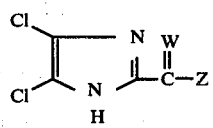     (XVI)

in which W represents O, S or the radical =N-aryl and Z, if W represents the radical =N-aryl, represents halogen, alkoxy, alkylmercapto, aryloxy, arylmercapto, the radical —NH-aryl or the radical

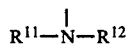

in which $R^{11}$ or $R^{12}$ are identical or different and have the meanings stated above, or
Z, if W represents O or S, represents the radical —NH-aryl,
are also preferred.

Compounds according to the invention can be prepared by reacting 4,5-dichloro-2-dichloromethyleneimidazole of the formula (II) or 4,5-dichloro-2-trichloromethyl-imidazole of the formula (III) or the dimeric ketene of 4,5-dichloroimidazole-2-carboxylic acid, of the formula (IV)

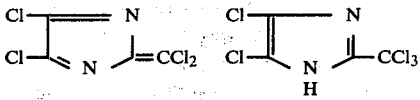
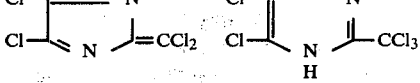

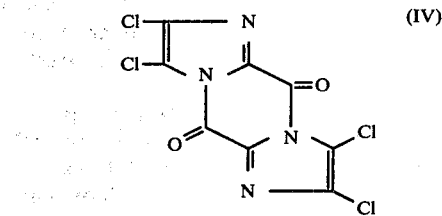

with nucleophilic reagents of the general formula H—Z, in which Z has the above-mentioned meaning,
optionally in the presence of an acid-binding agent and/or in the presence of water or with subsequent treatment of the reaction products with water, and optionally converting the reaction product into a salt thereof with the aid of a base, or by reacting a compound of the general formula

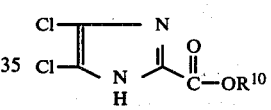   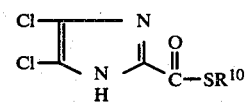

(VI)        (VII)

or

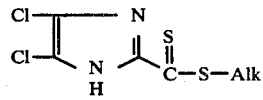

(VII)

in which $R^{10}$ has the above-mentioned meaning and Alk represents a lower alkyl radical,
with a nucleophilic reagent of the general formula

in which $R^{11}$ and $R^{12}$ have the above-mentioned meanings,
or by reacting 4,5-dichloroimidazole-2-carboxylic acid nitrile with a nucleophilic reagent of the general formula H—Z, in which Z has the above-mentioned meaning,
or by reacting 4,5-dichloroimidazole-2-thiocarboxamide with an alkylating agent and subsequently hydrolyzing or cyclizing the reaction product, or by reacting the imide-chloride of the general formula

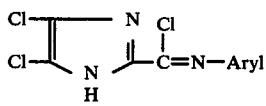

in which Aryl represents an aryl radical,
with a compound of the general formula H—Z,
in which Z has the above-mentioned meaning, optionally in the presence of a diluent and an acid-binder, or by hydrolyzing the imide-chloride of the formula (XIV), optionally in the presence of a diluent, or by reacting 4,5-dichloro-2-dichloromethyleneimidazole of the formula (II) with an equimolar amount of an amine of the formula (XV), optionally in the presence of a diluent, at temperatures below 90° C.

All of the processes for the preparation of the 4,5-dichloroimidazole-2-carboxylic acid derivatives according to the invention start from 4,5-dichloro-2-dichloromethyleneimidazole of the formula (II) or from 4,5-dichloro-2-trichloromethylimidazole of the formula (III). These compounds have not yet been described in the literature to date. 4,5-Dichloro-2-dichloromethylene-imidazole (II) is obtained when 2,4,5-trichloro-2-trichloromethyl-2H-imidazole (V) (obtainable, for example, by chlorination of 2-methyl-imidazole) is heated with red phosphorus or other reducing agents, such as, for example, copper(I) chloride, thus:

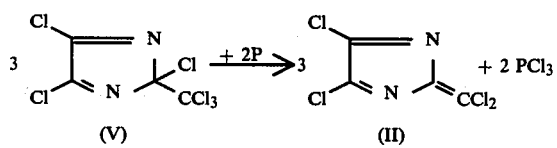

This process is the subject of U.S. Pat. No. 4,021,443.

4,5Dichloro-2-trichloromethyl-imidazole of the formula (III), which can also be used as a starting material, is obtained from 4,5-dichloro-2-dichloromethyleneimidazole of the formula (II) by allowing dry hydrogen chloride to act on this compound:

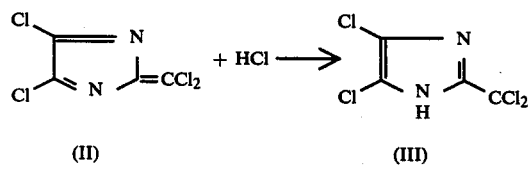

This reaction is preferably carried out in inert solvents, such as aliphatic or aromatic hydrocarbons or halogenated hydrocarbons, for example benzine, dichloromethane, chloroform, carbon tetrachloride, benzene, toluene or chlorobenzene, or in ethers, such as diethyl ether, dibutyl ether, tetrahydrofuran or dioxane.

The dimeric ketene of 4,5-dichloroimidazole-2-carboxylic acid, of the formula (IV), which can also be employed as a further intermediate, can be obtained (a) by controlled hydrolysis of the compound (II) in accordance with the following reaction equation:

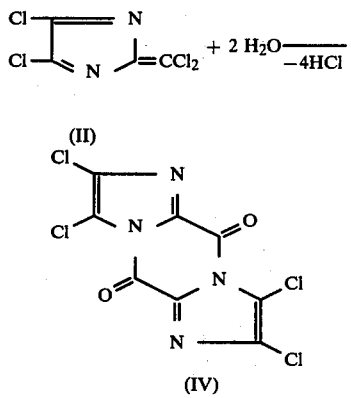

The compound (IV) can be obtained in a particularly advantageous manner when (b) the 1:1 addition compound of compound (II) and the dialkylamide of a lower aliphatic carboxylic acid, preferably N,N-dimethylformamide, which has the presumed formula

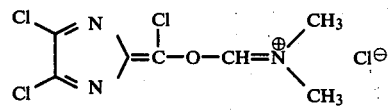

is subjected to scission at elevated temperatures, preferably 50° C. to 100° C. The reaction is preferably carried out in inert, non-polar solvents, such as petroleum ether or carbon tetrachloride.

In this case it is advantageous to subject the addition compound which is produced in situ directly to scission, whereupon compound (IV) is formed.

A further process for the preparation of the compound (IV) consists in (c) reacting 4,5-dichloroimidazole-2-carboxylic acid of the formula (XI) with an inorganic acid halide, preferably thionyl chloride:

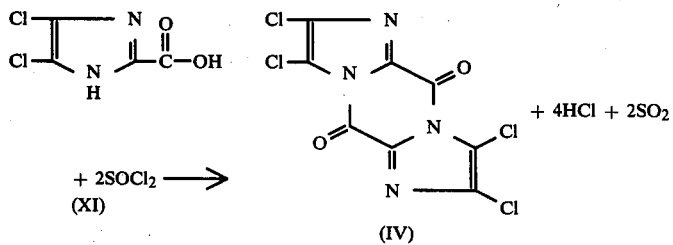

The reaction is preferably carried out in an excess of the acid chloride as the solvent, at temperatures between 0° C. and the boiling point of the acid chloride, and the compound (IV) is isolated by distilling off the excess acid chloride.

The procedure employed to prepare compounds of the formula (I) in which X, Y and Z denote chlorine or fluorine, provided that at least one of these radicals denotes fluorine (formula III a, b, c), is to allow dry hydrogen fluoride and/or, optionally, metal fluorides to act on the compound of the formula (II) or (III). The reaction can be carried out stepwise:

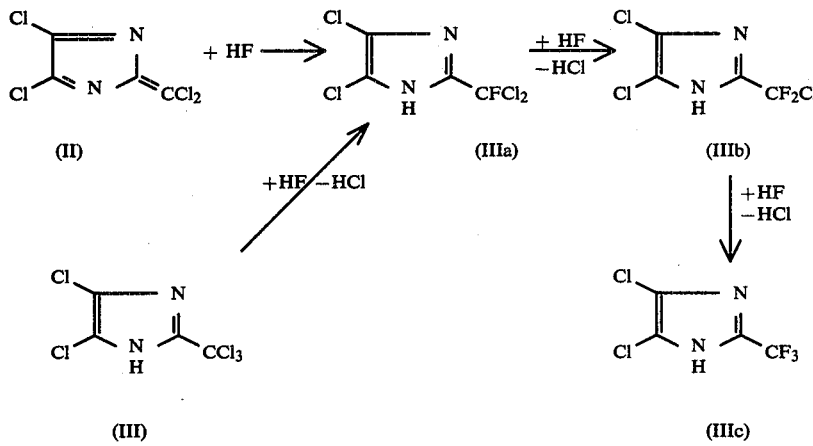

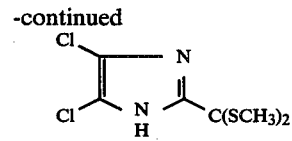

The reactions are preferably carried out in hydrocarbons as the solvent or in excess hydrofluoric acid. The reaction temperatures are 0° to 200° C. and are preferably 0° to 50° C. for the compound of the formula (IIIa) and preferably 20° to 150° C. for the compounds of the formulae (IIIb) and (IIIc).

In order to prepare the compounds of the formula (I) in which X, Y and Z denote the groups —S—$R^1$, —O—$R^2$ and —S—$R^2$, 2-trichloromethyl-4,5-dichloro-imidazole (III) is reacted with phenols, mercaptans or thiophenols in the presence of acid-binding agents.

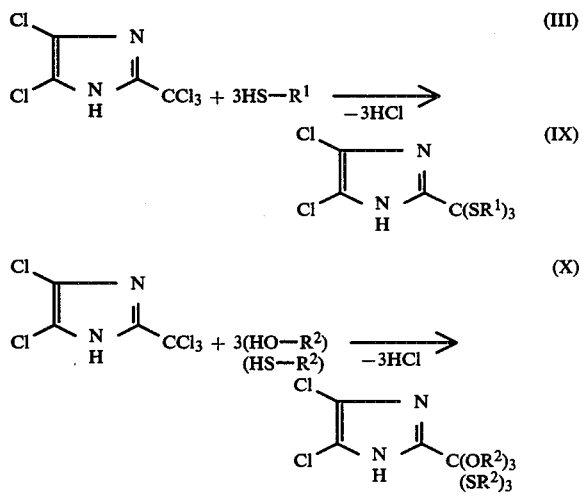

With phenol or methylmercaptan as the reactant, the course of the reaction is, for example, as follows:

These reactions are carried out in inert solvents, such as hydrocarbons, ethers or ketones. The acid-binding agents used are preferably alkali metal oxides, hydroxides or carbonates, alkaline earth metal oxides, hydroxides or carbonates, or tertiary amines. However, it is also possible to employ previously prepared alkali metal phenolates, mercaptides or thiophenolates or alkaline earth metal phenolates, mercaptides or thiophenolates for the reaction and then to carry out the reaction without further addition of acid-binding agents. The reactions can also be carried out in the presence of water by, for example, using aqueous alkalis as acid acceptors and it is possible to work both in water-miscible solvents or, in a two-phase system, in water-immiscible solvents. The reaction temperatures can be varied within a wide range, for example between —20° C. and 150° C. The reaction is preferably carried out at between 0° and 100° C.

The meaning of $R^1$ and $R^2$ in the formula (IX) and (X) has already been defined above; compounds in which $R^1$ represents methyl and compounds in which $R^2$ represents phenyl which is optionally substituted by Cl are very particularly preferred.

The compound of the formula (I) in which X and Y conjointly denote an oxygen atom and Z denotes the OH group, that is to say 4,5-dichloro-imidazole-2-carboxylic acid, can be prepared by subjecting the compound of the formula (II) or (III) to acid hydrolysis. The reactions proceed in the following way:

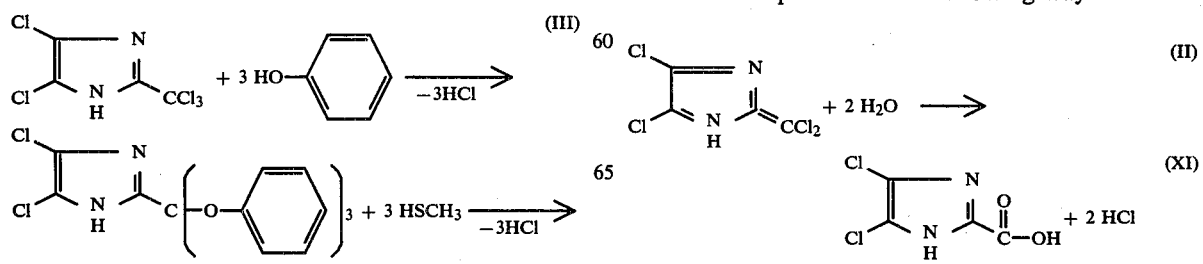

-continued

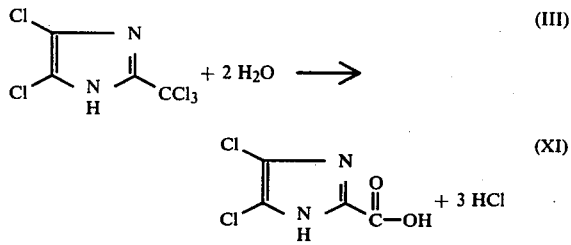

Mineral acids diluted with water, for example 5 to 90% strength sulphuric acid or phosphoric acid or 5 to 35% strength hydrochloric acid, or anhydrous or water-containing organic carboxylic acids, for example formic acid, acetic acid, oxalic acid or benzoic acid, can be used as the reaction medium which supplies water. If anhydrous organic carboxylic acids are used as the hydrolyzing agent, the reaction can also be carried out in the presence of salts of these acids, for example with mixtures of acetic acid and sodium acetate. The reactions are carried out in the temperature range of between 0° and 150° C., preferably between 20° and 120° C.

However, it is most convenient to carry out the hydrolysis with water alone. For this purpose it suffices briefly to heat the compound of the formula (II) or (III) in excess water to the boiling point thereof, until a clear solution is obtained. The carboxylic acid of the formula (XI) crystallizes out on cooling.

The methods used to convert 4,5-dichloro-imidazole-2-carboxylic acid into its salts of the formula (XII) or (XIII)

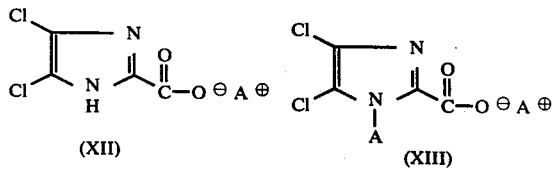

in which A has the above-mentioned meaning, are those customary for the conversion of organic carboxylic acids or NH-acid compounds into their salts, that is to say the carboxylic acid is reacted with appropriate metal oxides or metal hydroxides in the desired stoichiometric ratio, or is reacted with the stoichiometric amount or twice the stoichiometric amount of ammonia or of a primary, secondary or tertiary amine. An alternative procedure is to react metal salts of the carboxylic acid with inorganic salts of those anions which form a sparingly soluble salt with the cation originally bonded to the carboxylic acid. These reactions are preferably carried out in water or alcohols or in mixtures of these. The reactions with ammonia and amines can also be carried out in organic solvents which are inert towards amines.

Amine salts of the carboxylic acid are also obtained direct from the compounds of the formula (II) and (III) by reacting these compounds with at least three of four moles of a tertiary amine in the presence of water, for example in accordance with the following equation:

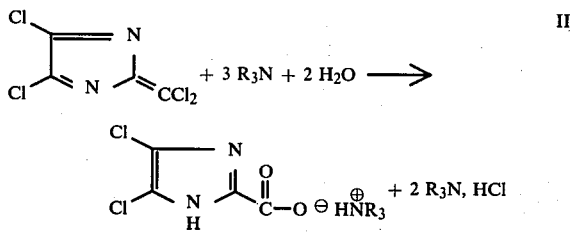

This reaction is carried out at from 0° to 100° C., and preferably at from 20° to 70° C. As a rule, the amine hydrochloride which is formed at the same time can be separated off because the amine salts of the carboxylic acid are more sparingly soluble in water.

Salts of the formula (XII) with primary aliphatic amines can also easily be prepared from compounds of the formulae (II) and (III) by a one-pot process in an aqueous medium. For this purpose, the amine/water mixture is first rendered acidic (preferably with hydrochloric acid) and then heated briefly with the compound of the formula (II) or (III), preferably to 80° to 110° C. When the reaction medium has been rendered weakly alkaline, preferably with bicarbonate, the desired salt precipitates out.

The procedure employed in order to prepare the compounds of the formula (I) in which X and Y conjointly denote an oxygen atom and Z denotes the radical $OR^{10}$ (formula VI), in which $R^{10}$ denotes optionally substituted alklyl or cycloalkyl, alkenyl or alkynyl, is to react a compound of the formula (II), (III) or (IV) with the appropriate aliphatic or cycloaliphatic alcohol.

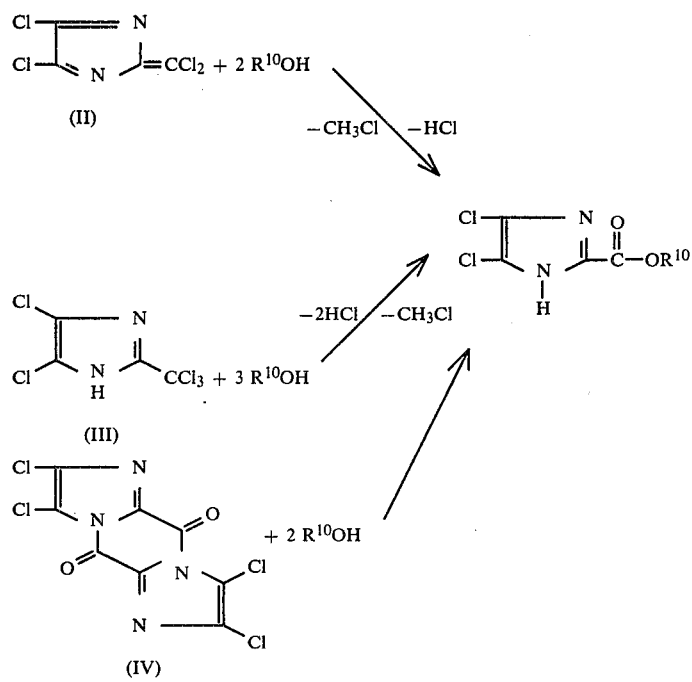

When methanol and compounds of the formula (II) and (III) are used as the reactants, the course of the reaction can be represented in the following way:

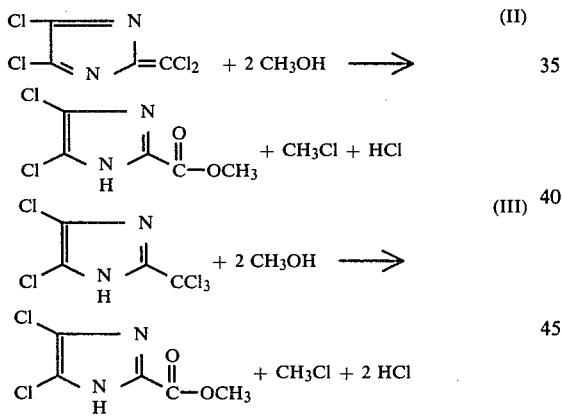

As can be seen from the reaction equations, for complete conversion at least two moles of the particular alcohol are required per mole of the compound (II) or (III). The reaction can be carried out in an excess of the alcohol as the solvent or also in inert solvents, such as aliphatic and aromatic hydrocarbons and halogenated hydrocarbons, for example benzine, carbon tetrachloride, toluene or chlorobenzene, or in ethers, for example diethyl ether, dibutyl ether, tetrahydrofuran or dioxane. The reactions can be carried out within a wide temperature range, say between 0° and 125° C. The reactions are preferably carried out at 15° to 100° C. In general, the reaction products are isolated by removing the excess solvent, and the alkyl chloride formed during the reaction, by simple distillation.

In order to bind the hydrogen chloride liberated during the reaction, it is also possible to add acid-binding agents, for example alkali metal oxides, hydroxides and carbonates, alkaline earth metal oxides, hydroxides and carbonates and also tertiary amines, in an up to stoichiometric amount.

When glycol and the dimeric ketene of the formula (IV) are used as the starting materials, the reaction takes the following course:

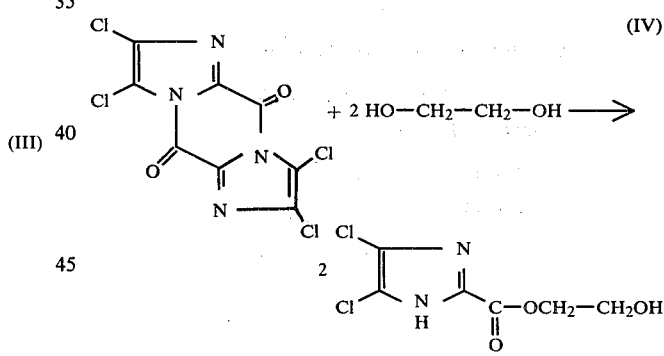

The reactions between the dimeric ketene of the formula (IV) and alcoholic reaction components are carried out in inert solvents, such as aliphatic and aromatic hydrocarbons and halogenated hydrocarbons, open-chain and cyclic ethers, ketones, dimethylformamide or dimethylsulphoxide, or, alternatively, in the particular alcohol employed as a reactant, as the solvent. At least twice the molar amount of the alcohol is required per mole of the compound (IV) in order to effect complete conversion. The reaction temperatures are 0° to 200° C. and preferably from 15° C. up to the boiling point of the solvent employed, or of the alcohol.

For the cases described, the radical $R^{10}$ in formula (VI) denotes: alkyl with 1 to 18 carbon atoms or alkenyl with 3 to 12 carbon atoms, which can be substituted by halogen, especially chlorine and bromine, hydroxyl, acyloxy (in which acyl denotes the radical of an aliphatic, cycloaliphatic, araliphatic, aromatic or heterocyclic carboxylic acid, inter alia including the radical

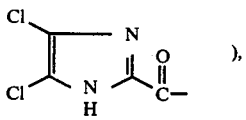

$C_{1-4}$-alkoxy, $C_{1-4}$-alkoxy-$C_{1-4}$-alkoxy (especially with a $C_2$ chain between the oxygen atoms), aryloxy (optionally substituted by halogen, methyl or nitro), $C_1$-$C_4$-alkylmercapto, benzylmercapto (optionally substituted in which X and Y conjointly denote an oxygen atom and Z denotes the radical $OR^{10}$ (formula(VI))

in which $R^{10}$ denotes optionally substituted aryl, are as follows.

(a) The compound of the formula (II) or (III) is reacted with at least an equimolar amount of a phenol in the presence of at least two or three molar equivalents of an acid-binding agent and water. When phenol is used as a reactant, the reaction takes the following course:

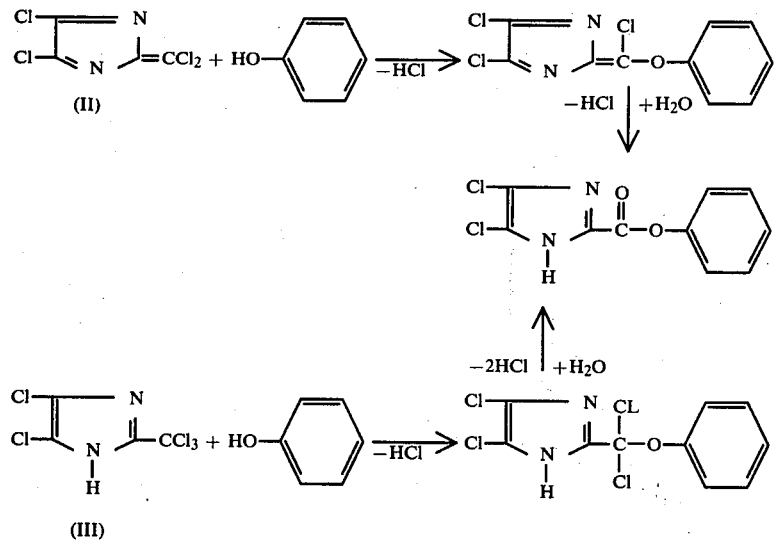

in the aryl radical by chlorine), arylmercapto, especially phenylmercapto (optionally substituted in the phenyl radical by chlorine or methyl), acylamino (in which acyl denotes the radical of an aliphatic, araliphatic, cycloaliphatic, aromatic or heterocyclic carboxylic acid, inter alia including the radical

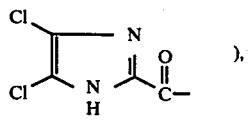

CN, radicals of carboxylic acid esters, cycloalkyl with 5–6 ring carbon atoms, aryl, especially phenyl or naphthyl which are optionally substituted by Cl, $CH_3$ or $C_{1-4}$-alkoxy, or 5- or 6-membered heterocyclic structures which can contain N, O or S as the hetero-atoms, especially furyl, thienyl or pyridyl; alternatively $R^{10}$ denotes $C_{3-12}$-alkynyl or cycloalkyl with 5–6 ring carbon atoms, which is optionally substituted by $C_{1-4}$-alkyl or contains fused rings.

Carboxylic acid esters of the formula (VI) with tertiary alcohols can be obtained from the carboxylic acid of the formula (XI) and alkenes, especially isobutylene and isoamylene, under the catalytic influence of strong acids such as, for example, sulphuric acid, perchloric acid and boron trifluoride etherate, if appropriate in the presence of solvents such as, for example, dioxane (see "Houben-Weyl", 4th edition, 1952, volume VIII, page 534 and "Methodicum Chimicum", 1975, volume V, page 652).

The procedures employed in order to prepare the compounds of the formula (I)

The reactions can be carried out in water as the reaction medium, in water-miscible solvents, such as alcohols, for example methanol or ethanol, ketones, for example acetone, or ethers, for example tetrahydrofuran or dioxane, or also in a two-phase system using aliphatic or aromatic hydrocarbons or halogenated hydrocarbons as the solvent. As can be seen from the reaction equations, at least one or two moles of water and two or three moles of an acid-binding agent are required. Alkali metal hydroxides and carbonates and alkaline earth metal hydroxides and carbonates are preferably used as the acid-binding agents. The reaction temperatures vary between $-10°$ and $100°$ C., preferably between $5°$ and $60°$ C.

(b) 2-Triaryloxymethyl-4,5-dichloro-imidazoles of the formula (X) are subjected to partial saponification in a basic medium. The reaction takes the following course for the preparation of the phenyl ester:

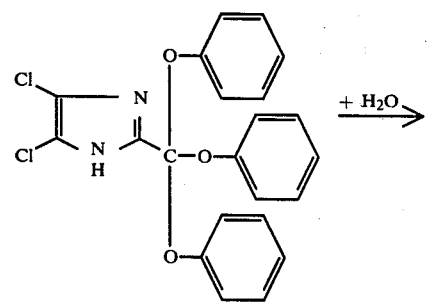

-continued

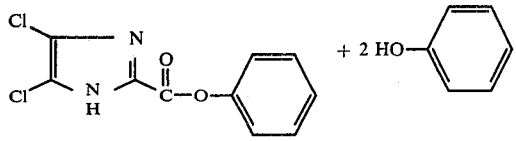

The reaction is carried out in the presence of at least one mole of water and at least two molar equivalents of a strong base, preferably alkali metal hydroxides or carbonates and alkaline earth metal hydroxides or carbonates, and water-miscible solvents, such as alcohols, acetone, dioxane or tetrahydrofuran, can simultaneously be present as solubilizing agents. The reaction temperatures are between 0° and 100° C., preferably between 15° and 75° C.

In these cases, $R^{10}$ preferably denotes phenyl or naphthyl which is optionally substituted by halogen, alkyl ($C_1$-$C_4$), $CF_3$, alkoxy ($C_1$-$C_4$), alkylmercapto ($C_1$-$C_4$), alkylsulphonyl ($C_1$-$C_4$), alkoxycarbonyl, cyano or nitro.

Compounds in which $R^{10}$ denotes phenyl or nitrophenyl are particularly preferred.

The procedure employed in order to prepare the compounds of the formula (I) in which X and Y conjointly denote an oxygen atom and Z denotes the radical S—$R^{10}$ (formula (VII)) is that 4,5-dichloro-imidazole-2-thiocarboxamide (XLIII) (the preparation of 4,5-dichloro-imidazole-thiocarboxamide, which is required as the starting material, is described hereinbelow) is converted, using an alkylating agent, into the salt of a corresponding imino-thioether and the latter is subjected to hydrolysis in a neutral or acid medium. When methyl iodide is used as the reactant, the reaction takes, for example, the following course:

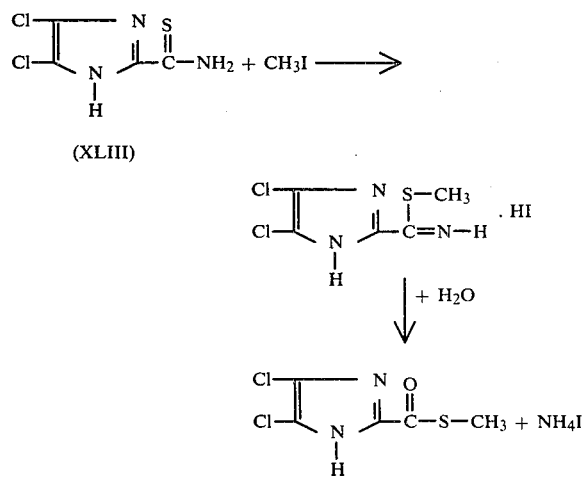

The alkylating agents used are the alkyl halides, dialkyl sulphates, sulphonic acid alkyl esters and the like which are customarily used for this purpose. The first reaction stage is carried out in a solvent which is substantially anhydrous.

Aromatic hydrocarbons, nitromethane, alcohols, ketones, open-chain and cyclic ethers and the like are particularly suitable. The reaction temperatures are between 0° and 120° C. and preferably between 20° and 100° C.

The second stage of the reaction is carried out with the aid of at least the equimolar amount of water and is preferably carried out in excess water as the reaction medium, to which mineral acids can be added until the pH value reaches 1. The addition of a water-miscible solvent is possible, but as a rule is not necessary.

In formula (VII), $R^{10}$ preferably denotes an alkyl radical which 1 to 12 carbon atoms, which can be substituted by one or more groups selected from hydroxyl, $C_1$-$C_4$-alkoxy, $C_1$-$C_4$-alkylmercapto, cyano, carboxylic acid ester, carboxamide and phenyl, which is optionally substituted by chlorine, nitro, methoxy or methyl, or denotes an alkenyl radical or an alkynyl radical with 3 to 12 carbon atoms.

However, the compound in which $R^{10}$ denotes methyl is particularly preferred.

The procedure employed in order to prepare the compounds of the formula (I) in which X and Y conjointly denote an oxygen atom and Z denotes an optionally substituted amino group (formula (XVII)

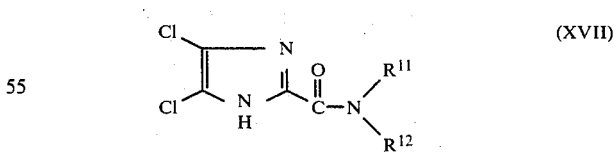

is that (a) the compound of the formula (II) or (III) is reacted with the hydrohalide of a primary or secondary amine and the compound of the amide-chloride type, which is thus formed, is then subjected to hydrolysis.

With dimethylamine hydrochloride, the reaction takes the following course:

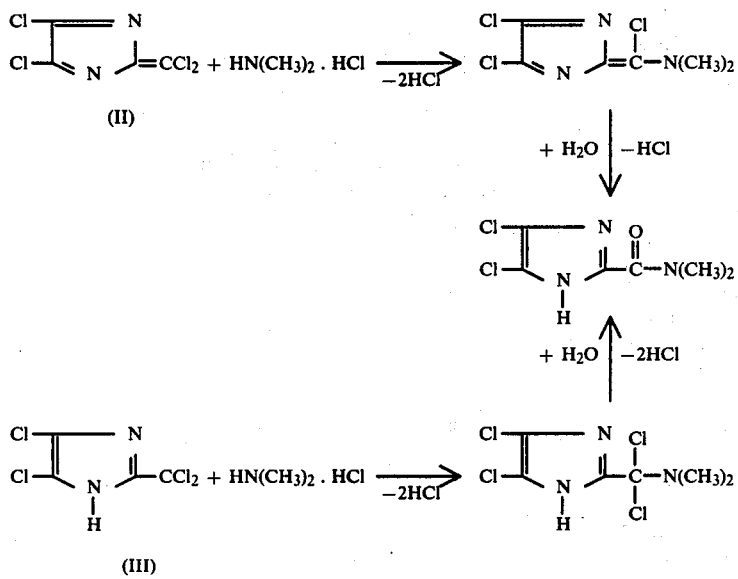

The first stage of the reaction is carried out in aprotic solvents. Cyclic ethers, such as tetrahydrofuran and dioxane, are particularly suitable. The reaction temperatures are 50° to 200° C. and preferably 70° to 120° C. The subsequent hydrolysis reaction can be carried out with or without previous isolation of the intermediates, by allowing water to act on these compounds. It is not necessary to bind the hydrogen chloride which is liberated, but the presence of equivalent amounts of acid-binding agents, for example alkali metal oxides, hydroxides or carbonates or alkaline earth metal oxides, hydroxides or carbonates, or tertiary amines, for the neutralization of this compound, is not harmful. The reaction temperatures for the hydrolysis reaction are from 0° to 100° C., preferably 10° to 70° C.

In order to prepare, 4,5-dichloro-imidazole-2-carboxylic acid amides of secondary amines which have a high degree of steric hindrance, for example diisopropylamine, the first stage of the reaction can also be carried out with the free amines themselves instead of with the hydrohalides.

The procedure is that the compounds of the formulae (II) or (III) are reacted, in inert solvents, such as hydrocarbons, chlorinated hydrocarbons, open-chain or cyclic ethers or ketones, or in lower alcohols, with at least twice the molar amount of a secondary amine which has a high degree of steric hindrance or with at least one mole of this amine with the addition of at least the equimolar amount of an acid-binding agent, such as alkali metal carbonates or alkaline earth metal carbonates or tertiary amines, in the temperature range between $-10°$ and $+120°$ C., preferably at 0°–75° C., and directly thereafter, or after removal of the solvent, at least the equimolar amount of water and, optionally, the amount of an inorganic or organic acid-binding agent which is necessary for neutralization, is allowed to act on the reaction product.

In the reaction with aromatic amines it is preferable to work at temperatures above 90° C. The course of the reaction can then be represented as follows:

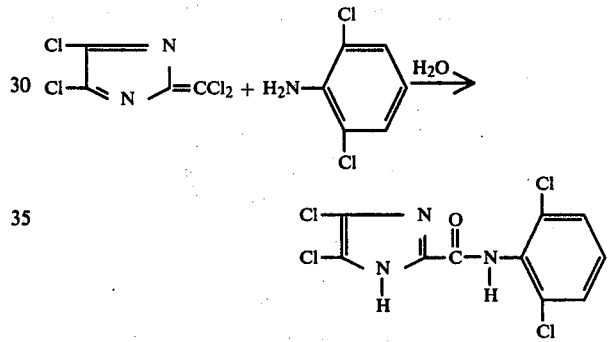

The reaction can be carried out using suitable diluents. Water is a preferred diluent. The reaction is preferably carried out in the presence of at least 1 mole of hydrochloric acid per mole of the aniline.

The reaction temperatures can be varied within a relatively wide range but the reaction is generally carried out at above 90° C. and preferably between 90° and 150° C.

The reaction can be carried out not only under normal pressure but also under elevated pressure.

Furthermore, compounds of the formula (XVII) can be obtained by carrying out the reaction involving the amine and the subsequent hydrolysis in two stages, that is to say by intermediate isolation of an amide-chloride of the formula (XIV).

If 4,5-dichloroimidazole-2-carboxylic acid N-(2,6-dichlorophenyl)-imide-chloride is used as the imide-chloride of the formula (XIV) and this is hydrolyzed, the course of the reaction can be represented as follows:

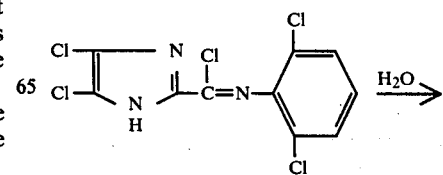

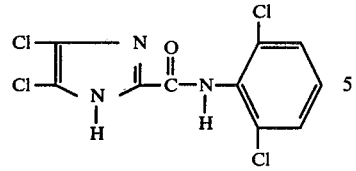

Concentrated sulphuric acid is preferably used as the hydrolyzing agent but the hydrolysis can also be carried out with other customary hydrolyzing agents, such as formic acid or concentrated hydrochloric acid.

The reaction temperatures can be varied within a relatively wide range; in general the reaction is carried out at room temperature.

The reaction can be carried out not only under normal pressure, but also under elevated pressure.

Imide-chlorides of the formula (XIV) are obtained by reacting 4,5-dichloro-2-dichloromethylene-imidazole of the formula (II) with an equimolar amount of an amine of the formula (XV) at temperatures below about 90° C.

If 4,5-dichloro-2-dichloromethylene imidazole of the formula (II) and an equimolar amount of an amine of the formula (XV), for example 2,6-dichloroaniline, are used, the course of the reaction at reaction temperatures below 90° C. can be represented by the following equation:

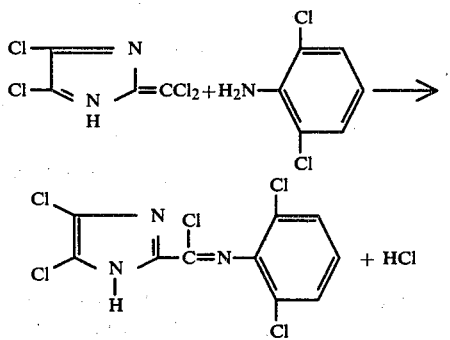

The reaction can be carried out using suitable diluents. The preferred diluent is water.

The reaction is also preferably carried out in the presence of at least 1 mole of hydrochloric acid per mole of the aniline.

The reaction temperatures can be varied within a relatively wide range but the reaction is generally carried out at below 90° C. and preferably at between 40° and 70° C.

The reaction can be carried out under normal pressure, but also under elevated pressure.

The amide-chlorides of the formula (XIV) which are obtained from this reaction, can serve as starting materials for the preparation of further compounds according to the invention.

(b) Furthermore, compounds of the formula (XVII) can be obtained by deacylating 4,5-dichloro-imidazole-2-carboxylic acid N-formylamides of the formula (XIX).

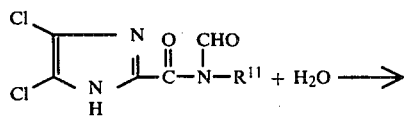
(XIX)

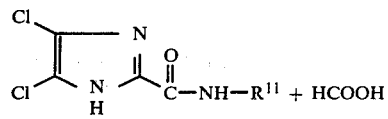
(XX)

With 4,5-dichloro-imidazole-2-carboxylic acid N-formylisopropylamide the reaction takes, for example, the following course:

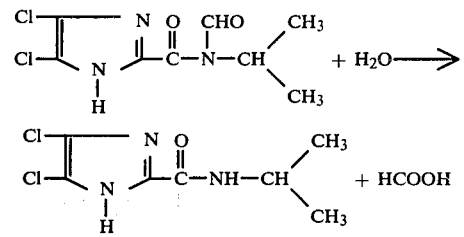

Aqueous mineral acids, or organic carboxylic acids, such as formic acid or oxalic acid, or concentrated mineral acids, such as, for example, concentrated sulphuric acid, are used as the hydrolyzing agent. The reaction temperatures are 10° to 150° C. and preferably 20° to 100° C., depending on the hydrolysing agent.

The 4,5-dichloro-imidazole-2-carboxylic acid N-formylamides (corresponding to formula (XIX)), which are required as precursors, are preferably obtained by reacting the compound of the formula (II) with at least two moles of a formic acid amide. This reaction can be carried out in the presence or absence of solvents. Examples of solvents which can be used are aliphatic and aromatic hydrocarbons and halogenated hydrocarbons, open-chain and cyclic ethers or aliphatic nitriles, such as, for example, acetonitrile; water can also be present. The reaction temperatures are from −10° to 110° C. when the reaction is carried out under anhydrous conditions. If water is present, the reaction temperature is −10° to +10° C.

With compound (II) and the N-isopropyl-formamide, the reaction takes, for example, the following course:

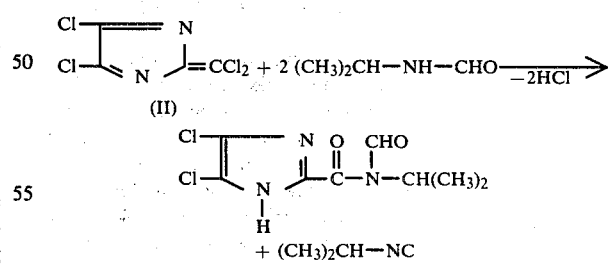

If, for this reaction, at least 1 mole of water is added per mole of the compound of the formula (II), the corresponding amide is obtained directly at a reaction temperature of 50° to 150° C., and preferably 80° to 120° C., in a one-pot process.

4,5-Dichloro-imidazole-2-carboxylic acid N-acylamides of the formula (XXI) which do not contain a hydrogen atom on the α-carbon atom of the acyl group can be prepared by an analogous route.

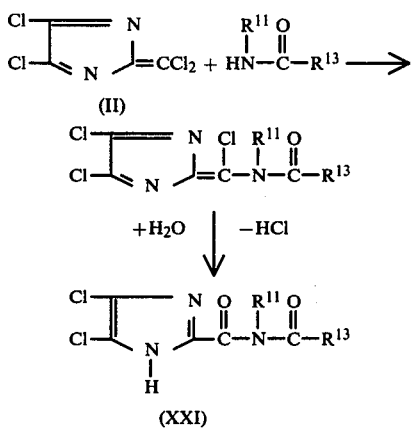

(XXI)

The first stage of the reaction is carried out in the same solvents and in the same temperature range as those indicated above. For the second reaction stage at least the equivalent amount of water is added, at a temperature of between 0° and 100° C., and preferably at from 10° to 50° C., to the intermediate product which has not been isolated.

In the formula (XXI), $R^{13}$ denotes a radical which is bonded to CO via carbon and which does not contain a hydrogen atom on the α-carbon atom and in particular denotes a tertiary alkyl group with 4 to 12 carbon atoms, an α-alkyl-substituted vinyl group with 3 to 8 carbon atoms, an alkynyl group with 2 to 8 carbon atoms, an α-substituted cycloalkyl group with 3 to 6 ring carbon atoms, or an aryl group, preferably phenyl or naphthyl, which is optionally substituted by halogen, $C_1$-$C_4$-alkyl, $C_1$-$C_4$-alkoxy, $CF_3$ or $NO_2$, or denotes a 5-membered or 6-membered heterocyclic radical which contains oxygen, sulphur and/or nitrogen in the ring and can also contain fused carbocyclic or aditional heterocyclic rings.

(c) Compounds of the formula (XVII) can also be obtained by subjecting the cyclic reaction products obtained from the compound of the formula (II) and aliphatic, araliphatic or cycloaliphatic carboxylic acid amides which contain at least one hydrogen atom on the carbon atom in the α-position relative to the carbonyl group, of the formula (XXIII), to hydrolysis.

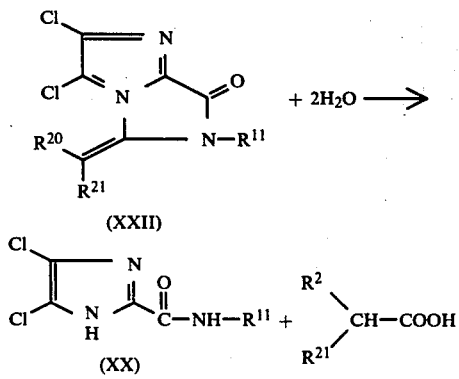

In formula (XXII), $R^{20}$ and $R^{21}$ each denote hydrogen, a $C_1$-$C_{12}$-alkyl radical or an aryl radical, or $R^{20}$ and $R^{21}$ conjointly denote a tetramethylene or pentamethylene radical.

With the reaction product obtained from the compound of the formula (II) and acetic acid ethylamide, the reaction takes, for example, the following course:

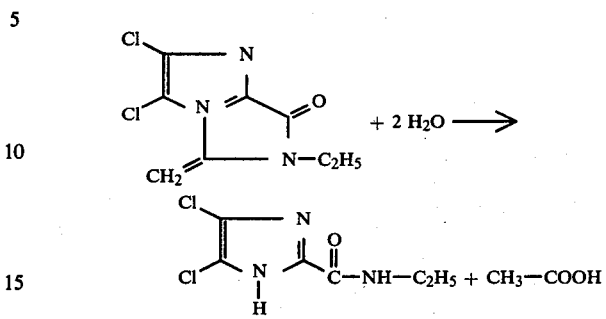

The hydrolysis reaction can be carried out with concentrated mineral acids, for example concentrated sulphuric acid, phosphoric acid or hydrochloric acid, or with dilute mineral acids, for example 3 to 15% strength hydrochloric acid or 3 to 45% strength sulphuric acid, or with organic acids, such as formic acid or oxalic acid. The reaction temperatures are from 0° to 150° C. and preferably from 20° to 100° C.

The cyclic precursors corresponding to formula (XXII) can be prepared in a simple manner from the compound of the formula (II) by reaction with carboxylic acid amides.

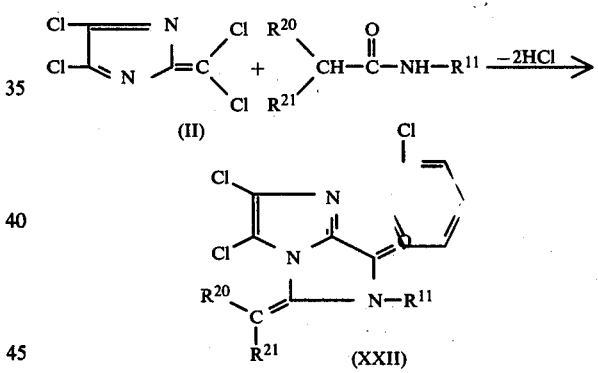

Suitable carboxylic acid amides are all those which are derived from primary amines and, in particular, from aliphatic, araliphatic, cycloaliphatic and aromatic amines. The carboxylic acid part of these carboxylic acid amides must contain at least one hydrogen atom on the carbon atom which is in the α-position relative to the carbonyl group. Thus, for example, suitable reactants are the amides of acetic acid, propionic acid, butyric acid, isobutyric acid, phenylacetic acid and cyclohexanecarboxylic acid.

At least equimolar amounts of the reactants are employed but the carboxylic acid amide can also be used in excess as the reaction medium. The reactions can be carried out in inert diluents but are preferably carried out without a solvent. The reaction temperatures are from 0° to 150° C. and preferably from 20° to 100° C.

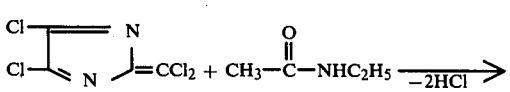

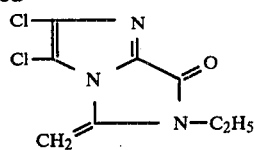

This reaction can also be carried out with those compounds in which the carboxylic acid radical and the amine radical are bonded together to form a ring, that is to say with lactams.

In these cases, carboxylic acid amides of 4,5-dichloroimidazole-2-carboxylic acid, of the formula (XXIV), in which the alkyl radical of the amide group is substituted by a carboxyl group, are obtained after hydrolysis of the intermediate products (XXIII), thus:

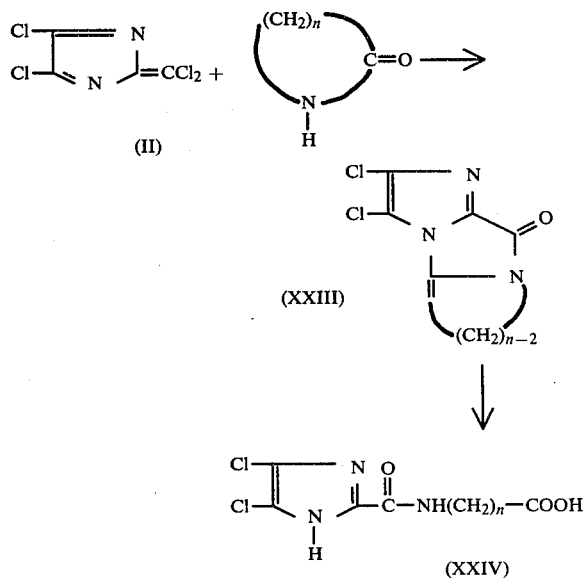

in which n = 3, 4 or 5.

Examples of lactams which can be used are pyrrolidone, valerolactam and caprolactam. The reaction conditions correspond to those described above. (d) Compounds of the formula (XVII) can also be obtained by subjecting 4,5-dichloro-imidazol-2-oyl-ureas of the formula (XXV) to scission. This scission can be effected by the action of heat or hydrolytically.

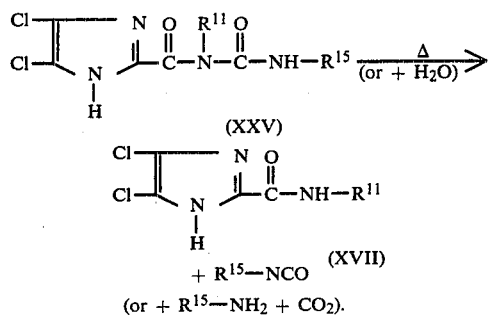

With 4,5-dichloro-imidazoloyl-1,3-dimethyl-urea the reaction takes, for example, the following course:

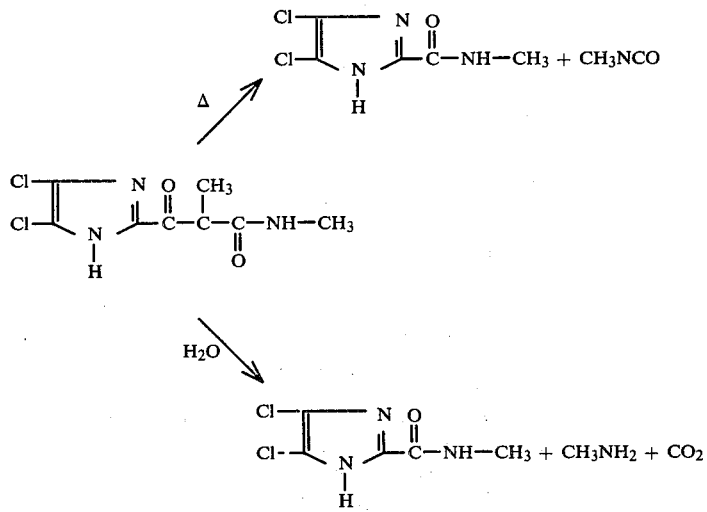

Scission by the action of heat can be effected in the melt without a diluent, or in solvents which have a sufficiently high boiling point, for example chlorobenzene, dichlorobenzene, mesitylene or tetralin. The reaction temperatures are from 100° to 250° C.

The hydrolysis reaction is preferably carried out with concentrated mineral acids, for example concentrated sulphuric acid or phosphoric acid, or with concentrated formic acid. The reaction temperature is from 50° to 150° C.

The 4,5-dichloro-imidazoloyl-ureas corresponding to the formula (XXV) or (XXVI)), which are required as precursors, are obtained from the compounds of the formula (II) and (III) by reaction with urea or, respectively, with monosubstituted or 1,3-disubstituted ureas. With monosubstituted ureas the reaction takes, for example, the following course:

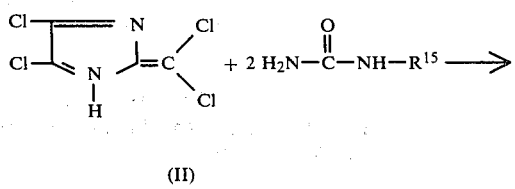

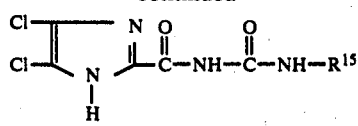

(XXVI)

+ (R$^{15}$—NHCN) + 2 HCl and with 1,3-disubstituted ureas takes the following course:

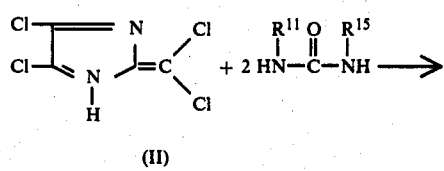

(II)

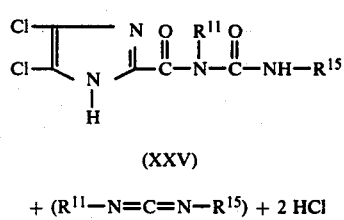

(XXV)

+ (R$^{11}$—N=C=N—R$^{15}$) + 2 HCl

The preparation is carried out by reacting the compounds of the formula (II) or (III) with at least twice the molar amount of the corresponding urea. This reaction can be carried out without a solvent or in inert organic solvents, such as, for example, dioxane, or also in water. The reaction temperatures are from 0° to 120° C. and preferably from 20° to 100° C.

In formulae (XXVI) and (XXVII), R$^{15}$ has the meaning already defined above. Preferably, R$^{15}$ repesents hydrogen or an alkyl radical with 1 to 12 carbon atoms or an alkenyl radical with 3 to 8 carbon atoms, which can be substituted by C$_1$–C$_4$-alkoxy, phenyl (which is optionally substituted by halogen or C$_1$–C$_4$-alkyl), cyclopentyl or cyclohexyl, or represents a phenyl radical (which is optionally substituted by halogen, C$_1$–C$_4$-alkyl, CF$_3$, C$_1$–C$_4$-alkoxy, C$_1$–C$_4$-alkylmercapto or NO$_2$).

(e) Compounds of the formula (XVII) can also be obtained by reacting 4,5-dichloro-imidazole-2-thiocarboxylic acid S-alkyl esters (corresponding to formula (VII)) or 4,5-dichloro-imidazole-carboxylic acid aryl esters (corresponding to formula (VI)) with ammonia or primary or secondary amines:

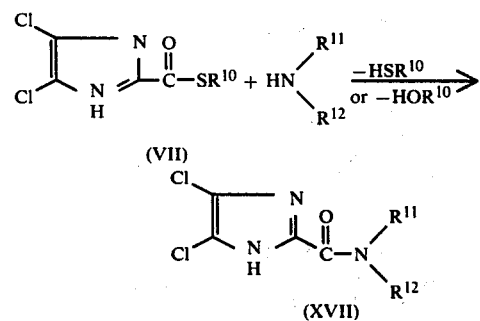

(XVII)

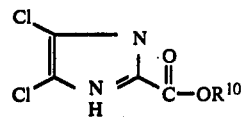

(VI)

With 4,5-dichloro-imidazole-2-thio-carboxylic acid S-methyl ester, or 4,5-dichloro-imidazole-2-carboxylic acid phenyl ester, and dimethylamine, the reaction takes, for example, the following course:

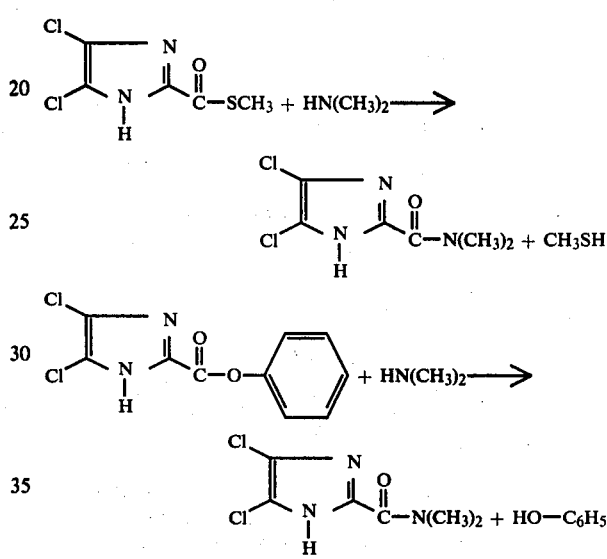

The reactions are preferably carried out in solvents. Suitable solvents are water, alcohols, open-chain and cyclic ethers, ketones, aliphatic and aromatic hydrocarbons, dimethylformamide, dimethylsulphoxide and the like. Suitable 4,5-dichloro-imidazole-2-thiocarboxylic acid S-alkyl esters are the alkyl esters and the benzyl esters and suitable 4,5-dichloro-imidazole-carboxylic acid aryl esters are esters containing any desired aryl ester radicals. Since the phenol part of these compounds is removed again, the unsubstituted phenyl ester is preferably used. The primary or secondary amine is employed in at least the equimolar amount but it can be advantageous (for example in the case of readily volatile amines) to add an excess of up to a further mole. The reaction temperatures are from −20° to +120° C. and preferably from 20° to 75° C. The preparation of the 4,5-dichloro-imidazole-2-thiocarboxylic acid alkyl esters and of the 4,5-dichloro-imidazole-2-carboxylic acid aryl esters has already been described hereinabove.

(f) Compounds of the formula (XVII) can also be obtained by reacting the dimeric ketene of 4,5-dichloroimidazole-2-carboxylic acid, of the formula (IV), with ammonia or primary or secondary amines.

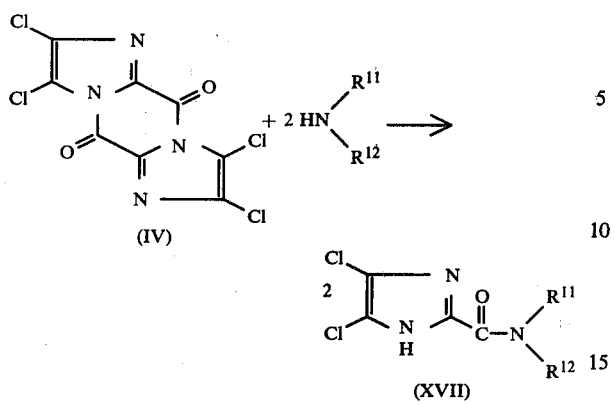

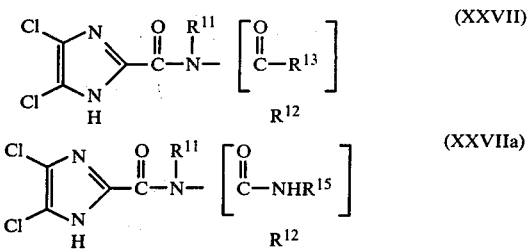

With dimethylamine the reaction takes, for example, the following course:

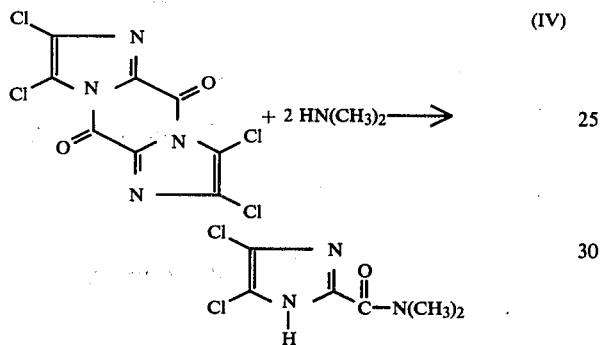

The reactions are preferably carried out in solvents. Examples of suitable solvents are hydrocarbons, alcohols, open-chain and cyclic ethers, ketones, dimethylformamide and dimethylsulphoxide.

The reaction temperatures are from −10° to +150° C. and the reaction is preferably carried out at from 0° to 100° C.

In the formulae (XVII), (XIX), (XX), (XXI), (XXII) and (XXV), $R^{11}$ and $R^{12}$ have the meaning already defined above. In these formulae, $R^{11}$ and $R^{12}$ preferably represent hydrogen or an alkyl radical with 1 to 12 carbon atoms or an alkenyl radical with 3 to 8 carbon atoms, which can be substituted by halogen (fluorine, chlorine or bromine), hydroxyl, $C_1$–$C_4$-alkyl, O-aryl (optionally substituted in the aryl radical by $C_1$–$C_4$-alkyl, halogen or $C_1$–$C_4$-alkoxy), $C_1$–$C_4$-alkylmercapto, S-benzyl, S-aryl (optionally substituted in the aryl radical by chlorine or methyl), carboxyl, carboxamide, cyano, aryl (preferably phenyl and naphthyl which are optionally substituted by halogen, methyl, $CF_3$, $C_1$–$C_4$-alkoxy or $NO_2$) or cycloalkyl with 5 or 6 ring carbon atoms or by a 5-membered or 6-membered heterocyclic radical which contains oxygen, sulphur and/or nitrogen as hetero-atoms; or represent an alkynyl radical with 3 to 12 carbon atoms, which is optionally substituted by (possibly substituted) phenyl or $C_5$–$C_6$-cycloalkyl; or represent a cycloalkyl radical with 4 to 8 ring carbon atoms, which is optionally substituted by $C_1$–$C_4$-alkyl and can also contain fused carbocyclic rings; or represent a 5-membered or 6-membered heterocyclic radical which contains oxygen, sulphur and/or nitrogen as hetero-atoms and can also contain fused carbocyclic or heterocyclic rings; or $R^{11}$ and $R^{12}$ can also form, conjointly with the nitrogen atom which links them, a 3-membered to 7-membered ring which in addition to this nitrogen atom can also contain yet further hetero-atoms, such as oxygen, sulphur or nitrogen, as well as fused carbocyclic rings.

The preparation of compounds of the general formula (XXVII) and (XXVIIa)

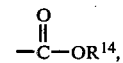

in which $R^{13}$ denotes hydrogen or an optionally substituted organic radical and $R^{15}$ denotes alkyl or aryl, has already been described previously (compare the processes for the preparation of 4,5-dichloro-imidazole-2-carboxylic acid amides, formulae (XIX), (XXI), (XXV) and (XXVI)).

Those compounds in which $R^{12}$ denotes a group $$-\overset{\overset{O}{\|}}{C}-OR^{14},$$

in which $R^{14}$ denotes alkyl or aryl, can also be prepared in an analogous manner. For this purpose, carbamic acid esters are reacted with the compound of the formula (II) or (III).

If N-monosubstituted carbamic acid esters are employed, compounds of the amide-chloride type are obtained in the first stage and these are then hydrolyzed.

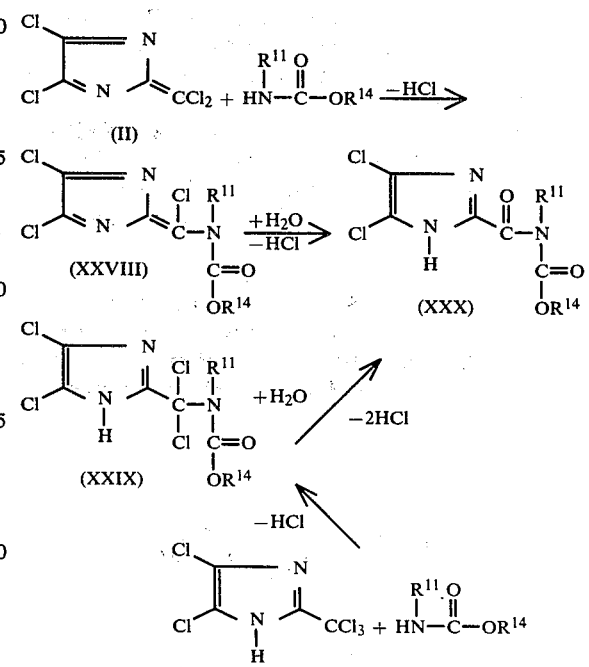

When N-methyl-carbamic acid phenyl ester is used as the starting material, the reaction proceeds, for example, in accordance with the following equation:

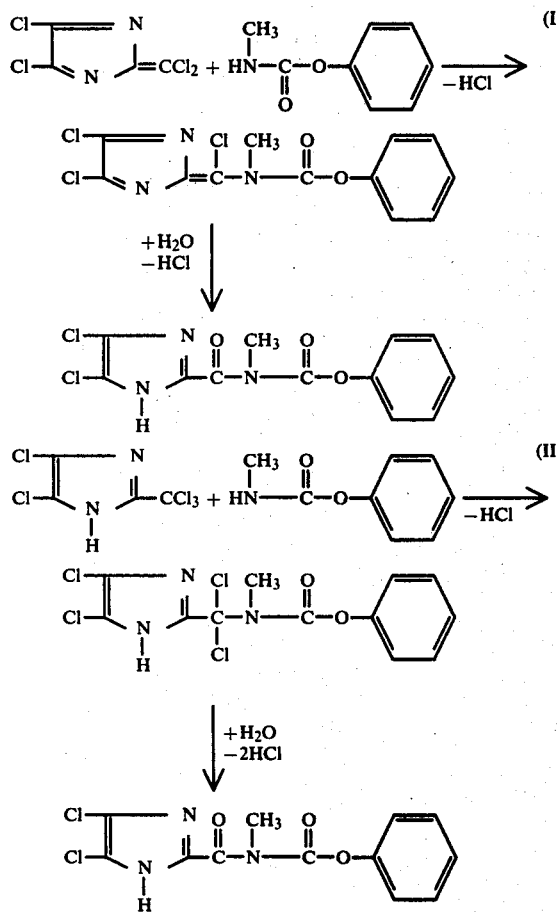

The first stage of the reaction is carried out in aprotic solvents, preferably cyclic ethers, such as dioxane or tetrahydrofuran, at temperatures between 50° and 150° C. The subsequent second stage is carried out with at least the equimolar amount of water; and diluents, such as alcohols, ketones or cyclic ethers, can be present. The hydrogen chloride which is liberated during the hydrolysis reaction can be bound by the addition of equimolar amounts of a base, for example alkali metal oxides, hydroxides or carbonates and alkaline earth metal oxides, hydroxides or carbonates or tertiary amines, but as a rule this is not necessary. The reaction temperatures are from 0° to 100° C. and preferably from 20° to 70° C.

If N-unsubstituted carbamic acid esters are employed, the course of the reaction can be so controlled that N-(4,5-dichloro-imidazol-2-oyl)-carbamic acid esters (XXXI) are formed in a one-stage reaction. In this case, a second mole of the carbamic acid ester serves as the "hydrolyzing" agent for the intermediate products corresponding to formula (XXIX).

When carbamic acid ethyl ester is used as the starting material, the reaction proceeds as follows:

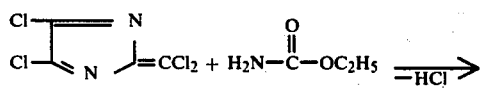

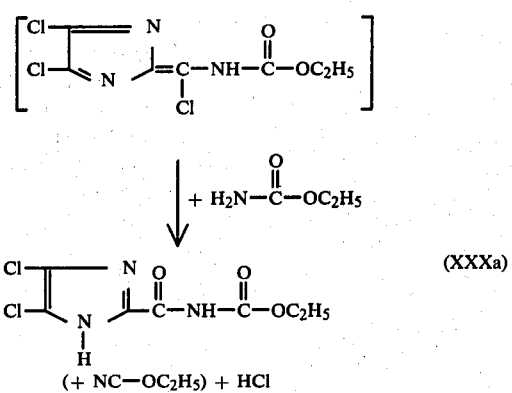

In accordance with this equation, at least two moles and preferably 2-3 moles of a carbamic acid ester are allowed to act on the compound of the formula (II). Cyclic ethers, such as dioxane and tetrahydrofuran, are preferred as the reaction medium. The reaction temperatures are from 20° C. up to the boiling point of the particular solvent.

For formula (XXX), $R^{11}$ has already been defined more precisely above. The radical $R^{14}$ denotes an alkyl radical with 1 to 12 carbon atoms, an alkenyl radical with 3 to 12 carbon atoms or an alkynyl radical with 3 to 12 carbon atoms, each of which can also be substituted by halogen, $C_1$–$C_4$-alkoxy, aryl, preferably phenyl (optionally substituted by halogen or $C_1$–$C_4$-alkyl) or cyclohexyl, and also denotes a cycloalkyl radical with 5 to 6 ring carbon atoms or an aryl radical, preferably phenyl and naphthyl, which is optionally substituted by halogen, $C_1$–$C_4$-alkyl, $CF_3$, $C_1$–$C_4$-alkoxy, $C_1$–$C_4$-alkylmercapto, $NO_2$ or cyano.

The procedure employed in order to prepare compounds of the formula (XVII) in which $R^{11}$ denotes hydrogen and $R^{12}$ denotes a sulphonyl group $SO_2$—$R^8$ (formula (XXXI)) is that 4,5-dichloro-2-dichloromethylene-imidazole (II) is reacted with an alkali metal salt of an N-unsubstituted sulphonamide $R^8$—$SO_2$—$NH_2$ and water.

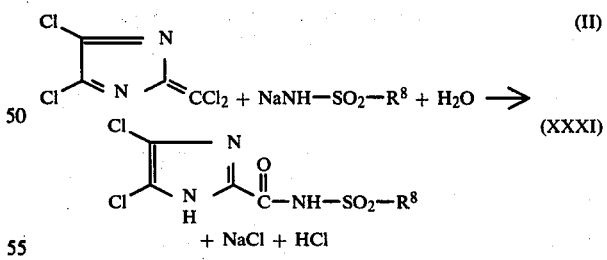

The reactions are carried out in water alone, or in the simultaneous presence of a water-miscible solvent, such as acetone, dioxane or tetrahydrofuran, and optionally in the presence of an acid-binding agent, such as an alkali metal oxide, hydroxide or carbonate, an alkaline earth metal oxide, hydroxide or carbonate or a tertiary amine. The reaction temperature is from 0° to 100° C. and preferably from 20° to 100° C.

$R^8$ has the meaning already indicated above and preferably represents an alkyl group with 1–4 carbon atoms which is optionally substituted by chlorine or fluorine, or represents phenyl which is optionally substituted by halogen, methyl, $C_1$–$C_4$-alkoxy, $CF_3$ or nitro, or represents a secondary amino group.

A number of processes, which have been indicated for the preparation of 4,5-dichloro-imidazole-2-carboxylic acid amides of the formula (XVII), can be used to prepare the compounds of the formula (I) in which X and Y conjointly denote an oxygen atom and Z denotes an optionally substituted hydroxylamino group (formula (XXXII)). For example, corresponding to process (e), the phenyl ester or S-methyl thioester of 4,5-dichloro-imidazole-2-carboxylic acid can be reacted with hydroxylamine or its O-alkyl or N,O-dialkyl derivatives:

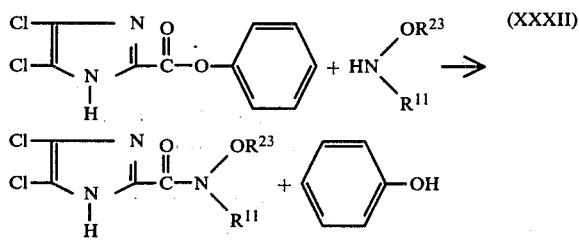

With hydroxylamine itself, 4,5-dichloro-imidazole-2-hydroxamic acid is, for example, obtained in this way. The reaction conditions are the same as those described in process (e) for corresponding carboxylic acid amides.

In formula (XXXII), $R^{11}$ and $R^{23}$ preferably denote hydrogen or lower ($C_1$–$C_4$)-alkyl radicals, a benzyl radical or the cyclohexyl radical.

Alkyl and aralkyl radicals corresponding to $R^{11}$ and $R^{23}$ can also be introduced into the molecule subsequently by reacting 4,5-dichloro-imidazole-2-hydroxamic acid ($R^{11}$ and $R^{23}$=H) with alkylating agents by known methods, preferably in an alkaline medium.

A number of the processes indicated for the preparation of 4,5-dichloro-imidazole-2-carboxylic acid amides can also be employed for the preparation of the compounds of the formula (I) in which X and Y conjointly denote an oxygen atom and Z denotes an optionally substituted hydrazino group (formula (XXXIII)). The process in which a 4,5-dichloroimidazole-2-carboxylic acid alkyl ester is reacted with a corresponding hydrazine has proved particularly suitable:

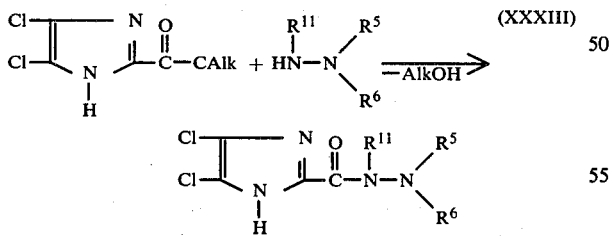

With 4,5-dichloro-imidazole-2-carboxylic acid methyl ester and unsubstituted hydrazine (as the hydrate), for example, 4,5-dichloro-imidazole-2-carboxylic acid hydrazide (XXXIIIa) is obtained:

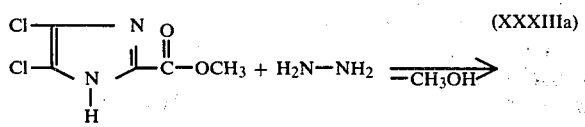

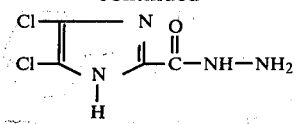

As a rule the reaction is carried out by reacting a 4,5-dichloro-imidazole-2-carboxylic acid alkyl ester in a solvent with at least the equimolar amount of hydrazine or of a substituted hydrazine. Suitable solvents are aliphatic and aromatic hydrocarbons, open-chain and cyclic ethers, alcohols, and water can also be present. Because the hydrazines are strongly basic, the reaction products are obtained in the form of their hydrazinium salts (the salt is formed on the acidic ring-nitrogen of the imidazole radical) when more than the equimolar amount of the particular hydrazine is used. The free hydrazides can be obtained from these salts by acidification. The reaction temperatures are from 0° to 120° C. and preferably from 20° to 100° C.

In formula (XXXIII), $R^{11}$, $R^5$ and $R^6$ denote hydrogen or an alkyl radical with 1 to 4 carbon atoms, a benzyl radical which is optionally substituted by halogen or methyl, or a phenyl radical which is optionally substituted by halogen, nitro, methyl, $C_1$–$C_4$-alkoxy or $CF_3$.

$R^5$ and $R^6$, conjointly with the nitrogen atom which links them and, optionally, further hetero-atoms such as oxygen, sulphur or nitrogen, can be joined to form a 5-membered or 6-membered ring.

The carboxylic acid hydrazides of the formula (XXXIII) in which at least one of $R^5$ and $R^6$ denotes a hydrogen atom can also be subjected to further reactions in accordance with known processes. Several of these possible reactions are illustrated in the text which follows, using 4,5-dichloro-imidazole-2-carboxylic acid hydrazide as an example.

(a') Reaction with aldehydes or ketones, preferably in organic solvents and if appropriate with acid catalysis:

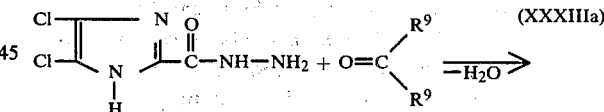

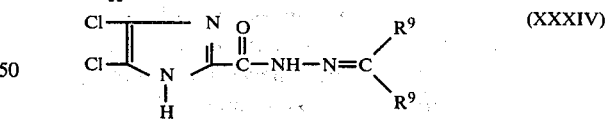

In formula (XXXIV), the $R^9$ moieties denote $C_1$–$C_{12}$-alkyl radicals, which are optionally substituted by OH, $C_1$–$C_4$-alkoxy, COOH or COO—$C_1$–$C_4$-alkyl, or cycloalkyl radicals with 5 or 6 carbon atoms in the ring, aralkyl radicals which have 1–4 carbon atoms in the alkyl chain and are optionally substituted in the aryl radical by halogen, nitro, $C_1$–$C_4$-alkyl or $C_1$–$C_4$-alkoxy, or aryl radicals, preferably phenyl or naphthyl, which are optionally substituted by OH-halogen, nitro, $C_1$–$C_4$-alkyl, $C_1$–$C_4$-alkyl, $C_1$–$C_4$-alkylmercapto or $CF_3$, or heterocyclic radicals with 5 or 6 ring members with oxygen, sulphur or nitrogen in the ring and it is possible for the two radicals $R^9$ to be joined together to form a carbocyclic or heterocyclic ring. One of the radicals $R^9$ can also denote hydrogen.

(b') Reaction with carboxylic acid chlorides in the presence of acid-binding agents in water or organic solvents or with caboxylic acid anhydrides in the presence or absence of inert solvents:

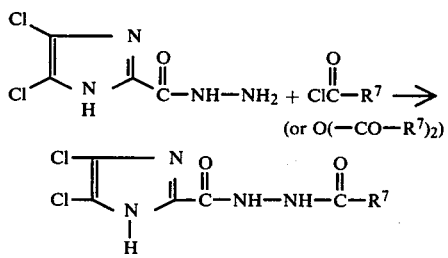
(XXXVI)

(XXXV)

In formula (XXXV), $R^7$ preferably denotes hydrogen or an alkyl radical with 1-12 carbon atoms or an alkenyl radical with 2-8 carbon atoms, which are optionally substituted by halogen, $C_1$-$C_4$-alkoxy, O-aryl, especially phenoxy which is optionally substituted by halogen, methyl or nitro, or $C_1$-$C_4$-alkylmercapto, S-aryl (optionally substituted by chlorine or methyl), or phenyl (optionally substituted by halogen or $C_1$-$C_4$-alkyl; or denotes an alkynyl radical with 2 to 8 carbon atoms, a cycloalkyl radical with 3 to 6 ring carbon atoms, an aryl radical, preferably phenyl and naphthyl, which is optionally substituted by halogen, $C_1$-$C_4$-alkoxy, $C_1$-$C_4$-alkylmercapto, $C_1$-$C_4$-alkyl, $CF_3$ or $NO_2$, or a 5-membered or 6-membered heterocyclic radical which contains oxygen, sulphur and/or nitrogen in the ring and can also contain fused carbocyclic or additional heterocyclic rings.

(c') Reaction with (thio)carbonic acid ester-chlorides in organic solvents in the presence of acid-binding agents:

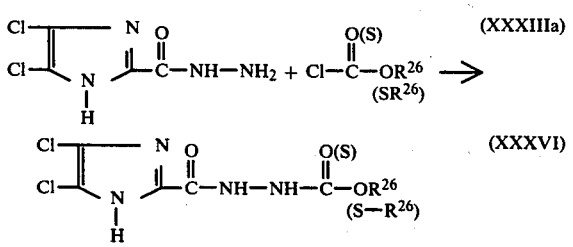
(XXXIIIa)

(XXXVI)

In formula (XXXVI), $R^{26}$ preferably denotes an alkyl radical with 1 to 12 carbon atoms, an alkenyl radical with 3 to 12 carbon atoms or an alkynyl radical with 3 to 12 carbon atoms, which can be optionally substituted by halogen, $C_1$-$C_4$-alkoxy, phenyl (optionally substituted by $C_1$-$C_4$-alkyl or halogen), cyclohexyl, furyl, thienyl or pyridyl, or denotes a cycloalkyl radical with 5 to 6 ring carbon atoms or an aryl radical, preferably phenyl or naphthyl, which is optionally substituted by halogen, $C_1$-$C_4$-alkyl, $C_1$-$C_4$-alkoxy or nitro.

(d') Reaction with (thio)carbamic acid chlorides, preferably in organic solvents in the presence of acid-binding agents:

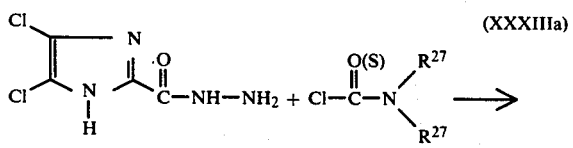
(XXXIIIa)

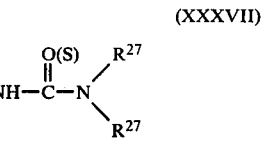
(XXXVII)

or with isocyanates or isothiocyanates, preferably in organic solvents:

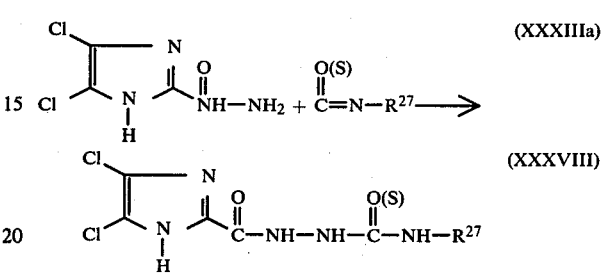
(XXXIIIa)

(XXXVIII)

In formulae (XXXVII) and (XXXVIII), $R^{27}$ denotes hydrogen or an alkyl radical with 1-12 carbon atoms or an alkenyl radical with 3-8 carbon atoms, which can be substituted by halogen, $C_1$-$C_4$-alkoxy or phenyl (optionally substituted by halogen or alkyl ($C_1$-$C_4$)), or denotes a cycloalkyl radical with 5 or 6 ring carbon atoms or a phenyl radical which is optionally substituted by halogen, $C_1$-$C_4$-alkyl, $C_1$-$C_4$-alkoxy, $C_1$-$C_4$-alkylmercapto, $CF_3$ or $NO_2$.

(e') Reaction with sulphonic acid chlorides and sulphamic acid chlorides, preferably in organic solvents and in the presence of acid-binding agents:

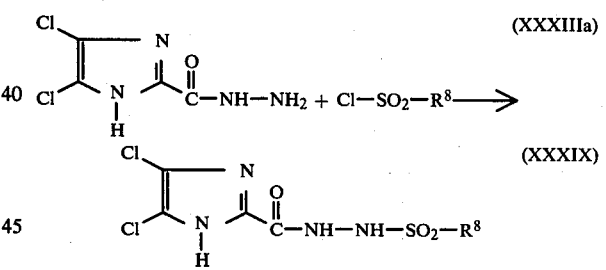
(XXXIIIa)

(XXXIX)

In formula (XXXIX), $R^8$ denotes an alkyl radical which has 1 to 12 carbon atoms and is optionally substituted by chlorine or fluorine, or denotes phenyl or naphthyl which are optionally substituted by chlorine, $C_1$-$C_4$-alkyl, $C_1$-$C_4$-alkoxy, $CF_3$ or $NO_2$); or $R^8$ denotes a secondary amino group.

The compound of the formula (I) in which X and Y conjointly denote an oxygen atom and Z denotes an azide group, that is to say 4,5-dichloro-imidazole-2-carboxylic acid azide (formula (XL)), can be prepared by allowing nitrous acid or one of its lower alkyl esters to act on 4,5-dichloroimidazole-2-carboxylic acid hydrazide (XXXIIIa). With nitrous acid itself, the reaction takes, for example, the following course:

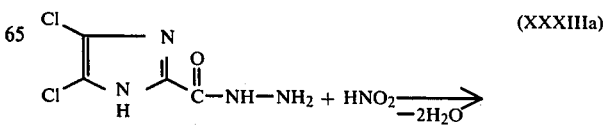
(XXXIIIa)

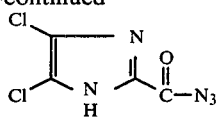

The reaction is carried out in water or lower alcohols at temperatures between −20° and +50° C. and preferably at 0°–20° C.

Alternatively, the compounds (XL) can be prepared by reacting 4,5-dichloro-2-dichloromethylene-imidazole (II) with aqueous solutions of salts of hydrazoic acid:

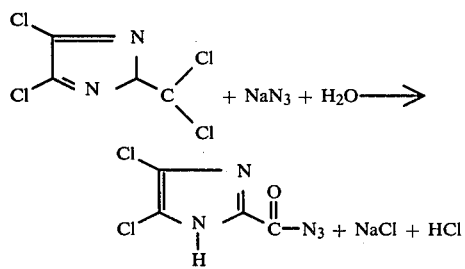

The reaction can be carried out in water alone or in the simultaneous presence of a water-miscible solvent, for example dioxane, tetrahydrofuran or acetone. The reaction temperature is from 0° to 100° C. amd preferably from 0° to 50° C.

In order to prepare the compounds of the formula (I) in which X and Y conjointly denote a sulphur atom and Z denotes a group S—$R^{10}$ (formula XLI)

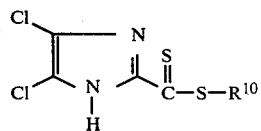

in which
$R^{10}$ preferably represents an alkyl radical with 1 to 6 carbon atoms, an alkenyl radical or an alkynyl radical with 3-5 carbon atoms, a cyclohexyl radical or a benzyl radical which is optionally substituted by chlorine or methyl, the compound (II) or (III) is first reacted with a salt of hydrogen sulphide to give a salt of 4,5-dichloroimidazole-2-dithiocarboxylic acid (XLII) and this is then allowed to react with an alkylating agent. When sodium hydrogen sulphide and methyl iodide are used as the reactants, the reaction takes, for example, the following course:

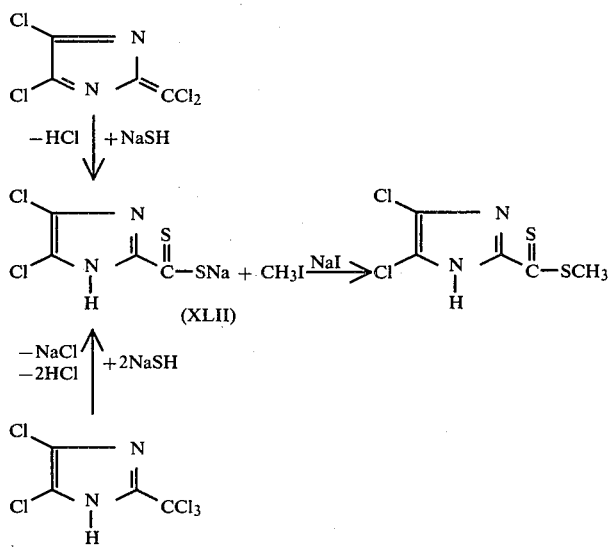

For the first stage of the reaction, alkali metal hydrogen sulphides or alkaline earth metal hydrogen sulphides are preferably used. The solvents used are water or lower alcohols, or mixtures of these. The reaction temperatures are from −20° to +100° C. and preferably from 0° to 70° C. The salts corresponding to formula (XLII) can be isolated by evaporating the solvent. As a rule, however, they are converted, without purification, as described above, in a second stage with an alkylating agent into a dithiocarboxylic acid ester, corresponding to formula (XLI).

The alkylating agents used are the customary known alkyl halides, alkenyl halides, alkynyl halides, cycloalkyl halides or aralkyl halides or appropriate dialkyl sulphates or sulphonic acid alkyl esters. In general, the reaction is carried out in the same reaction medium in which the salts of the formula (XLII) are produced, preferably in lower alcohols or their mixtures with water, optionally after previously separating off the alkali metal chloride or alkaline earth metal chloride formed during the reaction leading to (XLI). The reaction temperatures are from 0° to 100° C.

In order to prepare the compound of the formula (I) in which X and Y conjointly denote a sulphur atom and Z denotes the amino group (formula (XLIII)), 4,5-dichloro-imidazole-2-carboxylic acid nitrile (L) is reacted with hydrogen sulphide.

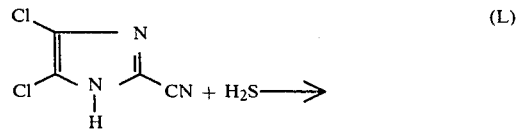

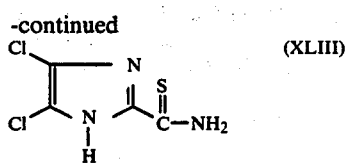

All the processes known in the literature for the conversion of a carboxylic acid nitrile into a corresponding thioamide can be used for this purpose. For example, the procedure can be that the nitrile (L) is treated, in pyridine as the solvent and in the presence of an equimolar amount of a strongly basic amine (for example triethylamine), at from 20° to 50° C. with excess hydrogen sulphide.

Compounds of the formula (I) in which X and Y conjointly denote a sulphur atom and Z denotes a substituted amino group or an optionally substituted hydrazino group or hydroxylamino group (formula (XLIV)) can be obtained from the 4,5-dichloro-imidazole-2-dithiocarboxylic acid alkyl esters corresponding to formula (VIII) by reaction with primary or secondary amines, with hydroxylamines or with hydrazines.

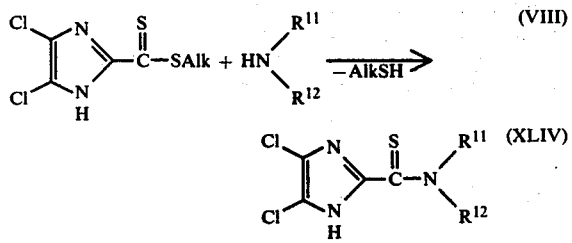

In formula (XLIV), $R^{11}$ and $R^{12}$ denote the radicals indicated in the case of the compounds of the formulae (XVII), (XXXII) and (XXXIII). The reactions are preferably carried out using an equimolar ratio. The solvents used are hydrocarbons, alcohols, open-chain and cyclic ethers and also water, or mixtures of the latter and the said organic solvents. The reaction temperatures are from 0° to 150° C. and preferably from 15° to 100° C.

Compounds of the formula (I) in which X and Y conjointly represent an imino group and Z represents an alkoxy group are 4,5-dichloro-imidazole-2-imino-carboxylic acid esters of the formula (XLV) which, like customary imino-carboxylic acid esters, are stable only in the form of their salts. The latter are obtained by the action of alcohols on 4,5-dichloro-imidazole-2-carboxylic acid nitrile of the formula (L) in the presence of strong mineral acids:

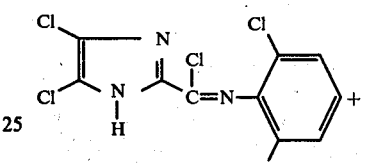

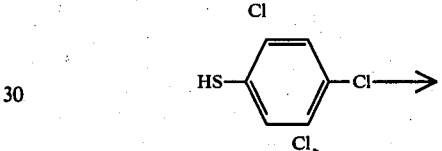

The alcohols used are saturated or unsaturated aliphatic, cycloaliphatic or araliphatic alcohols, and hydrogen halide acids, preferably hydrochloride acid, are used as the mineral acid.

The reactions can be carried out in the particular alcohol as the solvent or can be carried out with stoichiometric amounts of the alcohol in solvents such as hydrocarbons or open-chain or cyclic ethers. The reaction temperatures are from $-20°$ to $100°$ C. and preferably from $0°-50°$ C.

Compounds of the formula (I) in which X and Y conjointly denote a substituted imino group are obtained by reacting an imide-chloride of the formula (XIV) with a compound of the general formula Z—H.

If 4,5-dichloro-imidazole-2-carboxylic acid N-(2,6-dichlorophenyl)-imide-chloride is used as the imide-chloride of the formula (XIV) and 4-chloro-thiophenyl is used as the compound of the formula Z—H, the course of the reaction can be represented as follows:

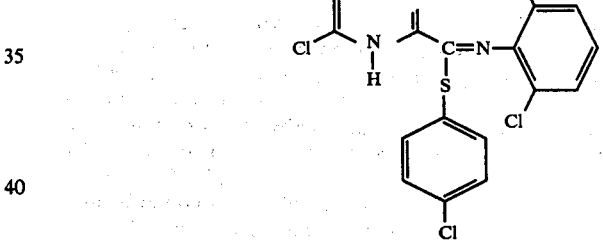

The reaction can be carried out using suitable diluents. Water, in particular, can be used as a suitable diluent.

The reaction is also carried out in the presence of suitable acid-binders; examples of acid-binders which can be used are alkali metal hydroxides, for example sodium hydroxide or potassium hydroxide.

The reaction temperatures can vary within a wide range. In general, the reaction is carried out at between 10° and 100° C.

The reactants are generally employed in equimolar amounts, except for cases in which the compound Z—H serves simultaneously as the acid-binder, by virtue of its basic properties. In these cases it is possible to carry out the reaction using an excess of a compound of the formula Z—H.

In general, the reaction is carried out under normal pressure.

Compounds of the formula (I) in which X and Y conjointly denote a substituted imino group and Z denotes a monosubstituted amino group (formula (XLVI)) are prepared by allowing primary amines to act on the compound (II) or (III):

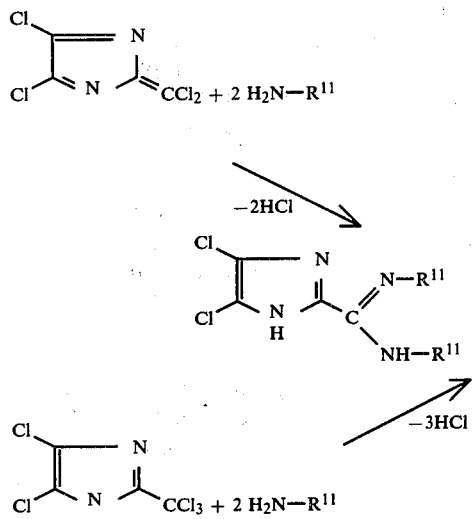

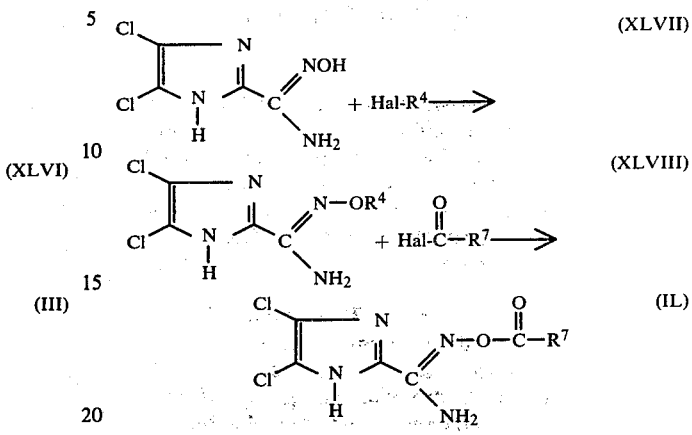

In formula (XLVI), $R^{11}$ has the meaning already defined above but does not denote hydrogen.

During the reaction, two moles (from (II)) or three moles (from (III)) of hydrogen chloride must be bound. This can be effected by using four or five moles of the amine employed for the reaction in place of the two moles which are stoichiometrically necessary. However, it is also possible to employ the corresponding amount of an alkali metal carbonate, alkaline earth metal carbonate or tertiary amine as an acid-binding agent. As a rule, the reactions are carried out in solvents. Suitable solvents are hydrocarbons, alcohols, open-chain and cyclic ethers, as well as water. If water and alcohols are used as the solvent, it is advisable, in order to avoid side reactions, to proceed in such a way that an excess of the amine is always present during the reaction. The reaction temperatures are from $-20°$ to $+150°$ C. and preferably from $0°$ to $100°$ C.

The compound of the formula (I) in which X and Y conjointly denote a hydroximino group and Z denotes an amino group, that is to say 4,5-dichloro-imidazole-2-carboxylic acid amide-oxime (formula XLVII)), is prepared by subjecting 4,5-dichloro-imidazole-2-carboxylic acid nitrile (L) to an addition reaction with hydroxylamine:

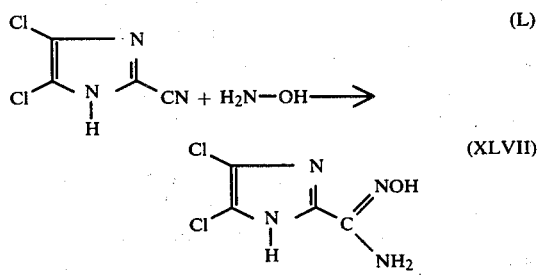

This reaction is preferably carried out in water or lower alcohols, or in mixtures of these. The hydroxylamine is employed in at least the equimolar amount. The reaction temperatures are from $0°$ to $100°$ C. and preferably from $15°$ to $75°$ C.

Derivatives on the —NOH or on the —NH$_2$ group of the amide-oxide radical can also be prepared from the compound (XLVII). Thus, for example, alkylation in an alkaline medium leads to O-alkyl-amide-oximes (XLVIII) and acylation, for example with carboxylic acid halides or halogenocarbonic acid derivatives, leads to O-acyl-amide-oximes (IL):

and in the formulae (XLVIII) and (IL) the radicals $R^4$ and $R^7$ have the meaning already indicated above.

The compound of the formula (I) in which X, Y and Z conjointly denote a nitrogen atom linked by a triple bond, that is to say 4,5-dichloro-imidazole-2-carboxylic acid nitrile of the formula (L), is prepared by allowing at least three or four moles of ammonia to act on the compound of the formula (II) or (III) respectively:

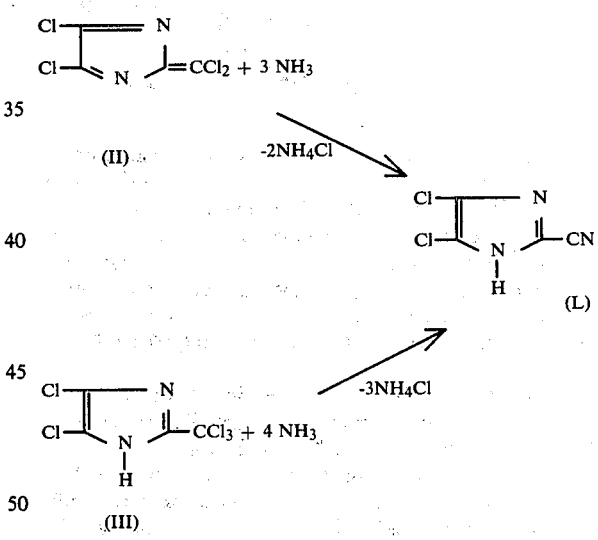

The compound of the formula (L) is advantageously obtained in good yield, without substantial side reactions, when ammonia is always in excess during the reaction, that is to say the procedure is preferably such that the compound of the formula (II) or (III) is introduced into previously charged ammonia.

Ammonia can itself serve as the solvent and this means that the reaction is carried out in liquid ammonia. Alternatively, solutions of ammonia in cyclic ethers, such as dioxane or tetrahydrofuran, or in lower alcohols or water or in mixtures of these, are used. When the reaction is carried out in lower alcohols, water or mixtures of these, reaction temperatures of from $-20°$ to $+50°$ C. and preferably from $0°$ to $25°$ C. are employed.

The nitrile of the formula (L) is obtained in the process in the form of its watersoluble ammonium salt and can be obtained in the free form from this salt by adding sufficient amounts of mineral acids.

Compounds of the formula (I) in which two or three of the radicals X, Y and Z are linked together via at least one hetero-atom in each case, preferably oxygen, sulphur or nitrogen, to form a 5-membered ring are prepared by allowing reactants which contain two hydrogen atoms, capable of substitution by acyl groups, in the 1,4-position relative to one another, to act on the compound of the formula (II) or (III).

Examples of compounds which can be prepared in this way are:

(a) Compounds which have a 5-membered ring and contain an oxygen atom and a nitrogen atom:

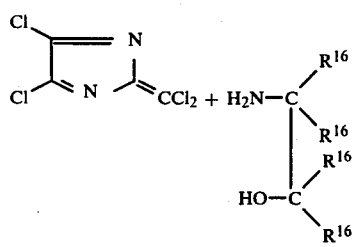 (II)

or

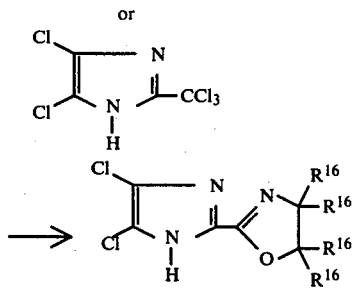 (III)

(LI)

$R^{16}$ in the 2-amino-alkanol preferably denotes $C_1$–$C_4$-alkyl or $C_1$–$C_4$-alkoxy or hydrogen.

(II) or (III) 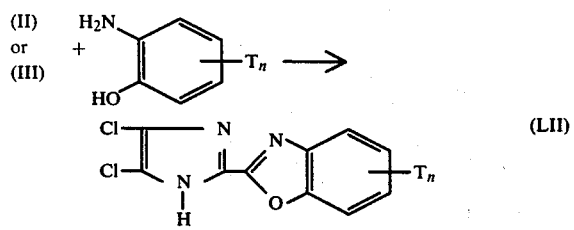 (LII)

In the 2-amino-phenol or in formula (LII), the T moieties denote identical or different radicals comprising halogen, $C_1$–$C_4$-alkyl, $C_1$–$C_4$-alkoxy, $NO_2$ or $CF_3$ and n denotes an integer from 1 to 4.

(b) Compounds which have a 5-membered ring and contain a sulphur atom and a nitrogen atom:

(II) or (III) 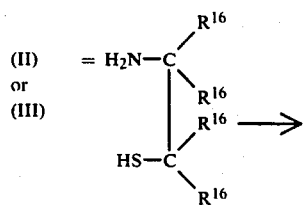

-continued

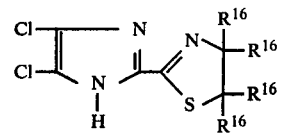

$R^{16}$ in the 2-mercapto-alkylamine has the preferred meaning indicated above.

(II) or (III) 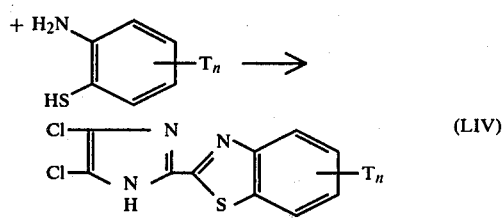 (LIV)

T and n in the 2-amino-thiophenol having the preferred meanings indicated above.

(c) Compounds which have a 5-membered ring and contain two nitrogen atoms:

(II) or (III) 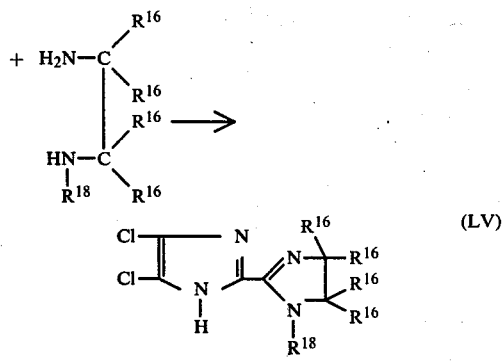 (LV)

In the 1,2-diamino-alkane,
  $R^{16}$ has the above-mentioned meaning, and
  $R^{18}$ denotes hydrogen, $C_1$–$C_6$-alkyl, $C_5$–$C_6$-cycloalkyl, benzyl or phenyl which is optionally substituted by chlorine, $C_1$–$C_4$-alkoxy, $C_1$–$C_4$-alkyl or $NO_2$.

(II) or (III) 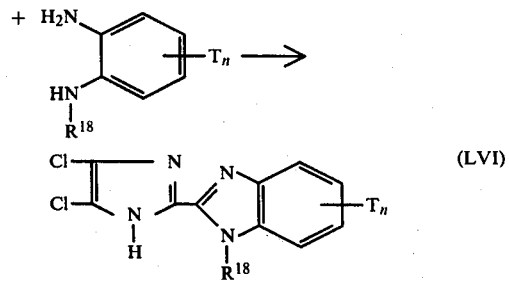 (LVI)

T and n in the 1,2-phenylene-diamine have the above-mentioned meanings.

(d) Compounds which have a 5-membered ring and contain an oxygen atom and two nitrogen atoms are prepared from carboxylic acid hydrazide, carbazic acid esters or thiocarbazic acid S-esters, thus

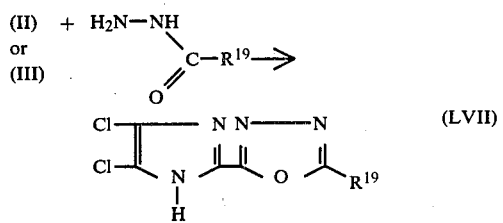

(e) Compounds which have a 5-membered ring and contain a sulphur atom and two nitrogen atoms are prepared from thiocarboxylic acid hydrazides, dithiocarbazic acid esters or thiosemicarbazides, thus

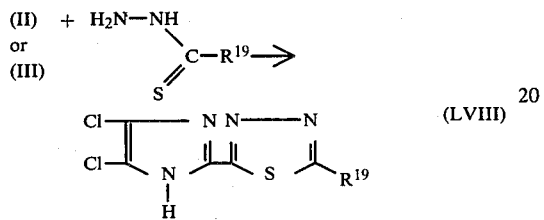

(f) Compounds which have a 5-membered ring and contain three nitrogen atoms are prepared from amidrazones, O-alkylsemicarbazides, S-alkyl-thiosemicarbazides, or aminoguanidines, thus:

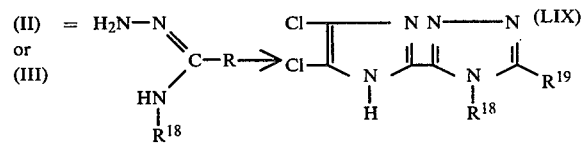

(g) The compounds (LX) are prepared from semicarbazides, thus:

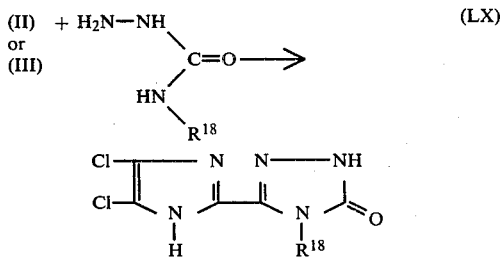

In the formulae (LVII), (LVIII), (LIX) and (LX), $R^{18}$ has the above-mentioned meaning and $R^{19}$ preferably denotes hydrogen or $C_1$-$C_{12}$-alkyl, which is optionally substituted by $C_1$-$C_4$-alkoxy, phenoxy (optionally substituted by methyl or or halogen), $C_1$-$C_4$-alkylmercapto, phenylmercapto (optionally substituted by methyl or halogen), or phenyl or naphthyl (which are optionally substituted by methyl, $C_1$-$C_4$-alkoxy or halogen); or denotes cycloalkyl with 5 or 6 ring carbon atoms, which is optionally substituted by $C_1$-$C_4$-alkyl; phenyl or naphthyl, which are optionally substituted by halogen, $C_1$-$C_4$-alkyl, $CF_3$, $C_1$-$C_4$-alkoxy, $C_1$-$C_4$-alkylmercapto or $NO_2$; a 5-membered or 6-membered heterocyclic radical which contains oxygen, sulphur and/or nitrogen as hetero-atoms and can also contain fused carbocyclic or additional heterocyclic rings; alkoxy with 1 to 12 carbon atoms; phenoxy, which is optionally substituted by halogen, $C_1$-$C_4$-alkyl, $CF_3$, $C_1$-$C_4$-alkoxy, $C_1$-$C_4$-alkylmercapto, $C_1$-$C_4$-alkylsulphonyl, $NO_2$ or CN; alkylmercapto, which is saturated or unsaturated, contains 1 to 12 carbon atoms and is optionally substituted by $C_1$-$C_4$-alkoxy or phenyl (optionally substituted by chlorine, nitro, methyl or methoxy); or amino, which is optionally substituted by $C_1$-$C_{12}$-alkyl, $C_5$-$C_6$-cycloalkyl, benzyl or phenyl (which is optionally substituted by halogen, $C_1$-$C_4$-alkyl, $CF_3$, $NO_2$, $C_1$-$C_4$-alkoxy or $C_1$-$C_4$-alkylmercapto.

The reactions (a) to (g) are carried out by reacting the compounds (II) or (III) with at least the equimolar amount of the indicated reactants. The addition of further substances can be dispensed with and, for example, the reaction components can be allowed to act on one another in the absence of solvents or in organic solvents, such as hydrocarbons (for example, toluene or chlorobenzene), cyclic ethers (for example dioxane or tetrahydrofuran) or dimethylsulphoxide, until the evolution of hydrogen chloride has ceased. These reactions are carried out in the temperature range between 0° and 250° C. and preferably between 20° C. and 220° C.

However, it is also possible to carry out the reactions with the addition of acid-binding agents and these are used in twice the molar amount when compound (II) is employed, or three times the molar amount when compound (III) is employed. Suitable acid-binding agents are: alkali metal oxides, hydroxides and carbonates and alkaline earth metal oxides, hydroxides and carbonates, as well as tertiary amines, such as pyridine, triethylamine and N,N-dimethylaniline. The reaction temperatures are then $-20°$ to $+120°$ C. and preferably 0° to 70° C.

However 4,5-dichloro-imidazoles which are substituted in the 2-position by heterocyclic radicals can also be obtained by further reaction of secondary products of (II) and (III).

An example which may be mentioned is the reaction of 4,5-dichloro-imidazole-2-thiocarboxylic acid amide (XLIII) with α-halogeno-carbonyl compounds, which leads to 2thiazolo-4,5-dichloro-imidazoles (LXI):

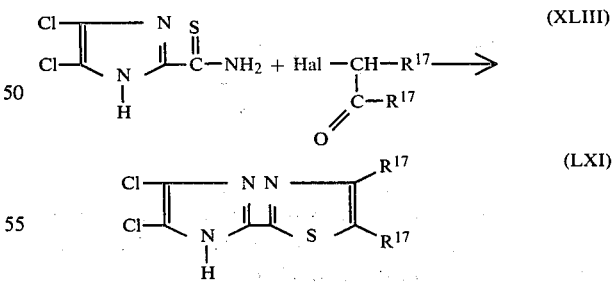

The procedure is the same as that already described in the literature for other thiazole derivatives, the reactants being reacted, preferably in an equimolar ratio, in water or organic solvents, such as hydrocarbons, alcohols, ethers, dimethylformamide, acetonitrile or the like. In order to accelerate the reaction, bases which bind a hydrogen halide, such as alkali metal oxides, hydroxides and carbonates and alkaline earth metal oxides, hydroxides and carbonates, or tertiary amines, such as triethylamine, N,N-dimethylaniline or pyridine, can be added. The reaction temperatures are from 0° to 150° C. and preferably 15° to 100° C.

In formula (LXI),
R$^{17}$ preferably denotes hydrogen, $C_1$–$C_{12}$-alkyl cycloalkyl with 5 or 6 ring carbon atoms, or aralkyl or aryl which are optionally substituted in the aryl part by halogen, methyl, OH, $C_1$–$C_4$-alkoxy, $C_1$–$C_4$-alkylmercapto or $NO_2$.

The two radicals R$^{17}$ can also be joined to one another to form a 5-membered or 6-membered carbocyclic or heterocyclic ring.

The active compounds according to the invention are distinguished by a broad herbicidal spectrum of action; they are distinctly superior to the benzimidazole-2-carboxylic acid derivatives previously known and thus represent an enrichment of the art. The active compounds can be used both in the pre-emergence process and in the post-emergence process. If the active compounds are used as total herbicides, their use after the emergence of the plants is preferred, while if they are used for the selective combating of weeds their use before emergence is preferred.

The amount of active compound employed can vary within a wide range. It depends essentially on the nature of the desired effect. In general, the amounts used are between 0.1 and 25 kg/ha, preferably between 0.25 and 10 kg/ha.

The compounds are suitable for combating weeds in cereals, cotton and corn and as selective herbicides and, when applied in larger amounts, can also be used as total herbicides. The possibilities for use for selective combating of weeds and as total herbicides are largely dependent on the amount applied.

The active compounds according to the invention influence plant growth and can therefore be used as defoliants, desiccants, agents for destroying broad-leaved plants, germination inhibitors and especially as weed-killers. Weeds in the broadest sense are to be understood as all plants which grow in locations where they are not desired. Whether the compounds according to the invention act as total herbicides or selective herbicides depends essentially on the amount used.

The active compounds according to the invention can be used, for example, in connection with the following plants:
dicotyledon weeds such as mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), toothcup (Rotala), Lindernia, deadnettle (Lamium), speedwell (Veronica), mallow (Abutilon), emex (Emex), thornapple (Datura), violet (Viola), hemp-nettle (Galeopsis), poppy (Papaver) and knapweed (Centaurea);
dicotyledon cultures such as cotton (Gossypium), soy bean (Glycine), beet (Beta), carrot (Daucus), bean (Phaseolus), pea (Pisum), potato (Solanum), flax (Linum), morning glory (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cuburbita);

monocotyledon weeds such as barnyard grass (Echinochloa), foxtail (Setaria), wild millet (Panicum), crabgrass (Digitaria), timothy (Phleum), bluegrass (Poa), fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bent-grass (Apera); and
monocotyledon cultures such as rice (Oryzae), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

However, the use of the active compounds according to the invention is in no way restricted to these plants or even to the indicated genera but extends in the same manner to other plants.

Depending on the concentration, the compounds can be used for the total combating of weeds, for example on industrial installations and railway lines, and on paths and open areas which may or may not be planted with trees. Equally, the compounds can be employed for combating weeds in perennial cultures, for example afforestations, arboreta, orchards, vineyards, citrus fruit plantations, nut plantations, banana plantations, coffee plantations, tea plantations, rubber plantations, oil palm plantations, cocoa plantations, soft fruit plantings and hopfields, and for the selective combating of weeds in annual cultures.

The active compounds according to the invention can be combined, as such or in their formulations, with other herbicidal active compounds in order to boost and supplement their spectrum of action, depending on their intended use, it being possible to employ finished formulations or tank mixing. In particular, the active compounds mentioned below and other representatives of groups of active compounds characterized by these active compounds are also suitable for such combinations.

2,3,6-Trichlorobenzoic acid and its salts, 2,3,5,6-tetrachlorobenzoic acid and its salts, 3-nitro-2,5-dichlorobenzoic acid and its salts, 3-amino-2,5-dichlorobenzoic acid and its salts, 2-methoxy-3,6-dichlorobenzoic acid and its salts, 2-methoxy-3,5,6-trichlorobenzoic acid and its salts, 2,6-dichloro-thiobenzamide, 2,6-dichlorobenzonitrile, 2,4-dichlorophenoxyacetic acid and its salts and esters, 2,4,5-trichlorophenoxyacetic acid and its salts and esters, (2-methyl-4-chlorophenoxy)-acetic acid and its salts and esters, 2-(2,4-dichlorophenoxy)-propionic acid, 2-(2-methyl-4-chlorophenoxy)-propionic acid and 2-(2,4,5-trichlorophenoxy)propionic acid and their salts and esters, 4-(2,4-dichlorophenoxy)-butyric acid and its salts and esters, 4-(2-methyl-4-chlorophenoxy)-butyric acid and its salts and esters, 2,3,6-trichlorophenyl-acetic acid and its salts and 4-amino-3,5,6-trichloropicolinic acid.

Trichloroacetic acid and its salts, 2,2-dichloropropionic acid and its salts, 2-chloro-N,N-diallylacetic acid amide, dinitrocresol and dinitro-sec.-butylphenol and its salts.

3-Phenyl-1,1-dimethyl-urea, 3-(4'-chlorophenyl)-1,1-dimethyl-urea, 3-(3',4'-dichlorophenyl)-1,1-dimethyl-urea, 3-(3',4'-dichlorophenyl)-1-n-butyl-1-methyl-urea, 3-(3',4'-dichlorophenyl)-1,1,3-trimethyl-urea, 3-(4'-chlorophenyl)-1-methoxy-1-methyl-urea, 3-(3'-trifluoromethyl-phenyl)-1,1-dimethyl-urea, 3-(3',4'-dichlorophenyl)-1-methoxy-1-methyl-urea, (3-(4'-bromophenyl)-1-methoxy-1-methyl-urea, 3-(3',4'-dichlorophenyl)-3-methoxy-1,1-dimethyl-urea, 3-(4'-chlorophenoxyphenyl)-1,1-dimethyl-urea, N'-cyclooctyl-N,N-dimethylurea, 3-(benzthiazol-2-yl)-1,3-dimethylurea and 3-(3-chloro-4-methylphenyl)-1,1-dimethylurea.

N,N-Di(n-propyl)-S-n-propyl-thiocarbamic acid ester, N-ethyl-N-(n-butyl)-S-n-propyl-thiocarbamic acid ester, N,N-di-(n-propyl)-S-ethyl-thiocarbamic acid ester, N-phenyl-O-isopropyl-carbamic acid ester, N-(m-chlorophenyl)-O-isopropylcarbamic acid ester, N-(3',4'-dichlorophenyl)-O-methylcarbamic acid ester, N-(m-chlorophenyl)-O-(4-chloro-butin-2-yl)-carbamic acid ester, N-(3'-methylphenyl)-O-(3-methoxycarbonylaminophenyl)-carbamic acid ester and N,N-diisopropylthiocarbamic acid 2,3,3-trichloroallyl ester.

3-Cyclohexyl-5,6-trimethylene-uracil, 5-bromo-3-sec.butyl-6-methyl-uracil, 3,6-dioxo-1,2,3,6-tetrahydropyridazine, 4-amino-5-chloro-1-phenyl-6-pyridazone.

2-Chloro-4-ethylamino-6-isopropylamino-s-triazine, 2-chloro-4,6-bis-(methoxypropylamino)-s-triazine, 2-methoxy-4,6-bis-(isopropylamino)-s-triazine, 2-diethylamino-4-isopropylacetamido-6-methoxy-s-triazine, 2-isopropylamino-4-methoxypropylamino-6-methylthio-s-triazine, 2-methylthio-4,6-bis-(isopropylamino)-s-triazine, 2-chloro-4,6-bis-(ethylamino)-s- triazine, 2-methylthio-4,6-bis-(ethylamino)-s-triazine, 2-methoxy-4-ethylamino-6-isopropylamino-s-triazine, 2-methylthio-4-ethylamino-6-isopropylamino-s-triazine, 2-methoxy-4,6-bis-(ethylamino)-s-triazine and 2-chloro-4,6-bis-(isopropylamino)-s-triazine.

N,N-Diethyl-2,4-dinitro -6- trifluoromethyl-1,3-phenylenediamine, N,N-di-n-propyl-2,6-dinitro-4-trifluoromethylaniline, 4'-nitro-2,4-dichloro-diphenyl ether, 3,4-dichlorophenyl-propionamide and 2',6'-diethyl-N-(methoxymethyl)-2-chloroacetanilide.

The active compounds according to the invention exhibit a powerful fugitoxic and bacteriotoxic action. They do not damage crop plants in the concentrations required for combating fungi and bacteria. For these reasons they are suitable for use as plant protection agents for combating fungi and bacteria. Fungitoxic agents in plant protection are employed for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be employed against parasitic fungi which infest above-ground parts of plants or attack the plants through the soil, as well as against seed-borne pathogens.

The active compounds according to the invention exhibit a particularly good activity against parasitic fungi which attack above-ground parts of plants, such as rust diseases on cereals caused by species of Puccinia, and bean rust (*Uromyces phaseolie*), as well as against powdery mildew caused by species of Erysiphe and powdery mildew of apples (*Podosphaera leucotricha*) and, in the case of rice, against *Pyricularia oryzae* and *Pellicularia sasakii*. On above-ground parts of plants the compounds are also active against species of Botrytis, species of Septoria, species of Helminthosphorium and species of Cercospora. The active compounds according to the invention are effective, and of particular practical importance, when employed as seed dressings or soil treatment agents against phytopathogenic fungi which adhere to the seed and occur in the soil, and which in crop plants cause seedling diseases, root rot, tracheomycoses and seed diseases, such as species of Fusarium, species of Rhizoctonia, *Verticillium alboatrum* and *Phialophora cinerescens*.

The active compounds according to the invention are well tolerated by plants in the amounts which require to be used for combating fungal and bacterial pathogens.

The active compounds are also suitable for combating arthropod pests, especially insects or arachnids, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp., and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Escelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Pródenia litura,* Spodoptera spp., Trichoplusia ni, *Carpocapsa pomonella,* Pieris spp., Chilo spp., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha*

*dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp. *Meligethes aeneus,* Ptinus spp, *Niptus hololeucus, Gibbium pyslloides,* Tribolium spp., *Tenebrio molitor, Agriotes spp., Conoderus spp., Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example, *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp, and Tetranychus spp..

The plant-parasitic nematodes include Pratylenchus spp., *Radopholus similis, Ditylenchus dipsaci, Tylenchulus semi-penetrans,* Heterodera spp., Meloidogyne spp., Aphelenchoides spp., Longidorus spp., Xiphinema spp., and Trichodorus spp..

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.) and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other nematicides, insecticides, acaricides, fungicides and herbicides, or bactericides, rodenticides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0000001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

When using against nematodes, the preparations are generally applied to an area of agriculture in amounts of 1 to 100 kg of active compound per hectare, and are then incorporated into the soil.

Especially in the case of use as leaf fungicides, the active compound concentrations in the use forms can vary within a fairly wide range. They are in general between 0.1 and 0.00001 percent by weight, preferably between 0.05 and 0.0001%.

In the case of the treatment of seed, amounts of active compound of 0.001 to 50 g per kilogram of seed, preferably 0.01 to 10 g, are generally employed.

For the treatment of soil, amounts of active compound of 1 to 1,000 g per cubic meter of soil, preferably of 10 to 200 g are generally employed.

Furthermore, the present invention contemplates methods of selectively killing, combating or controlling pests, e.g. nematodes, insects, acarids, fungi and unwanted vegetation such as weeds, which comprises applying to at least one of correspondingly (a) such nematodes, (b) such insects, (c) such acarids, (d) such fungi, (e) such unwanted vegetation, and (f) the corresponding habitat thereof, i.e. the locus to be protected, e.g. to a growing crop, to an area where a crop is to be grown or to a domestic animal, a correspondingly combative or toxic amount, i.e. a nematicidally, insecticidally, acaricidally, fungicidally or herbicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The insecticidal, acaricidal, fungicidal, nematicidal and herbicidal activity of the compounds of this invention is illustrated by the following biological examples, in which the active compounds according to the invention are each identified by the number of the corresponding preparative example given later in the text.

The known comparison compounds are identified by letters as follows:

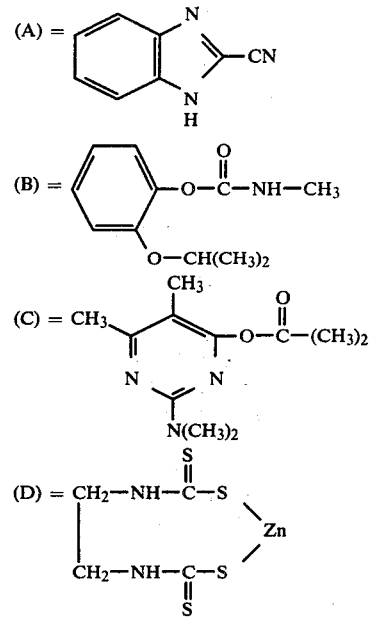

EXAMPLE 1

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5-15 cm were sprayed with the preparation of the active compound in such a way as to apply the amounts of active compound per unit area which are indicated in the table. The concentration of the spray liquor was so chosen that the amounts of active compound shown in the table were applied in 2,000 l of water/ha. After three weeks, the degree of damage to the plants was rated on a scale of 0-5. The figures denoted:

0 = no action (like untreated control)
5 = total destruction.

The active compounds, the amounts applied and the results can be seen from the table which follows:

Table 1

| Compound | Amount of active compound used kg/ha | Echinochloa | Chenopodium | Galinsoga | Stellaria | Urtica | Matricaria | Daucus | Sinapis | Oats | Cotton | Wheat |
|---|---|---|---|---|---|---|---|---|---|---|---|---|
| (A) | 1 | 3 | 2 | 1 | 4 | 2 | 1 | 0 | 3 | 3 | 2 | 3 |
|  | 0.5 | 1 | 0 | 1 | 2 | 1 | 1 | 0 | 3 | 2 | 0 | 1 |
| 13 | 1 | 5 | 5 | 5 | 5 | 5 | 5 | 5 | 5 | 4 | 2 | 3 |
|  | 0.5 | 5 | 5 | 5 | 4-5 | 4 | 5 | 5 | 5 | 2 | 2 | 2 |
| 14 | 1 | 5 | 5 | 5 | 5 | 5 | 5 | 5 | 5 | 4 | 4 | 3 |
|  | 0.5 | 5 | 5 | 5 | 5 | 5 | 5 | 5 | 5 | 4 | 4 | 2 |
| 10 | 1 | 5 | 5 | 5 | 5 | 4-5 | 5 | 5 | 5 | 2 | 1 | 3 |
|  | 0.5 | 5 | 4 | 5 | 5 | 3 | 3 | 5 | 5 | 2 | 0 | 2 |
| 28 | 1 | 5 | 5 | 5 | 5 | 5 | 5 | 5 | 5 | 3 | 3 | 2 |
|  | 0.5 | 5 | 4-5 | 5 | 5 | 4 | 5 | 5 | 4-5 | 3 | 1 | 2 |
| 54 | 1 | 5 | 5 | 5 | 5 | 5 | — | 5 | 5 | 4 | 3 | 4 |
|  | 0.5 | 4 | 5 | 5 | 3 | 4 | — | 5 | 5 | 4 | 1 | 3 |

Table 1-continued

| Compound | Amount of active compound used kg/ha | Echinochloa | Chenopodium | Galinsoga | Stellaria | Urtica | Matricaria | Daucus | Sinapis | Oats | Cotton | Wheat |
|---|---|---|---|---|---|---|---|---|---|---|---|---|
| 51 | 1 | 5 | 5 | 5 | 5 | 5 | — | 5 | 5 | 4 | 2 | 3 |
|  | 0.5 | 5 | 5 | 5 | 3 | 3 | — | 5 | 5 | 4 | 1 | 3 |
| 62 | 1 | 4–5 | 5 | 5 | 4 | — | 5 | 5 | 5 | 1 | 4 | 2 |
|  | 0.5 | 3 | 5 | 5 | 3 | — | 5 | 5 | 5 | 0 | 1 | 1 |
| 65 | 1 | 3 | 5 | 5 | 2 | — | 5 | 5 | 5 | 4 | 4 | 2 |
|  | 0.5 | 2 | 4–5 | 5 | 1 | — | 5 | 5 | 3 | 1 | 2 | 1 |
| 71 | 1 | 4–5 | 5 | 5 | 5 | — | 5 | 5 | 5 | 2 | 3 | 3 |
|  | 0.5 | 2 | 5 | 5 | 5 | — | 4 | 2 | 4 | 0 | 3 | 2 |
| 70 | 1 | 5 | 5 | 5 | 5 | 5 | 5 | 5 | 5 | 4 | 5 | 4 |
|  | 0.5 | 5 | 5 | 5 | 5 | 5 | 5 | 5 | 5 | 3 | 5 | 4 |
| 128 | 1 | 4 | 5 | 5 | 5 | 5 | 5 | 5 | 5 | 5 | 5 | 4–5 |
|  | 0.5 | 3 | 5 | 5 | 5 | 5 | 5 | 5 | 5 | 4–5 | 5 | 4 |
| 3 | 1 | 5 | 5 | 5 | 5 | 5 | 5 | 5 | 5 | 5 | 5 | 5 |
|  | 0.5 | 5 | 5 | 5 | 5 | 5 | 5 | 5 | 5 | 5 | 5 | 5 |
| 90 | 1 | 5 | 5 | 5 | 5 | 4 | 5 | 5 | 5 | 4 | 3 | 5 |
|  | 0.5 | 4 | 5 | 5 | 5 | 3 | 5 | 5 | 5 | 3 | 1 | 5 |
| 89 | 1 | 3 | 5 | 5 | 2 | 3 | 5 | 5 | 5 | 2 | 1 | 3 |
|  | 0.5 | 1 | 5 | 4 | 2 | 3 | 5 | 5 | 5 | 1 | 0 | 3 |
| 41 | 1 | 4 | 5 | 5 | 5 | 5 | 5 | 5 | 5 | 4–5 | 4 | 5 |
|  | 0.5 | 4 | 5 | 5 | 5 | 5 | 5 | 5 | 5 | 4 | 1 | 5 |
| 142 | 1 | 3 | 4–5 | 5 | 3 | 5 | 3 | 5 | 5 | 3 | 2 | 4 |
|  | 0.5 | 0 | 3 | 3 | 1 | 4 | 1 | 4 | 5 | 2 | 1 | 2 |
| 237 | 1 | 4 | 4–5 | 5 | 4 | 5 | 3 | 5 | 5 | 3 | 1 | 3 |
|  | 0.5 | 1 | 4 | 3 | 2 | 3 | 2 | 3 | 5 | 3 | 0 | 2 |
| 238 | 1 | 3 | 5 | 5 | 5 | 5 | 5 | 5 | 5 | 3 | 4–5 | 3 |
|  | 0.5 | 2 | 5 | 5 | 5 | 5 | 5 | 5 | 5 | 2 | 2 | 2 |
| 239 | 1 | 4 | 5 | 5 | 5 | 5 | 5 | 5 | 5 | 2 | 3 | 4 |
|  | 0.5 | 3 | 5 | 5 | 4 | 5 | 5 | 5 | 5 | 2 | 2 | 3 |
| 244 | 1 | 2 | 5 | 5 | 5 | 3 | 5 | — | 4 | 3 | 1 | 3 |
|  | 0.5 | 0 | 5 | 4 | 5 | 3 | 5 | — | 4 | 3 | 1 | 2 |

EXAMPLE 2

Pre-emergence Test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

The active compounds, the amounts applied and the results can be seen from the table which follows:

Table 2

| Compound | Amount of active compound used kg/ha | Echinochloa | Chenopodium | Galinsoga | Stellaria | Lolium | Matricaria | Sinapis | Corn | Oats | Cotton |
|---|---|---|---|---|---|---|---|---|---|---|---|
| (A) | 5 | 3 | 0 | — | 1 | — | 4 | 0 | 0 | 0 | 0 |
|  | 2.5 | 2 | 0 | — | 0 | 0 | 4 | 0 | 0 | 0 | 0 |
| 70 | 5 | 5 | 5 | 5 | 5 | 5 | 5 | 5 | 1 | 2 | 2 |
|  | 2.5 | 5 | 5 | 5 | 5 | 4–5 | 5 | 4–5 | 0 | 1 | 1 |
| 3 | 5 | 5 | 5 | 5 | 5 | 5 | 5 | 5 | 4–5 | 4 | 4 |
|  | 2.5 | 5 | 5 | 5 | 5 | 5 | 5 | 5 | 4–5 | 4 | 3 |
| 90 | 5 | 5 | 5 | — | 5 | 5 | 5 | 5 | 3 | 4–5 | 3 |
|  | 2.5 | 5 | 5 | — | 5 | 5 | 5 | 5 | 3 | 4–5 | 2 |
| 89 | 5 | 5 | 5 | — | 5 | 5 | 5 | 5 | 3 | 4 | 1 |
|  | 2.5 | 5 | 5 | — | 5 | 5 | 5 | 5 | 2–3 | 3 | 0 |
| 41 | 5 | 5 | 5 | — | 5 | 5 | 4 | 5 | 4 | 4 | 2 |
|  | 2.5 | 5 | 5 | — | 5 | 5 | 4 | 5 | 3 | 4 | 2 |
| 142 | 5 | 4 | 5 | 5 | 5 | 4 | 5 | 5 | 3 | 4 | 3 |
|  | 2.5 | 4 | 5 | 5 | 5 | 4 | 5 | 5 | 2 | 4 | 2 |
| 237 | 5 | 5 | 5 | 5 | 5 | 4 | 5 | 4 | 4 | 4 | 3 |
|  | 2.5 | 5 | 5 | 5 | 5 | 4 | 5 | 4 | 3 | 4 | 2 |
| 238 | 5 | 3 | 5 | 5 | 4 | 3 | 5 | 5 | 2 | 3 | 2 |
|  | 2.5 | 3 | 5 | 5 | 4 | 3 | 5 | 4 | 2 | 3 | 2 |
| 239 | 5 | 3 | 5 | 5 | 5 | 3 | 5 | 5 | 3 | 3 | 2 |
|  | 2.5 | 2 | 5 | 5 | 5 | 3 | 5 | 5 | 3 | 3 | 2 |

Table 2-continued

| Com-pound | Amount of active compound used kg/ha | Pre-emergence Test | | | | | | | | | |
|---|---|---|---|---|---|---|---|---|---|---|---|
| | | Echino-chloa | Cheno-podium | Galin-soga | Stella-ria | Lolium | Matricaria | Sinapis | Corn | Oats | Cotton |
| 144 | 5 | 4–5 | 5 | 5 | 5 | 4 | 5 | 5 | 2 | 5 | 4 |
| | 2.5 | 4 | 5 | 5 | 5 | 4 | 5 | 5 | 1 | 4 | 3 |
| 145 | 5 | 5 | 5 | 5 | 5 | 4 | 5 | 5 | 3 | 5 | 4 |
| | 2.5 | 5 | 5 | 5 | 5 | 4 | 5 | 5 | 2 | 4 | 4 |
| 147 | 5 | 5 | 5 | 5 | 5 | 4 | 5 | 5 | 2 | 5 | 4 |
| | 2.5 | 5 | 5 | 5 | 5 | 4 | 5 | 5 | 0 | 4 | 3 |
| 148 | 5 | 4 | 5 | 5 | 5 | 4 | 5 | 5 | 3 | 5 | 4 |
| | 2.5 | 4 | 5 | 5 | 5 | 3 | 4 | 5 | 2 | 4 | 2 |
| 149 | 5 | 5 | 5 | 5 | 5 | 4 | 5 | 5 | 3 | 5 | 4 |
| | 2.5 | 5 | 5 | 5 | 5 | 3 | 4 | 5 | 1 | 5 | 3 |
| 150 | 5 | 5 | 5 | 5 | 5 | 4 | 5 | 5 | 2 | 5 | 4 |
| | 2.5 | 4 | 5 | 4 | 5 | 2 | 5 | 5 | 1 | 4 | 3 |

EXAMPLE 3

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of emulsifier W and then 975 parts by weight of water are added. The concentrate was diluted with water to the desired final concentration of the spray liquor.

To test the protective activity, one-leaved young wheat plants of the Michigan Amber variety were inoculated with a uredospore suspension of Puccinia recondita in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection of the inoculated leaves was evaluated in terms of a scale from 1 to 9. 1 denoted 100% action, 3 denoted very good action, 5 denoted moderate action and 9 denoted no action.

The active compounds, active compound concentrations in the spray liquor and degrees of infection can be seen from the table which folllows:

Table 3

Shoot treatment test/cereal rust, protective

| Active compounds | Active compound concentration in the spray liquor in % by weight | Infection |
|---|---|---|
| (A) | 0.025 | 9 |
| 21 | 0.025 | 1 |
| 23 | 0.025 | 1 |
| 32 | 0.025 | 2 |
| 35 | 0.025 | 3 |
| 39 | 0.025 | 1 |
| 5 | 0.025 | 2 |
| 28 | 0.025 | 3 |
| 29 | 0.025 | 1 |
| 6 | 0.025 | 1 |
| 44 | 0.025 | 3 |
| 65 | 0.025 | 3 |
| 71 | 0.025 | 1 |
| 67 | 0.025 | 3 |
| 69 | 0.025 | 3 |

Table 3-continued

Shoot treatment test/cereal rust, protective

| Active compounds | Active compound concentration in the spray liquor in % by weight | Infection |
|---|---|---|
| 70 | 0.025 | 3 |
| 47 | 0.025 | 3 |
| 121 | 0.025 | 3 |
| 53 | 0.025 | 3 |
| 56 | 0.025 | 2 |
| 74 | 0.025 | 3 |
| 128 | 0.025 | 3 |
| 139 | 0.025 | 1 |
| 138 | 0.025 | 1 |
| 129 | 0.025 | 3 |
| 132 | 0.025 | 1 |

EXAMPLE 4

Mycelium growth test

Nutrient medium used:
  20 parts by weight of agar-agar
  200 parts by weight of potato decoction
  5 parts by weight of malt
  15 parts by weight of dextrose
  5 parts by weight of peptone
  2 parts by weight of $Na_2HPO_4$
  0.3 part by weight of $Ca(NO_3)_2$ Ratio of solvent mixture of nutrient medium:
  2 parts by weight of solvent mixture
  100 parts by weight of agar nutrient medium Composition of the solvent mixture:
  0.19 part by weight of DMF or acetone
  0.01 part by weight of emulsifier (alkylaryl polyglycol ether)
  1.80 parts by weight of water The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, depending upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to
3 very strong inhibition of growth
up to
5 medium inhibition of growth
up to
7 slight inhibition of growth
9 growth equal to that of untreated control.

The active compounds, the active compound concentrations and the results can be seen from the following table:

Table 4

| Mycelium growth test Active compound concentration of 10 ppm Active compounds | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialphora cinerescens | Helminthosporium gramineum | Mycosphaerella musicola | Phytophthora cactorum | Venturia inaequalis | Pellicularia sasakii | Xanthomonas oryzae |
|---|---|---|---|---|---|---|---|---|---|---|---|---|---|---|---|---|---|
| (A) | 9 | 9 | 9 | 9 | 9 | 9 | 9 | 9 | 9 | 9 | 9 | 9 | 9 | 9 | 9 | 9 | 9 |
| 22 | 5 | 1 | 5 | — | 1 | 1 | — | — | 5 | 1 | — | 1 | 1 | 1 | — | — | 1 |
| 23 | — | 1 | 1 | — | — | 1 | — | 1 | 1 | — | 1 | 1 | 1 | 1 | — | — | — |
| 28 | 1 | 2 | — | 2 | 2 | 2 | 2 | 1 | 5 | 1 | — | 1 | 1 | 1 | — | 1 | — |
| 39 | — | — | — | — | 1 | 1 | 5 | 5 | — | 5 | — | 1 | 5 | 3 | — | — | — |
| 56 | 5 | 3 | 5 | — | 5 | 3 | 5 | 3 | 5 | 3 | — | 1 | 5 | 3 | — | 1 | — |
| 61 | — | 5 | — | — | — | 5 | 5 | 5 | 5 | 1 | — | 1 | 1 | 1 | — | 5 | — |
| 69 | — | 5 | — | 5 | 5 | 5 | 5 | 5 | — | 1 | — | 1 | 5 | 1 | — | — | — |
| 84 | — | 1 | — | — | 1 | — | 5 | — | — | 1 | — | 1 | — | 1 | — | 1 | — |
| 132 | — | — | — | — | — | 2 | 5 | 5 | 5 | 1 | — | 1 | — | 5 | — | — | — |
| 40 | 3 | 3 | 3 | 5 | 5 | 5 | 5 | 5 | — | 1 | 5 | 1 | — | 5 | — | 1 | — |
| 73 | 3 | 1 | 3 | 3 | 5 | 3 | 3 | — | — | 1 | 5 | 1 | — | 3 | — | 3 | — |
| 48 | 5 | 3 | 5 | 1 | 5 | 3 | 3 | 5 | — | 1 | 5 | 1 | — | 5 | — | 1 | — |
| 47 | 3 | 2 | 3 | — | 1 | 5 | 2 | — | 5 | — | — | 1 | — | 5 | — | 1 | — |
| 92 | 3 | 3 | 3 | 5 | 3 | — | 3 | — | 5 | 1 | — | 1 | — | 5 | — | 1 | — |
| 97 | — | — | — | — | — | 5 | 5 | — | — | — | — | 1 | — | — | — | — | — |
| 95 | — | — | — | — | 5 | 3 | 5 | 5 | 5 | 5 | — | 1 | — | 2 | — | — | 5 |
| 119 | — | 1 | 5 | 1 | 1 | — | 5 | 5 | 5 | — | — | 1 | — | 3 | — | — | — |
| 177 | 1 | 1 | 5 | — | 1 | 5 | 5 | 5 | 5 | 3 | — | 1 | — | 5 | — | 1 | 5 |
| 180 | — | — | 5 | — | 1 | 3 | 5 | 3 | 5 | 5 | — | 1 | — | 5 | — | — | — |
| 153 | — | — | — | 5 | 5 | 5 | 5 | 2 | — | — | — | 1 | — | 5 | — | 1 | — |
| 187 | 1 | — | 5 | 3 | 3 | 5 | 5 | 5 | 5 | 3 | — | 5 | — | — | — | — | — |
| 183 | — | 1 | 5 | 5 | 5 | 5 | 5 | 5 | 5 | 5 | — | 5 | — | — | — | — | — |
| 191 | — | — | 5 | 5 | 3 | 2 | 3 | 3 | 5 | 3 | — | 1 | — | — | — | 5 | — |
| 155 | 5 | 5 | — | 1 | 2 | 1 | 3 | 2 | — | — | — | 1 | — | — | — | 5 | 5 |
| 193 | 5 | — | — | 5 | 5 | 5 | 5 | 5 | 3 | 5 | — | 3 | — | 5 | — | 3 | — |
| 198 | — | 1 | 3 | 1 | 1 | 3 | 3 | 3 | — | 3 | — | 1 | — | — | — | — | — |
| 157 | — | — | — | — | 1 | — | — | 5 | 5 | — | — | — | — | — | — | 1 | — |
| 165 | 5 | 5 | — | 1 | 1 | 5 | 5 | 5 | 5 | — | — | 5 | — | 5 | — | 5 | 5 |
| 163 | 5 | 1 | 5 | 1 | — | 3 | 3 | 3 | — | — | — | 1 | — | — | — | 5 | — |
| 218 | — | 1 | 3 | — | 3 | 2 | — | — | — | — | — | 3 | — | 5 | — | 3 | — |
| 168 | 3 | — | — | 1 | 5 | 1 | 5 | 5 | 3 | 5 | — | 1 | — | 5 | — | — | 5 |
| 205 | — | — | 3 | 2 | 3 | 5 | 3 | 5 | — | — | — | 2 | — | 5 | — | — | — |
| 207 | 5 | — | 3 | 1 | 2 | 1 | 3 | 3 | — | — | — | 1 | — | — | — | — | — |
| 208 | 5 | 5 | 5 | 5 | 5 | 5 | 5 | 5 | 3 | 3 | — | 3 | — | — | — | 5 | — |
| 170 | 5 | 1 | 5 | 1 | 2 | — | 5 | 5 | — | — | — | 5 | — | — | — | 3 | — |
| 210 | — | — | — | — | 1 | 3 | 3 | 5 | — | 1 | — | 1 | — | 3 | — | — | — |
| 213 | — | — | — | 1 | 1 | 1 | 3 | — | — | — | — | 1 | — | 5 | — | 5 | — |
| 226 | — | 1 | 5 | — | — | — | — | — | — | — | — | — | — | — | — | 2 | — |
| 227 | 5 | 1 | 3 | 1 | 1 | 3 | 3 | 5 | 5 | 1 | — | 3 | — | 1 | — | 5 | — |

EXAMPLE 5

Phaedon larvae test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all the beetle larvae had been killed, whereas 0% meant that none of the beetle larvae had been killed.

The active compounds, the concentrations of the active compounds, the evaluation times and the results can be seen from the following table:

Table 5

| | (Insects which damage plants) Phaedon larvae test | |
|---|---|---|
| Active compounds | Active compound concentration in % | Degree of destruction in % after 3 days |
| (B) | 0.1 | 100 |
| | 0.01 | 0 |
| 207 | 0.1 | 100 |
| | 0.01 | 100 |
| 208 | 0.1 | 100 |
| | 0.01 | 100 |
| 187 | 0.1 | 100 |
| | 0.01 | 100 |
| 161 | 0.1 | 100 |
| | 0.01 | 100 |
| 219 | 0.1 | 100 |
| | 0.01 | 100 |
| 157 | 0.1 | 100 |
| | 0.01 | 100 |
| 168 | 0.1 | 100 |
| | 0.01 | 100 |
| 217 | 0.1 | 100 |
| | 0.01 | 100 |

EXAMPLE 6

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% meant that all the caterpillars were killed, whereas 0% meant that none of the caterpillars were killed.

The active compounds, the concentrations of the active compounds, the evaluation times and the results can be seen from the following table:

Table 6

| | (Insects which damage plants) Plutella test | |
|---|---|---|
| Active compounds | Active compound concentration in % | Degree of destruction in % after 3 days |
| (C) | 0.1 | 0 |
| 191 | 0.1 | 100 |
| 197 | 0.1 | 100 |
| 192 | 0.1 | 100 |
| 193 | 0.1 | 100 |
| 205 | 0.1 | 100 |
| 203 | 0.1 | 100 |
| 201 | 0.1 | 100 |
| 188 | 0.1 | 100 |
| 206 | 0.1 | 100 |
| 194 | 0.1 | 100 |
| 204 | 0.1 | 100 |
| 180 | 0.1 | 100 |
| 199 | 0.1 | 100 |
| 198 | 0.1 | 100 |
| 195 | 0.1 | 100 |
| 152 | 0.1 | 100 |
| 153 | 0.1 | 100 |
| 217 | 0.1 | 100 |
| 209 | 0.1 | 100 |
| 210 | 0.1 | 100 |
| 212 | 0.1 | 100 |
| 213 | 0.1 | 100 |
| 223 | 0.1 | 100 |
| 222 | 0.1 | 100 |
| 225 | 0.1 | 100 |
| 157 | 0.1 | 100 |
| 226 | 0.1 | 100 |
| 220 | 0.1 | 100 |
| 227 | 0.1 | 100 |

EXAMPLE 7

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from the following table:

Table 7

| | (Mites which damage plants) Tetranychus test | |
|---|---|---|
| Active compounds | Active compound concentration in % | Degree of destruction in % after 2 days |
| (C) | 0.1 | 0 |
| 207 | 0.1 | 100 |
| 199 | 0.1 | 99 |
| 193 | 0.1 | 90 |
| 205 | 0.1 | 98 |
| 153 | 0.1 | 90 |

Table 7-continued

| | (Mites which damage plants) Tetranychus test | |
|---|---|---|
| Active compounds | Active compound concentration in % | Degree of destruction in % after 2 days |
| 217 | 0.1 | 99 |

EXAMPLE 8

Phytophthora test (tomatoes)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° C.

After 5 days the infection of the tomato plants was determined. The assessment data were converted to percent infection. 0% meant no infection; 100% meant that the plants were totally infected.

The active compound, the concentrations of the active compound and the results can be seen from the following table:

Table 8

| Phytophthora test (tomatoes)/protective | |
|---|---|
| Active compound | Infection in % at an active compound concentration of 0.0025% |
| (D) | 56 |
| 179 | 7 |
| 192 | 1 |
| 195 | 2 |
| 199 | 4 |

EXAMPLE 9

Shoot treatment test/cereal rust/protective (leaf-destructive mycosis)

To produce a suitable preparation of active compound, 0.25 part by weight of active compound was taken up in 25 parts by weight of dimethylformamide and 0.66 part by weight of alkylaryl polyglycol ether emulsifier and 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

The active compounds, active compound concentrations in the spray liquor and degrees of infection can be seen from the table which follows:

Table 9

| Shoot treatment test/cereal rust/protective | | |
|---|---|---|
| Active compounds | Active compound concentration in the spray liquor in % by weight | Infection in % of the untreated control |
| 178 | 0.025 | 25 |
| 184 | 0.025 | 0 |
| 176 | 0.025 | 25 |
| 192 | 0.025 | 0 |
| 196 | 0.025 | 12.5 |
| 197 | 0.025 | 0 |
| 200 | 0.025 | 25 |
| 164 | 0.025 | 25 |
| 219 | 0.025 | 25 |
| 168 | 0.025 | 0 |
| 205 | 0.025 | 0 |
| 167 | 0.025 | 25 |
| 207 | 0.025 | 0 |
| 208 | 0.025 | 0 |
| 169 | 0.025 | 12.5 |
| 171 | 0.025 | 25 |
| 209 | 0.025 | 12.5 |
| 172 | 0.025 | 12.5 |
| 210 | 0.025 | 25 |
| 211 | 0.025 | 0 |
| 213 | 0.025 | 0 |
| 175 | 0.025 | 0 |
| 223 | 0.025 | 25 |
| 226 | 0.025 | 12.5 |
| 227 | 0.025 | 0 |

The process according to the present invention is illustrated by the following preparative examples:

EXAMPLE 10

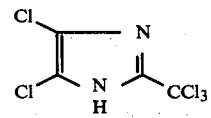

(1)

Dry hydrogen chloride was passed into a solution of 218 g (1.0 mol) of 4,5-dichloro-2-dichloro-methylene-imidazole in about 2 liters of dry toluene until the formation of a precipitate (at least 1 mol) had ended. After cooling (the addition reaction with HCl proceeded exothermically), filtering off and drying, 235 g (89% of theory) of 4,5-dichloro-2-trichloromethyl-imidazole with a melting point of 210° C. (with decomposition) were obtained.

EXAMPLE 11

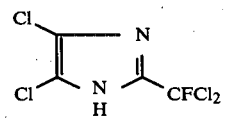

(2)

25 g of 4,5-dichloro-2-dichloromethylene-imidazole in 100 ml of HF were stirred for 4 hours at 100° C. in an autoclave. After cooling and releasing the pressure, the excess HF was removed by distillation. The residue was dissolved in ether, washed briefly twice with cold water and dried over Na₂SO₄ and the solvent was then removed. 21 g of 4,5-dichloro-2-dichloro-fluoromethyl-imidazole were obtained after a single recrystallization from toluene/wash benzine. Melting point: 172° C. with decomposition.

EXAMPLE 12

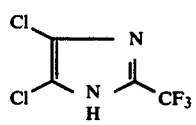
(3)

380 g of 4,5-dichloro-2-trichloromethyl-imidazole were initially introduced into a fluorination autoclave and 400 ml of HF were allowed to run in at 0° C. The autoclave was then closed and Cl₂ was injected, as a blanketing gas, under a pressure of about 2 atmospheres gauge. The mixture was heated up to 100° C. in the course of 1 hour and up to 140° C. in the course of a further 2 hours and this temperature was maintained for a further 3½ hours. The pressure, which rose due to the HCl formed, was released, at 20 bars, via a condenser, by means of a regulating valve.

After cooling and releasing the pressure, the remaining HF was distilled off, the residue was dissolved in tetrahydrofuran and the solution was shaken with NaF. After filtering and distilling off the solvent, 262 g (85.5% of theory) of 4,5-dichloro-2-trifluoromethyl-imidazole with a melting point of 186°–8° C. remained.

EXAMPLE 13

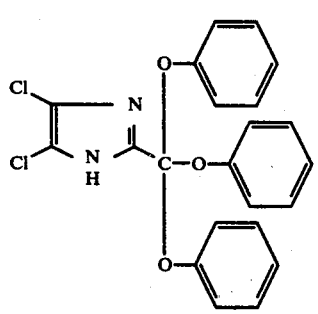
(4)

25.5 g (0.075 mol) of 4,5-dichloro-2-trichloromethyl-imidazole were added incrementally, at 10°–15° C., to a mixture of 28.2 g (0.3 mol) of phenol, 27.3 g (0.3 mol) of concentrated sodium hydroxide solution and 200 ml of dioxan, while stirring vigorously. The reaction mixture was stirred for a further 2 hours at room temperture and 1 l of water was then added. The crystals which had separated out were filtered off and dried. Yield: 25 g (78% of theory) of 4,5-dichloro-2-triphenoxymethyl-imidazole. Melting point: 192°–194° C. (ethyl acetate).

EXAMPLE 14

Using 4-chlorobenzene in place of phenol, 4,5-dichloro-2-tris-(4-chlorophenoxy)-methyl-imidazole of the formula

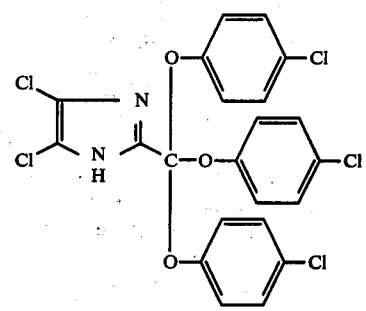
(5)

was obtained in an analogous manner. Melting point: 220°–222° C. (butanol).

EXAMPLE 15

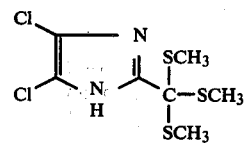
(6)

Methylmercaptan was passed into a solution of 9.2 g (0.4 mol) of sodium in 300 ml of ethanol until the solution was saturated. 25.4 g (0.1 mol) of 4,5-dichloro-2-trichloromethyl-imidazole were added to this solution in small portions at 0°–5° C. The mixture was stirred for a further 2 hours at room temperature, the sodium chloride which had separated out was filtered off and the filtrate was evaporated in vacuo. The residue was taken up in 300 ml of water and the mixture was acidified with hydrochloric acid. The crystals which had separated out were filtered off, washed with water and dried. 23 g (78.5% of theory) of 4,5-dichloro-2-tris-(methylmercapto)-methyl-imidazole with a melting point of 175°–177° C. (from toluene) were obtained.

EXAMPLE 16

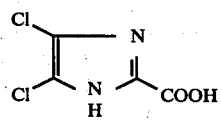
(7)

50 g (0.23 mol) of 4,5-dichloro-2-dichloromethylene-imidazole were boiled with about 250 ml of water for 5–10 minutes, whereupon a colorless solution formed. After cooling, colourless crystals of 4,5-dichloro-imidazole-2-carboxylic acid monohydrate separated out and these melted at 180° C. with decomposition (decarboxylation to give the known 4,5-dichloro-imidazole). Yield: 35 g (80% of theory). The same compound was obtained when 4,5-dichloro-2-trichloromethyl-imidazole was employed.

EXAMPLE 17

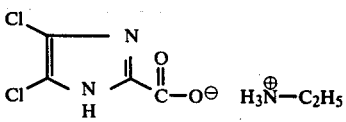
(8)

Concentrated hydrochloric acid was added to 40 g (0.44 mol) of 50 percent strength aqueous ethylamine until an acid reaction was just obtained and the mixture was then boiled briefly with 21.8 g (0.1 mol) of 4,5-dichloro-2-dichloro-methylene-imidazole until a clear solution had formed. After cooling, the solution was rendered slightly alkaline with sodium bicarbonate. The precipitate which had formed was filtered off, washed with water and dried. In this way, 14 g (62% of theory) of the ethylamine salt of 4,5-dichloro-imidazole-2-carboxylic acid, which had a melting point of <290° C., were obtained. The product could be recrystallized from water as long fine needles.

EXAMPLE 18

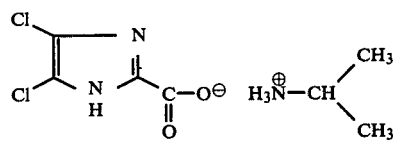

(9)

The isopropylamine salt of 4,5-dichloro-imidazole-2-carboxylic acid, which had a melting point of >290° C., was obtained in a manner similar to that of Example 17.

EXAMPLE 19

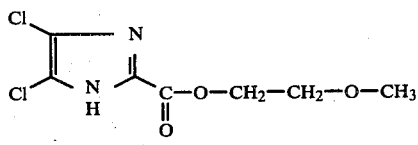

(10)

560 g (2.56 mol) of 4,5-dichloro-2-dichloromethylene-imidazole were added gradually to 1 kg (13.2 mol) of glycol monomethyl ether, while cooling slightly and stirring, at such a rate that the temperature of the exothermic reaction remained at 80°-100° C. The mixture was then evaporated to dryness in vacuo. In this way, 4,5-dichloro-imidazole-2-carboxylic acid methoxyethyl ester was obtained in virtually quantitative yield. Melting point: 130° C.

The same compound was obtained when 4,5-dichloro-2-trichloromethyl-imidazole was employed in place of 4,5-dichloro-2-dichloromethylene-imidazole and in this case the reaction mixture was subsequently heated to 90°-100° C., as appropriate.

The following 4,5-dichloro-imidazole-2-carboxylic acid esters of the general formula

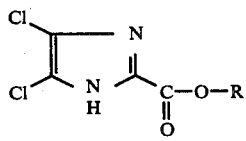

were obtained in a similar way:

Table 10

| Compound No. | R | Melting point °C. |
|---|---|---|
| 11 | CH$_3$ | 160 |
| 12 | C$_2$H$_5$ | 111 |
| 13 | CH$_2$—CH$_2$—CH$_3$ | 85 |
| 14 | CH(CH$_3$)$_2$ | 168 |
| 15 | CH$_2$—CH$_2$Cl | 136 |
| 16 | CH$_2$—CCl$_3$ | 220 |
| 17 | CH$_2$—CH=CH$_2$ | 105 |
| 18 | CH$_2$—C≡CH | 185 |
| 19 | C$_4$H$_9$(n) | 94 |

Table 10-continued

| Compound No. | R | Melting point °C. |
|---|---|---|
| 20 | C$_4$H$_9$(i) | 156 |
| 21 | C$_4$H$_9$(sec.) | 157 |
| 22 | C$_5$H$_{11}$(n) | 40 |
| 23 | C$_6$H$_{13}$(n) | 58 |
| 24 | CH$_2$—C(CH$_3$)$_3$ | 195 |
| 25 | C$_8$H$_{17}$(n) | ~50 |
| 26 | C$_{10}$H$_{21}$(n) | ~40 |
| 27 | C$_{12}$H$_{25}$(n) | ~40 |
| 28 | CH(CH$_2$Cl)(CH$_3$) | 131 |
| 29 | CH(CH$_2$Cl)$_2$ (CH with two CH$_2$Cl) | 150 |
| 30 | CH$_2$—CH$_2$—CH(OCH$_3$)(CH$_3$) | 89 |
| 31 | CH$_2$—CH$_2$—CN | 168 |
| 32 | CH$_2$—CH$_2$—O—C$_2$H$_5$ | 70 |
| 33 | CH$_2$—CH$_2$—O—CH(CH$_3$)$_2$ | oil |
| 34 | CH$_2$—CH$_2$—O—C$_4$H$_9$(n) | oil |
| 35 | CH$_2$—CH$_2$—O—CH$_2$—CH$_2$—OCH$_3$ | oil |
| 36 | CH$_2$—CH$_2$—O—CH$_2$—CH$_2$—OC$_2$H$_5$ | oil |
| 37 | —CH$_2$—C$_6$H$_5$ | 139 |
| 38 | —CH$_2$—C$_6$H$_4$—Cl | 137 |
| 39 | —CH$_2$—CH$_2$—C$_6$H$_5$ | 119 |
| 40 | cyclohexyl | 163 |

EXAMPLE 20

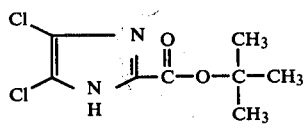

(41)

65 ml of concentrated sulphuric acid were added dropwise, while stirring and while cooling to about 10°-20° C., to a mixture of 130 g (0.65 ml) of 4,5-dichloro-imidazole-2-carboxylic acid monohydrate (for its preparation see Example 16) and 1.3 l of dioxane. A slow stream of gaseous isobutylene was then passed through the reaction mixture at room temperature for about 12 hours. After standing overnight, excess dissolved isobutylene and part of the dioxane were stripped off in vacuo at room temperature and the residue was introduced into about 5 l of ice water. The precipitate which had formed was filtered off, washed with water and dried. This gave 43 g (28% of theory) of 4,5-dichloro-imidazole-2-carboxylic acid tert.-butyl ester. Colorless needles from acetonitrile, with a melting point of 180° C. (with decomposition).

EXAMPLE 21

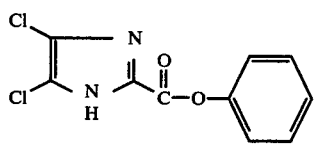 (42)

9.4 g (0.1 mol) of phenol and 25.4 g (0.1 mol) of 4,5-dichloro-2-trichloromethyl-imidazole were dissolved in 150 ml of tetrahydrofuran. 27 g (about 0.3 mol) of concentrated sodium hydroxide solution were added dropwise to this solution, at 0°–5°, while stirring vigorously. The mixture was stirred for 1 hour with cooling and for a further 1 hour at room temperature. 1 Liter of water was then added, the mixture was acidified with hydrochloric acid and the crystals which had separated out were filtered off. The latter were washed with water and dried. Yield: 11.2 g (43.5% of theory) of 4,5-dichloro-imidazole-2-carboxylic acid phenyl ester with a melting point of 102°–103° C. (form toluene).

EXAMPLE 22

In a corresponding manner, 4,5-dichloro-imidazole-2-carboxylic acid 4-nitrophenyl ester of the formula

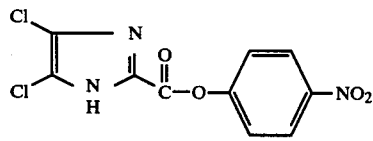 (43)

which had a melting point of 216°–218° C. (from ethanol) was obtained using 4-nitro-phenol in place of phenol.

EXAMPLE 23

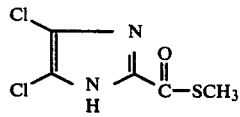 (44)

19.6 g (0.1 mol) of 4,5-dichloro-imidazole-2-thiocarboxylic acid amide and 17 g (0.12 mol) of methyl iodide in 150 ml of dioxane were boiled under reflux for 3 hours. The small amounts of insoluble constituents were filtered off and the solution was evaporated in vacuo. The residue was stirred with approximately 5% strength aqueous hydrochloric acid and the product was filtered off, washed with water and dried. 13.5 g (63% of theory) of 4,5-dichloro-imidazole-2-thiocarboxylic acid S-methyl ester with a melting point of 162°–164° C. (from wash benzine) were obtained.

EXAMPLE 24

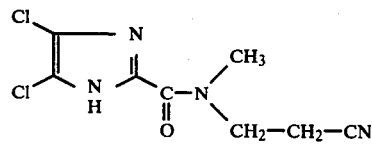 (45)

24 g (0.2 mol) of 3-methylaminopropionitrile hydrochloride were added to a solution of 21.8 g (0.1 mol) of 4,5-dichloro-2-dichloromethylene-imidazole in 100 ml of dioxane and the mixture was heated to the reflux temperature for two hours, while stirring. After cooling, the product was precipitated with water, filtered off, washed with water and dried. In this way, 16.5 g (67% of theory) of 4,5-dichloroimidazole-2-carboxylic acid N-(2-cyanoethyl)-N-methylamide were obtained. Melting point: 184° C. (from acetonitrile).

The following 4,5-dichloro-imidazole-2-carboxamides of the general formula

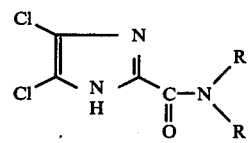

could be obtained in a similar way:

Table 11

| Compound No. | −N(R)(R) | Melting point °C. |
|---|---|---|
| 46 | —N(CH$_3$)$_2$ | 245 (chlorobenzene) |
| 47 | —N(C$_2$H$_5$)$_2$ | 119 (acetonitrile) |
| 48 | —N(piperidinyl) | 213 (acetonitrile) |
| 49 | —N(morpholinyl) | 215 (acetonitrile) |

EXAMPLE 25

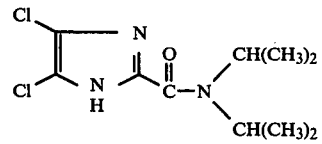 (50)

25.4 g (0.1 mol) of 4,5-dichloro-2-trichloromethyl-imidazole were introduced in small portions, at 0°–5° C., into a mixture of 30.3 g (0.3 mol) of diisopropylamine and 150 ml of methanol. The mixture was stirred for a further 1 hour at room temperature, 150 ml of water were then added and the mixture was stirred for a further hour at room temperature. The mixture was then acidified with hydrochloric acid and cooled in ice. The crystals which had separated out were filtered off, washed with water and dried. Yield: 16.5 g (62.5% of theory) of 4,5-dichloro-imidazole-2-carboxylic acid diisopropylamide. Melting point: 133°–135° C. (wash benzine).

EXAMPLE 26

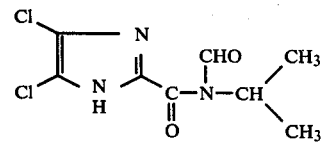 (51)

(a) 654 g (3 mol) of 4,5-dichloro-2-dichloromethylene-imidazole in a finely powdered form were added incrementally in the course of about one hour, to a mixture, which had been initially introduced, of 783 g (9 mol) of isopropyl-formamide, 162 g (9 mol) of water and 3 l of acetonitrile, while stirring and while cooling to about 0° C. The clear solution was then poured into about 15 kg of ice water. The white precipitate which had formed was filtered off, washed with water and dried. In this way, 630 g (84% of theory) of 4,5-dichloro-imidazole-2-carboxylic acid N-formly-isopropylamide with a melting point of 142° C. were obtained. The same result was also achieved without the addition of water.

(b) 21.8 g (0.1 mol) of 4,5-dichloro-2-dichloromethylene-imidazole in a finely powdered form were added incrementally to 87 g (1 mol) of isopropyl-formamide, while stirring, whereupon the reaction mixture warmed to about 40°-50° C. After the exothermic reaction had subsided, the reaction mixture was poured into excess ice water. A viscous precipitate formed first and this solidified after standing for about one hour. After filtering off, washing with water and drying, 23 g of a substance which was largely identical with the product described under (a) were obtained. Melting range about 132°-137° C. By means of fractional crystallization from acetonitrile it was possible, after separating off a more sparingly soluble secondary component, to isolate the product described under (a) in a pure form and with a melting point of 142° C.

(c) When procedure (b) was carried out at a reaction temperature of about 100° C., no substantial change in the composition of the product, compared with (b), was observed.

The following 4,5-dichloro-imidazole-2-carboxylic acid N-formyl-amides of the general formula

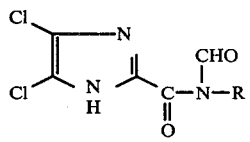

could be obtained in a similar way:

Table 12

| Compound No. | R | Melting point °C. |
|---|---|---|
| 52 | H | 250 |
| 53 | CH$_3$ | 216 |
| 54 | C$_2$H$_5$ | 169 |
| 55 | CH$_2$—CH$_2$OH | 135 |
| 56 | CH$_2$—CH$_2$—CH$_3$ | 140 |
| 57 | CH$_2$—CH$_2$—CN | 150 |
| 58 | CH$_2$—CH=CH$_2$ | 147 |
| 59 | CH$_2$—CH$_2$—CH$_2$—CH$_3$ | 130 |
| 60 | —⟨H⟩ | 172 (decomposition) |
| 61 | —CH$_2$—⟨⟩ | 142 |

EXAMPLE 27

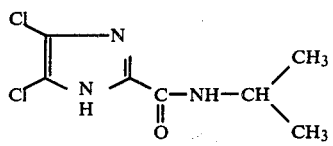 (62)

(a) From 4,5-dichloro-imidazole-2-carboxylic acid N-formyl-isopropylamide (see Example 26).

25 g (0.1 mol) of 4,5-dichloro-imidazole-2-carboxylic acid N-formyl-isopropylamide were stirred with 200 ml of concentrated sulphuric acid for about 15 minutes at 50°-70° C. After cooling, the mixture was poured onto ice and the product was filtered off, washed with water until neutral and dried. In this way, 16 g (72% of theory) of 4,5-dichloro-imidazole-2-carboxylic acid isopropylamide with a melting point of 150° C. were obtained.

(b) From 4,5-dichloro-2-dichloromethylene-imidazole ("one-pot process"). 654 g (3 mol) of 4,5-dichloro-2-dichloromethyleneimidazole in a finely powdered form were added incrementally in the course of about one hour, to a mixture, which had been initially introduced, of 783 g (9 mol) of isopropylformamide and 162 g (9 mol) of water, while stirring and cooling slightly, whereupon the internal temperature rose to about 75° C. The reaction mixture was then heated to about 90°-110° C. for a further half hour. After cooling, the product was precipitated in water, filtered off, washed with water and dried. In this way, 566 g (85% of theory) of 4,5-dichloro-imidazole-2-carboxylic acid isopropylamide with a melting point of 150° C. were obtained.

The following 4,5-dichloro-imidazole-2-carboxylic acid amides of the general formula

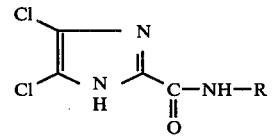

could be obtained in a similar way:

Table 13

| Compound No. | R | Melting point °C. |
|---|---|---|
| 63 | H | 260 |
| 64 | CH$_3$ | 240 |
| 65 | C$_2$H$_5$ | 146 |
| 66 | CH$_2$—CH$_2$OH | 236 |
| 67 | CH$_2$—CH$_2$—CH$_3$ | 140 |
| 68 | CH$_2$—CH$_2$—CONH$_2$ | 194 |
| 69 | CH$_2$—CH$_2$—CH$_2$—CH$_3$ | 105 |
| 70 | —C(CH$_3$)$_3$ | 218 |
| 71 | —C(CH$_3$)$_2$C$_2$H$_5$ | 153 |
| 72 | C$_{12}$H$_{25}$ | 86 |
| 73 | —⟨H⟩ | 186 |

Table 13-continued

| Compound No. | R | Melting point °C. |
|---|---|---|
| 74 | —CH₂—C₆H₅ | 172 |
| 75 | —CH₂—CH₂—C₆H₅ | 149 |

EXAMPLE 28

(a)

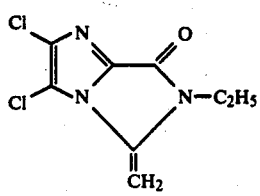
(76a)

21.8 g (0.1 mol) of finely powdered 4,5-dichloro-2-dichloromethylene-imidazole were added to 87 g (1 mol) of N-ethyl-acetamide, whilst stirring, whereupon the temperature of the exothermic reaction rose to about 50° C. After cooling, the product was precipitated with water, filtered off, washed with water and dried. In this way, 14 g (60% of theory) of the bicyclic compound of the formula 76a, which had a melting point of 155° C., were obtained. Colourless needles from hexane.

(b)

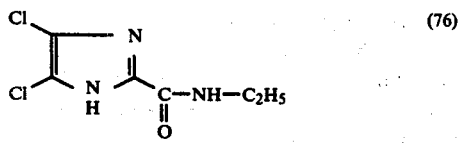
(76)

10 g (0.043 mol) of the cyclic reaction product of (a) and 100 ml of concentrated sulphuric acid were kept at between 60° and 80° C. for about 5 minutes. After cooling, the mixture was poured onto ice and the product was filtered off, washed with water until neutral and dried. In this way, 6 g (67% of theory) of 4,5-dichloro-imidazole-2-carboxylic acid ethylamide with a melting point of 146° C. were obtained.

(c) In a similar manner, it was possible, starting from N-methyl-acetamide, to obtain the bicyclic compound of the formula

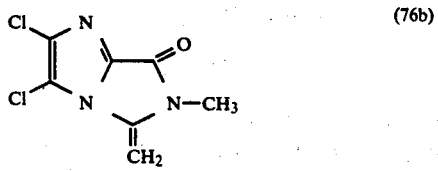
(76b)

which had a melting point of 194° C. Saponification of this compound with concentrated sulphuric acid leads, analogously to (b), to 4,5-dichloroimidazole-2-carboxylic acid methylamide with a melting point of 240° C. (see Example 27).

EXAMPLE 29

(a)

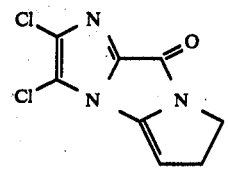
(77a)

21.8 g (0.1 mol) of finely powdered 4,5-dichloro-2-dichloromethylene-imidazole were added incrementally to a mixture of 25 g (0.3 mol) of pyrrolidone and 125 ml of dioxane, whereupon the reaction temperature rose to about 50° C. The mixture was further heated briefly up to about 90° C. and was then cooled and poured into water. After the product had been filtered off, washed with water and dried, 17 g (74% of theory) of the tricyclic compound of the above formula, which had a melting point of 230° C., were obtained.

The same compound was obtained when 4,5-dichloro-2-trichloromethyl-imidazole was employed as the starting material.

Starting from δ-valerolactam and ε-caprolactam respectively, the following tricyclic compounds could be obtained in a similar way:

Table 14

| Compound No. | Formula | Melting Point °C. |
|---|---|---|
| 78a | (structure) | 230° C. |
| 79a | (structure) | 168° C. |

(b) Cl—C=C(Cl)—N(H)—C(=N—)—C(=O)—NH—CH₂—CH₂—CH₂—COOH  (77)

A mixture of 20 g (0.087 mol) of the tricyclic compound of the formula

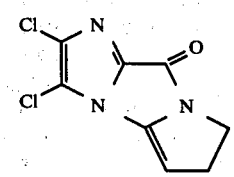
(77a)

and 100 ml of anhydrous formic acid was heated under reflux for 2 hours. After the mixture had been cooled and the product had been filtered off, washed with water and dried, 19 g (82% of theory) of 4,5-dichloro-imidazole-2-carboxylic acid 3-carboxy-n-propylamide with a melting point of 285° C. were obtained. A further 3 g of the carboxylic acid were obtained when the formic acid filtrate was heated under reflux for 6 hours.

The same compound was obtained when the tricyclic starting material was heated with about 10 times the amount of concentrated sulphuric acid to about 100° C. for 15 minutes, the mixture was cooled and discharged onto ice and the product was isolated in the customary way.

The following 4,5-dichloro-imidazole-2-carboxylic acid ω-carboxy-n-alkylamides of the general formula

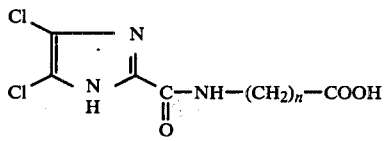

could be obtained in a similar way:

Table 15

| Compound No. | n | melting point °C. |
|---|---|---|
| 78 | 4 | 233 |
| 79 | 5 | 215 |

EXAMPLE 30

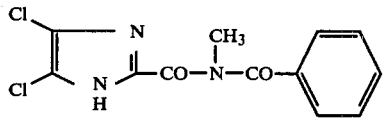 (80)

A solution of 21.8 g (0.1 mol) of 4,5-dichloro-2-dichloromethylene-imidazole was added to a solution of 15 g (0.11 mol) of N-methyl-benzamide in 100 ml of dioxane. The mixture was then heated briefly to the boil and discharged into ice water. The oil which first precipitated out became solid after a few hours. After the product had been filtered off, washed with water and dried, 6.0 g (20% of theory) of N-benzoyl-N-methyl-4,5-dichloro-imidazole-2-carboxylic acid amide with a melting point of 168° C. (acetonitrile) were obtained.

EXAMPLE 31

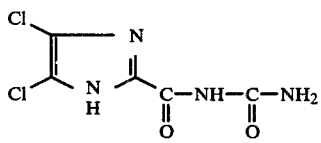 (81)

21.8 g (0.1 mol) of 4,5-dichloro-2-dichloromethyleneimidazole were added to a suspension of 15 g (0.25 mol) of urea in 100 ml of dioxane and the mixture was heated briefly to the boil, while stirring. After cooling, the mixture was poured into water and the product was filtered off, washed with water and dried. In this way, 18 g (67% of theory) of 4,5-dichloro-imidazol-2-oyl-urea, which crystallized with half a mole of dioxane, were obtained. Melting point: >290° C. The dioxane of crystallization could be removed in vacuo at about 140° C. and also by boiling briefly in ethanol.

The following substituted imidazoloylureas of the general formula

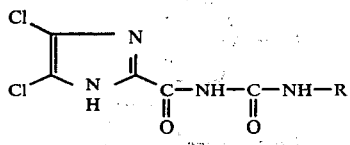

could be obtained in a similar way:

Table 16

| Compound No. | R | Melting point °C. |
|---|---|---|
| 82 | —CH$_3$ | >290 |
| 83 | —CH(CH$_3$)$_2$ | 214 (from acetonitrile) |
| 84 | —C$_6$H$_5$ (phenyl) | 280 (from acetonitrile) |

EXAMPLE 32

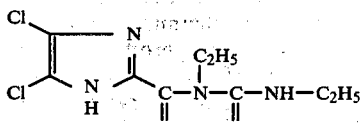 (85)

21.8 g (0.1 mol) of 4,5-dichloro-2-dichloromethyleneimidazole were added to a solution of 26 g (0.22 mol) of N,N'-diethylurea in 150 ml of water and the mixture was heated to 100° C. while stirring. After cooling, the product was filtered off, washed with water and dried. In this way, 18.5 g (66% of theory) of 4,5-dichloro-imidazol-2-oyl-N,N'-diethylurea with a melting point of 159° C. were obtained.

If one part by weight of the reaction product was boiled with about 10 parts by weight of anhydrous formic acid for about 1 hour, the formic acid was then stripped off in vacuo and the residue was recrystallised from acetonitrile, 4,5-dichloroimidazole-2-carboxylic acid N-ethylamide with a melting point of 146° C. (see Example 27) was obtained in good yield.

EXAMPLE 33

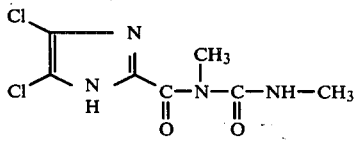 (86)

The above compound was obtained in manner analogous to that of the preceding Example 32. Melting point: 205° C.

As soon as it was attempted to recrystallize the reaction product from boiling acetonitrile, scission took place to give 4,5-dichloroimidazole-2-carboxylic acid N-methylamide with a melting point of 240° C. (see Example 27).

EXAMPLE 34

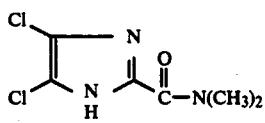 (87)

21.1 g (0.1 mol) of 4,5-dichloro-imidazole-2-thiocarboxylic acid S-methyl ester and a solution of 11 g (0.25 mol) of dimethylamine in 100 ml of water were boiled under reflux for 3 hours. The solution was filtered, cooled and acidified. The crystals which had separated out were filtered off, washed with water and dried. Yield: 9 g (43% of theory) of 4,5-dichloro-imidazole-2-carboxylic acid dimethylamide. Melting point: 244°–246° C. (toluene) (see also Example 24).

EXAMPLE 35

(a)

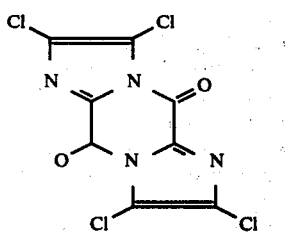 (IV)

40 g (0.55 mol) of dimethylformamide were added dropwise, in the course of about 10 minutes, to a boiling solution of 100 g (0.46 mol) of 4,5-dichloro-2-dichloromethyleneimidazole in 1 l of petroleum ether (boiling range about 60° C.), whereupon a precipitate separated out. After cooling, the petroleum ether was decanted off and the precipitate was stirred with acetone. The product was then filtered off and washed with acetone until the acetone which ran off was pale yellow. In this way, 41 g (55% of theory) of the dimeric ketene of the above formula were obtained in the form of a pale yellow powder with a melting point of >290° C.

(b) A mixture of 500 g (2.51 mol) of 4,5-dichloroimidazole-2-carboxylic acid monohydrate (see Example 16 for its preparation) and 1.8 l of thionyl chloride was stirred under reflux (about 75° C.) for about 24 hours. After cooling, the product was filtered off, washed with a little thionyl chloride and then with petroleum ether and dried. In this way, 362 g (89% of theory) of the dimeric ketene of the above formula were obtained in the form of a pale yellow powder with a melting point of >290° C., which is identical to the product prepared under (a).

(c)

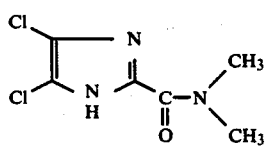 (88)

Gaseous dimethylamine was passed into a suspension of 10.0 g (0.0306 mol) of the dimeric ketene of the formula (IV) in 100 ml of dimethylformamide until a clear, virtually colorless solution had formed. The solution was then evaporated to dryness in vacuo and the residue was recrystallized from chlorobenzene. In this way, 11.5 g (90% of theory) of 4,5-dichloro-imidazole-2-carboxylic acid N,N-dimethylamide with a melting point of 245° C. were obtained.

The following 4,5-dichloro-imidazole-2-carboxamides of the general formula

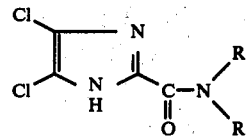

could be obtained in a similar way:

Table 17

| Compound No. | $-N\begin{array}{c}R\\R\end{array}$ | Melting point °C. |
|---|---|---|
| 89 | NH—CH(CH$_3$)(C$_2$H$_5$) | 127 (petroleum ether) |
| 90 | NH—C(CH$_3$)$_2$—C≡CH | 159 (cyclohexane) |
| 91 | NH—CH$_2$—CH$_2$—O—C$_6$H$_5$ | 182 (acetonitrile) |
| 92 | —N(CH$_2$—CH$_2$—CH$_3$)$_2$ | 93 (petroleum ether) |
| 93 | —N(n-C$_4$H$_9$)$_2$ | 90 (petroleum ether) |
| 94 | —N(i-C$_4$H$_9$)$_2$ | 127 (petroleum ether) |
| 95 | —N(pyrrolidine) | 242 (dioxane) |
| 96 | —N(2,3-dihydropyrrole) | >290 (DMF) |
| 97 | —N(hexamethyleneimine) | 186 (acetonitrile) |
| 98 | NH—C$_{12}$H$_{25}$(n) | 86 (petroleum ether) |
| 99 | N(CH$_2$—CH=CH$_2$)$_2$ | 95 (petroleum ether) |
| 100 | NH—C(C$_2$H$_5$)$_2$—C≡CH | 173 (acetonitrile) |
| 101 | NH—CH(C≡CH)(cyclohexyl) | 180 (acetonitrile) |
| 102 | NH—CH$_2$-(furan-2-yl) | 184 (acetonitrile) |
| 103 | NH—CH$_2$-(tetrahydrofuran-2-yl) | 133 (acetonitrile) |

Table 17-continued

| Compound No. | -N(R)(R) | Melting point °C. |
|---|---|---|
| 104 | 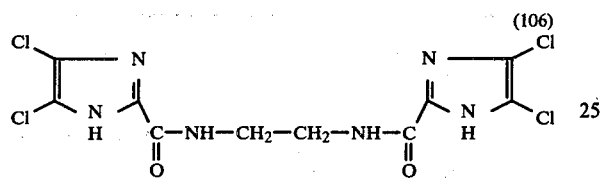 NH—CH₂— | 197 (dioxane) |
| 105 | 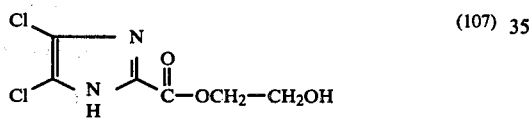 NH—CH₂— | 169 (acetonitrile) |

EXAMPLE 36

It was possible to obtain

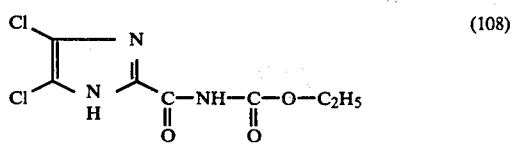
(106)

in a similar way from ethylenediamine. Melting point: 290° C. (from ethanol).

EXAMPLE 37

(107)

A suspension of 10.0 g (0.0306 mol) of the dimeric ketene of the formula (IV) in 100 ml of glycol was heated to about 150° C. until a clear solution had formed. The excess glycol was then removed in vacuo in a rotary evaporator. In this way, 13 g (14% of theory) of 4,5-dichloro-imidazole-2-carboxylic acid 2-hydroxyethyl ester with a melting point of 170° C. were obtained. Colorless crystals from acetonitrile.

EXAMPLE 38

(108)

A solution of 20 g (0.225 mol) of carbamic acid ethyl ester and 21.8 g (0.1 mol) of 4,5-dichloro-2-dichloromethylene-imidazole in 50 ml of dioxane was heated briefly to the boil (about 115° C.) After cooling, the product was precipitated with water, filtered off, washed with water and dried. 15 g (60% of theory) of N-(4,5-dichloroimidazol-2-oyl)-carbamic acid ethyl ester with a melting point of 208° C. (from acetonitrile) were obtained.

EXAMPLE 39

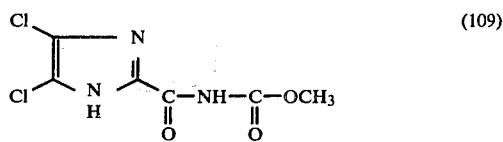
(109)

N-(4,5-Dichloro-imidazol-2-oyl)-carbamic acid methyl ester with a melting point of 247° C. (from ethanol) was obtained in a manner similar to that in Example 38.

EXAMPLE 40

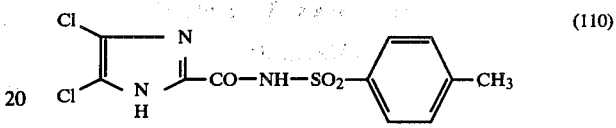
(110)

A solution of 21.8 g (0.1 mol) of 4,5-dichloro-2-dichloromethylene-imidazole in 25 ml of dioxane was added to a suspension of 22 g (0.114 mol) of the sodium salt of p-toluenesulphonamide in 200 ml of water, while stirring. The mixture was then heated briefly to the boil and the product was filtered off while the mixture was still at the boiling point. The precipitate was dried and recrystallized from acetonitrile or toluene. In this way, 14 g (42% of theory) of N-(4-methylphenylsulphonyl)-4,5-dichloroimidazole-2-carboxylic acid amide with a melting point of 238° C. were obtained.

EXAMPLE 41

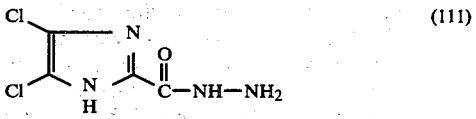
(111)

20.9 g (0.1 mol) of 4,5-dichloro-imidazole-2-carboxylic acid ethyl ester were introduced incrementally, at room temperature, into a mixture of 15 g (0.3 mol) of hydrazine hydrate and 100 ml of ethanol, while stirring. The mixture was boiled for 2 hours and cooled. On cooling, the hydrazine salt of 4,5-dichloro-imidazole-2-carboxylic acid hydrazide precipitated out. This was filtered off, suspended in 100 ml of water and brought into solution by adding dilute sodium hydroxide solution. The solution was acidified with acetic acid. The crystals which had separated out were filtered off, washed with water and dried. Yield: 11 g (56.5% of theory) of 4,5-dichloro-imidazole-2-carboxylic acid hydrazide with a melting point of 210°–211° C. (from ethanol).

EXAMPLE 42

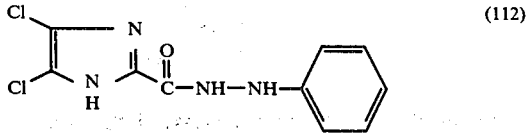
(112)

21.1 g (0.1 mol) of 4,5-dichloro-imidazole-2-thiocarboxylic acid S-methyl ester were boiled with 10.8 g (0.1 mol) of phenylhydrazine in 150 ml of ethanol for 4 hours under reflux. The cooled reaction mixture was mixed with 500 ml of water and the crystals which had separated out were filtered off and dried. 13.5 g (50% of theory) of 4,5-dichloro-imidazole-2-carboxylic acid N'-phenyl-hydrazide with a melting point of 229°-230° C. (from ethyl acetate) were obtained.

EXAMPLE 43

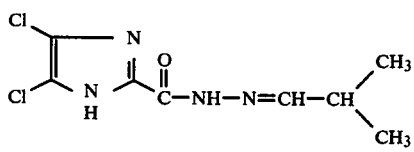 (113)

19.5 g (0.1 mol) of 4,5-dichloro-imidazole-2-carboxylic acid hydrazide and 7.2 g (0.1 mol) of isobutyraldehyde were boiled in 150 ml of ethanol with the addition of 1 ml of concentrated hydrochloric acid for 3 hours under reflux. After the solvent had been distilled off, 4,5-dichloroimidazol-2-oyl-isobutyrohydrazone remained in quantitative yield. Melting point: 172°-174° C. (from toluene).

EXAMPLE 44

When an equimolar amount of salicylaldehyde is employed in place of isobutyraldehyde in Example 43, the corresponding hydrazone of the formula

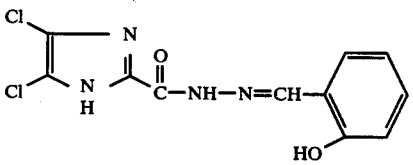 (114)

was obtained. Melting point: 300° C. (from glycol monomethyl ether).

EXAMPLE 45

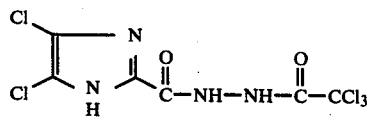 (115)

19.5 g (0.1 mol) of 4,5-dichloro-imidazole-2-carboxylic acid hydrazide and 10.1 g (0.1 mol) of triethylamine were initially introduced into 150 ml of dioxane. 18.2 g (0.1 mol) of trichloroacetyl chloride were added dropwise to this mixture at 10°-15° C., while stirring. The mixture was stirred for a further 2 hours at room temperature, 500 ml of water were added and the crystals which had separated out were filtered off. Yield: 26.2 g (77% of theory) of N-(4,5-dichloroimidazol-2-yl)-N'-trichloroacetyl-hydrazine. Melting point: 192°-194° C. (ethyl acetate).

EXAMPLE 46

With an equimolar amount of chloroformic acid ethyl ester in place of trichloroacetyl chloride in Example 45, the process gave N'-(4,5-dichloro-imidazol-2-oyl)-carbazic acid ethyl ester of the formula:

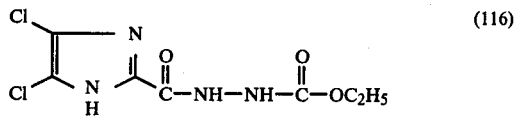 (116)

Melting point: 235°-237° C. (butanol).

EXAMPLE 47

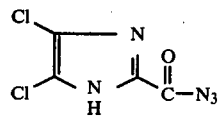 (117)

(a) 19.5 g (0.1 mol) of 4,5-dichloro-imidazole-2-carboxylic acid hydrazide were dissolved in 150 ml of 5% strength aqueous hydrochloric acid. A solution of 7 g (about 0.1 mol) of sodium nitrite in a little water was added dropwise at 0°-5° C., while stirring vigorously. The mixture was stirred for a further 1 hour at the same temperature and filtered and the crystals were washed with water and dried at room temperature. The yield of 4,5-dichloro-imidazole-2-carboxylic acid azide was virtually quantitative. The IR spectrum and the mass spectrum confirmed the structure. The compound deflagrated at about 175° C., without melting.

(b) A solution of 218 g (1.0 mol) of 4,5-dichloro-2-dichloromethylene-imidazole in 250 of dioxane was added dropwise in the course of about 20 minutes, at between about 10°-30° C., to a solution, which had been initially introduced, of 80 g (1.23 mol) of sodium azide in 1 liter of water, while stirring and cooling with ice. The product was then filtered off, washed with water and dried. In this way, 196 g (95% of theory) of 4,5-dichloro-imidazole-2-carboxylic acid azide, which was identical to the product prepared under (a), were obtained.

EXAMPLE 48

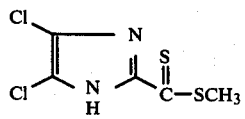 (118)

25.45 g (0.1 mol) of 4,5-dichloro-2-trichloromethylimidazole were introduced incrementally, at room temperature, into a solution, which had been saturated with hydrogen sulphide, of 24 g (0.5 mol) of sodium hydroxide in 150 ml of methanol, while stirring vigorously. The mixture was stirred for a further 2 hours at room temperature and for 2 hours at 50° C. The sodium chloride which had separated out was filtered off and 14.2 g (0.1 mol) of methyl iodide were then added dropwise to the filtrate. The mixture was stirred for a further 1 hour at room temperature and for 1 hour at 40°-45° C. and then evaporated in vacuo. The residue was dissolved in water, the solution was acidified and the crystals which had separated out were filtered off, washed with water and dried. Yield: 19.7 g (80% of theory) of 4,5-dichloro-imidazole-2-dithiocarboxylic acid methyl ester. Melting point: 122°-124° C. (wash benzine).

EXAMPLE 49

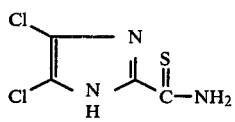 (119)

16.2 g (0.1 mol) of 4,5-dichloro-imidazole-2-carboxylic acid nitrile were dissolved in 125 ml of pyridine. 10.1 g (0.1 mol) of triethylamine were added and dry hydrogen sulphide was passed in for 5 hours, starting at room temperature and gradually raising the temperature to 50° C. The reaction mixture was evaporated in vacuo, the residue was dissolved in water, the solution was acidified with hydrochloric acid and the crystals which precipitated out were filtered off. The crude product contained a little elementary sulphur and was freed from this by recrystallizing it from dilute sodium hydroxide solution, filtering and acidifying again. Yield: 16.2 g (82.5% of theory) of 4,5-dichloro-imidazole-2-thiocarboxylic acid amide. Melting point: 171°–173° C. (toluene).

EXAMPLE 50

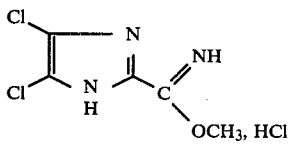 (120)

16.2 g (0.1 mol) of 4,5-dichloro-imidazole-2-carboxylic acid nitrile were suspended in 150 ml of methanol. Dry hydrogen chloride was passed in at 10°–15° C. until the suspension was saturated. The undissolved material was filtered off, the filtrate was evaporated in vacuo and the residue was pressed off on clay and dried in a desiccator over KOH, Yield: 13 g (56.5% of theory) of 4,5-dichloro-imidazole-2-iminocarboxylic acid methyl ester hydrochloride. Melting point:>250° C.

EXAMPLE 57

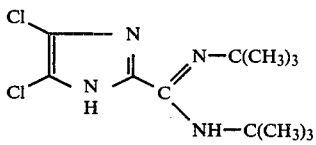 (121)

21.8 g (0.1 mol) of 4,5-dichloro-2-dichloromethylene-imidazole were introduced into 73 g (0.5 mol) of 50% strength aqueous tert.-butylamine, while stirring, and the reaction mixture warmed to about 80° C. After cooling, the product was precipitated in water and filtered off, washed with water and dried. In this way, 24 g (80% of theory) of 4,5-dichloro-imidazole-2-carboxylic acid N,N'-di-tert.-butylamidine were obtained. Dense pale yellow crystals with a melting point of 169° C. from ethanol/water.

The following 4,5-dichloro-imidazole-2-carboxylic acid amidines of the general formula

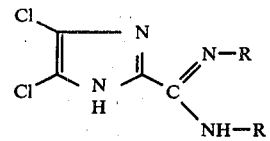

could be obtained in a similar way:

Table 18

| Compound No. | R | Melting point °C. |
|---|---|---|
| 122 | CH$_3$ | 280 |
| 123 | C$_2$H$_5$ | 223 (from methanol) |
| 124 | —CH(CH$_3$)$_2$ | |

EXAMPLE 55

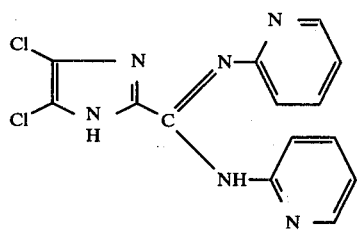 (125)

A mixture of 18.8 g (0.2 mol) of α-amino-pyridine and 30.3 g (0.3 mol) of triethylamine was added dropwise, at 10°–15° C., to a solution of 25.4 g (0.1 mol) of 4,5-dichloro-2-trichloromethyl-imidazole in 200 ml of dioxane, while cooling. The mixture was stirred for a further 2 hours at room temperature, 1 l of water was added and the resulting mixture was rendered slightly acid with acetic acid. The crystals which had separated out were filtered off, washed with water and dried. 25.4 g (77% of theory) of 4,5-dichloro-imidazole-carboxylic acid N,N'-di-pyrid-2-yl-amidine were obtained. Melting point: 199°–200° C. (from ethyl acetate/ligroin).

C$_{14}$H$_{10}$Cl$_2$N$_6$ (333.2) Calculated: 21.3% Cl, 25.23% N; Found: 20.8 Cl, 25.0 N

EXAMPLE 56

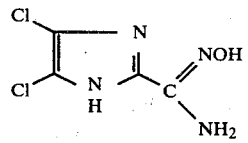 (126)

16.2 g (0.1 mol) of 4,5-dichloro-imidazole-2-carboxylic acid nitrile were suspended in 120 ml of ethanol. 8 g (0.115 mol) of hydroxylammonium chloride were added to this suspensions and 14 g of potassium carbonate were then added in small portions. The mixture was heated to the boil and boiled until no further evolution of CO$_2$ took place. The salt-like constituents were filtered off and washed with ehtanol and the combined filtrates were evaporated in vacuo. The residue was recrystallized from ethyl acetate. 12.2 g (63% of theory) of 4,5-dichloro-imidazole-2-carbamide-oxime were obtained. Melting point: 270°–275° C.

$C_4H_4Cl_2N_4O$ (195.0) Calculated: 36.36% Cl, 28.74% N, Found: 36.9 Cl, 28.3 N

EXAMPLE 57

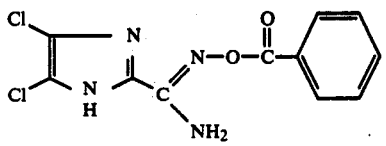 (127)

19.5 g (0.1 mol) of 4,5-dichloro-imidazole-2-carbamide-oxime and 10.1 g (0.1 mol) of triethylamine were dissolved in 150 ml of dioxane. 14.05 g (0.1 mol) of benzoyl chloride were added dropwise to this solution at 15°–20° C. The mixture was stirred for a further 1 hour at room temperature and for 2 hours at 50° C. and was then introduced into 500 ml of water. The crystals which had separated out were filtered off, washed with water and dried. 18 g (60.2% of theory) of 4,5-dichloro-imidazole-2-carbamide-O-benzoyl-oxime were obtained. Melting point: 177°–178° C. (from toluene).

EXAMPLE 58

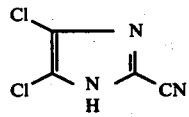 (128)

25.4 g (0.1 mol) of 4,5-dichloro-2-trichloromethyl-imidazole were introduced in small portions into 200 ml of ethanol saturated with ammonia, while cooling with ice and stirring vigorously. The mixture was stirred for a further ½ hour at 50° C. The insoluble constituents were filtered off and the filtrate was evaporated in vacuo. The combined residues were dissolved in hot water. The reaction product precipitated out on acidification with dilute hydrochloric acid. This product was filtered off, washed with water and dried. Yield: 14.6 g (90% of theory). Melting point: 187°–180° C. (from toluene).

EXAMPLE 59

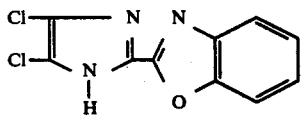 (129)

10.9 g (0.1 mol) of 2-aminophenol and 40.4 g (0.4 mol) of triethylamine were dissolved in 200 ml of dioxane. 25.4 g (0.1 mol) of 4,5-dichloro-2-trichloromethyl-imidazole were introduced in portions while cooling to 15°–20° C. The mixture was stirred for a further ½ hour at room temperature and for 2 hours at 60°–70° C. The reaction mixture was then introduced into 1 liter of water and acidified with dilute hydrochloric acid and the precipitate was filtered off. The latter was washed with water and dried. Yield: 12 g (47.2% of theory) of 2-(4,5-dichloro-imidazol-2-yl)-benzoxazole, melting point: 196°–198° C. (from ethanol).

EXAMPLE 60

By the process of Example 59, 2-(4,5-dichloro-imidazol-2-yl)-benzimidazole of the formula

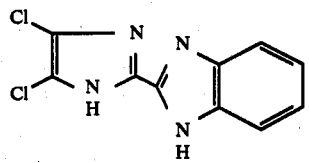 (130)

[melting point: 300° C. (from butanol)] was obtained using 10.8 g (0.1 mol) of phenylenediamine in place of 2-amino-phenol.

EXAMPLE 61

Similarly, 2-(4,5-dichloro-imidazol-2-yl)-imidazoline of the formula

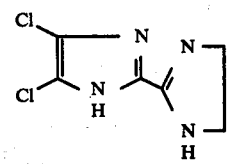 (131)

[melting point 260° C. (ethyl acetate/ligroin)] was obtained using 6 g (0.1 mol) of ethylenediamine in place of 2-amino-phenol in the process of Example 59.

EXAMPLE 62

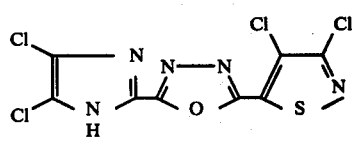 (132)

21.8 g (0.1 mol ) of 4,5-dichloro-2-dichloromethylene-imidazole was added to 23.5 g (0.11 mol) of 3,4-dichloro-isothiazole-5-carboxylic acid hydrazide (melting point 156° C.; prepared in the customary manner from 3,4-dichloro-isothiazole-5-carboxylic acid which is described in U.S. Pat. No. 3,341,547) in 300 ml of dioxane, while stirring, whereupon the reaction mixture warmed to about 50° C. and, at the same time, a voluminous precipitate separated out. After subsequently heating briefly to 100° C., the mixture was cooled and the precipitate was filtered off, washed with dioxane and dried. In this way 33 g (84% of theory) of an intermediate product which had the empirical formula $C_8H_2Cl_5N_5OS$ and for which one of the two tautomeric formulae

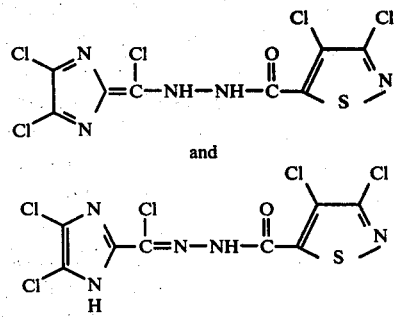

and was probable, were obtained. This intermediate product melted at 205° C. with the evolution of HCl and then solidified again. During this process, a quantitative conversion into the oxadiazole derivative of the above formula, which melted at 266° C., had taken place.

The same oxdiazole derivative was obtained by a "one pot process" when the reaction was carried out at temperatures of up to 200°–250° C. in a high-boiling solvent, such as, for example, 1,2,4-trichlorobenzene or 1-chloronaphthalene, instead of dioxane.

The following imidazolyl-oxadiazoles of the general formula

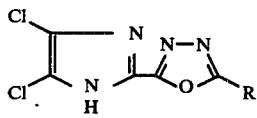

could be obtained in a similar way:

Table 19

| Compound No. | R | Melting point °C. |
|---|---|---|
| 133 | phenyl | >290 |
| 134 | -C6H4-NO2 | >290 |
| 135 | furyl (O) | 262 |
| 136 | pyridyl (N) | 290 |

EXAMPLE 67

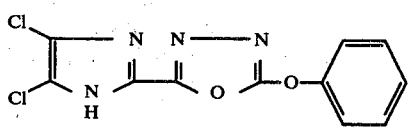

16.7 g (0.11 mol) of carbazic acid phenyl ester were added in portions, at room temperature, to a solution of 25.4 g (0.1 mol) of 4,5-dichloro-2-trichloromethyl-imidazole in 200 ml of dioxane. After the slightly exothermic reaction had subsided, the mixture was gradually warmed to the boil and boiled for a further 2 hours under reflux. It was then cooled to room temperature and 20.2 g (0.2 mol) of triethylamine were added dropwise. The mixture was stirred for a further 2 hours at 50° C., the insoluble constituents were filtered off and the filtrate was evaporated in vacuo. The residue was treated with water and the product was filtered off, washed with water and dried. 21.5 g (72.5% of theory) of 2-(4,5-dichloro-imidazol-2-yl)-5-phenoxy-1,3,4-oxadiazole were obtained. Melting point: 109° C. (from toluene).

EXAMPLE 68

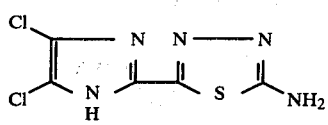

9.1 g (0.1 mol) of thiosemicarbazide and 40.4 g (0.4 mol) of triethylamine were stirred in 200 ml of ethanol until a clear solution had formed. 25.4 g (0.1 mol) of 4,5-dichloro-2-trichloromethyl-imidazole were added to this solution incrementally at 0°–5° C., while stirring. The mixture was stirred for a further 1 hour with cooling, for 1 hour at room temperature and for 1 hour at 50° C. After cooling, the amine-hydrochloride was filtered off and the filtrate was evaporated in vacuo. The residue was treated with water, the mixture was acidified with hydrochloric acid and the product was filtered off, washed with water and dried. 18 g (76.5% of theory) of 2-(4,5-dichloro-imidazol-2-yl)-5-amino-1,3,4-thiadiazole were obtained. Melting point: 147° C. (with decomposition) (from ethyl acetate/ligroin).

EXAMPLE 69

When semicarbazide-hydrochloride was employed in place of thiosemicarbazide in the presence of 5 times the molar amount of triethylamine, the process of Example 68 gave 3-(4,5-dichloroimidazol-2-yl)-1,2,4-triazol-5-one of the formula

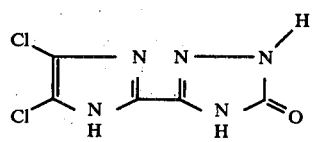

Melting point: 176°–178° C. (from ethyl acetate/ligroin).

EXAMPLE 70

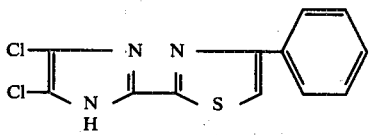

19.6 g (0.1 mol) of 4,5-dichloro-imidazol-2-thiocarboxylic acid amide and 15.5 g (0.1 mol) of ω-chloroacetophenone were dissolved in 200 ml of acetonitrile, 30 g of potassium carbonate were added and the mixture was gradually heated to the boil. After boiling for 5 hours, the insoluble constituents were filtered off and the filtrate was evaporated in vacuo. The combined residues were introduced into water. Hydrochloric acid was then added until the mixture gave a weakly acid reaction and the insoluble matter was filtered off, washed with water and dried.

Yield: 18 g (61% of theory); melting point: 159°–160° C. (from wash benzine).

EXAMPLE 71

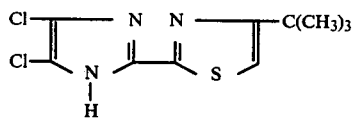 (141)

Using bromopinacoline (17.9 g) in place of chloroacetophenone, the same procedure as in Example 48 gave 21 g (76% of theory) of 2-(4,5-dichloro-imidazol-2-yl)-4-tert.-butyl-thiazole. Melting point: 157°–158° C. (wash benzine).

EXAMPLE 72

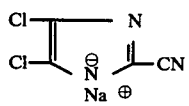 (142)

16.2 g (0.1 mol) of 4,5-dichloro-imidazole-2-carboxylic acid nitrile were dissolved in 150 ml of ethanol with warming. A solution of 2.3 g (0.1 mol) of sodium in a little ethanol was added to this solution. After stirring briefly, the solution was evaporated in vacuo. The water-soluble sodium salt remained in quantitative yield. Melting point:>250° C.

EXAMPLE 73

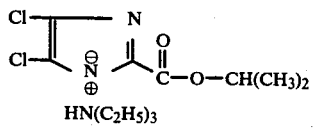 (143)

22.3 g (0.1 mol) of 4,5-dichloro-imidazole-2-carboxylic acid isopropyl ester were dissolved in 150 ml of toluene with slight warming. 10.1 g (0.1 mol) of triethylamine were added to this solution. The mixture was stirred for ½ hour at room temperature and cooled to 0° C. and the crystalline product was filtered off and dried. The water-soluble triethylammonium salt was obtained in quantitative yield. Melting point:>250° C.

EXAMPLE 74

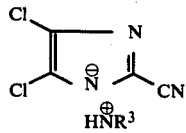 (144)

16.2 g (0.1 mol) of 4,5-dichloro-imidazole-2-carboxylic acid nitrile were dissolved in 150 ml of ethanol. 0.1 mol of an amine were added to this solution and the solvent was then evaporated off in vacuo. The amine salt remained as the residue in quantitative yield.

Table 2

| Compound | Salt | Melting Point, °C. |
|---|---|---|
| 144 | triethylammonium | 38–40 |
| 145 | butylammonium | 122–124 |
| 146 | pyridinium | 74–76 |
| 147 | N,N-dimethyl-benzyl ammonium | 90–92 |
| 148 | dibutylammonium | 56–58 |
| 149 | morpholinium | 144–146 |
| 150 | tris-(2-hydroxy-ethyl)-ammonium | 102 |

Table 2-continued

EXAMPLE 75

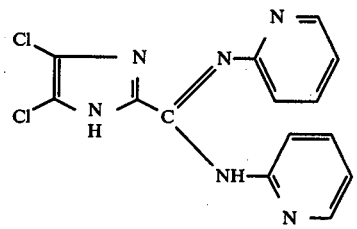 (125)

A mixture of 18.8 g (0.2 mol) of α-amino-pyridine and 30.3 g (0.3 mol) of triethylamine was added dropwise, at 10°–15° C., to a solution of 25.4 g (0.1 mol) of 4,5-dichloro-2-trichloromethyl-imidazole in 200 ml of dioxane, while cooling. The mixture was stirred for a further 2 hours at room temperature, 1 liter of water was added and the mixture was rendered slightly acid with acetic acid. The crystals which had separated out were filtered off, washed with water and dried. 25.4 g (77% of theory) of 4,5-dichloro-imidazole-2-carboxylic acid N,N'-di-pyrid-2-yl-amidine were obtained. Melting point: 199°–200° C. (from ethyl acetate/ligroin).

EXAMPLE 76

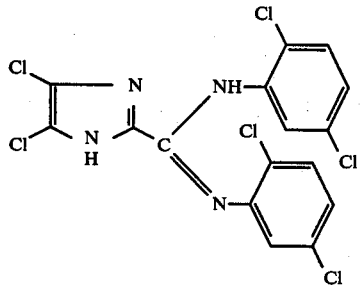 (152)

16.2 g (0.1 mol) of 2,5-dichloroaniline and 10.1 g (0.1 mol) of triethylamine were added, at about 20° C., to a solution of 10.9 g (0.05 mol) of 4,5-dichloro-2-dichloromethylene-imidazole in 50 ml of dioxane. The mixture was then heated briefly to about 100° C. and cooled and the product was precipitated in water, filtered off, washed with water and dried. 22 g (94% of theory) of 4,5-dichloro-imidazole-2-carboxylic acid N,N'-di-(2,5-dichlorophenyl)-amidine were obtained. Melting point: 212° C. (from toluene).

The following 4,5-dichloro-imidazole-2-carboxylic acid N,N'-diarylamidines of the general formula

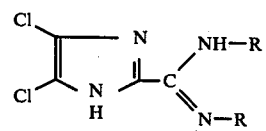

could be obtained in a similar way.

Table 21

| Compound No. | R | Melting point, °C. |
|---|---|---|
| 153 | 2,4-dichlorophenyl | 204 (toluene) |
| 154 | 2,6-dichlorophenyl | 230 (benzene) |
| 155 | 3-trifluoromethylphenyl | 210 (acetonitrile) |
| 156 | 2-chlorophenyl | 220 (acetonitrile) |
| 157 | 3-chloro-4-trifluoromethylphenyl | 212 (toluene) |
| 158 | 3,4-dichlorophenyl | 255 (chlorobenzene) |
| 159 | 3,5-bis(trifluoromethyl)phenyl | 181 (cyclohexane) |
| 160 | 2,4-dimethylphenyl | 290 (chlorobenzene) |
| 161 | 4-trifluoromethylphenyl | 285 (acetonitrile) |
| 162 | 4-fluorophenyl | 285 (chlorobenzene) |
| 163 | 2-chloro-4-trifluoromethylphenyl | 210 (acetonitrile) |
| 164 | 3-bromophenyl | 242 (chlorobenzene) |
| 165 | 2-methyl-4-chlorophenyl | 240 (chlorobenzene) |
| 166 | 2-chloro-4-trifluoromethoxyphenyl | 190 (acetonitrile) |
| 167 | 3,5-dichlorophenyl | 255 (chlorobenzene) |
| 168 | 3-trifluoromethyl-4-chlorophenyl | 127 (cyclohexane) |
| 169 | 2,3-dichlorophenyl | 229 (chlorobenzene) |
| 170 | 4-trifluoromethoxyphenyl | 242 (acetonitrile) |
| 171 | 4-trifluoromethylthiophenyl | 253 (acetonitrile) |
| 172 | 2-chloro-4-trifluoromethylphenyl | 216 (acetonitrile) |
| 173 | 4-(1,1,2-trifluoro-2-chloroethoxy)phenyl —O—CF$_2$—CHClF | 200 (acetonitrile) |
| 174 | 2,2,2-trifluoro-1-trifluoromethyl-1-(2-hydroxyphenyl) cyclic | 250 (acetonitrile) |

EXAMPLE 77

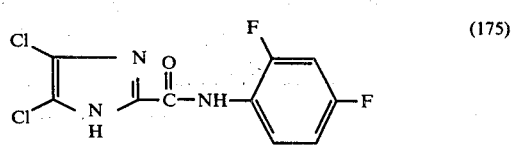 (175)

A suspension of 16.3 g (0.05 mol) of the dimeric ketene of the formula (IV) (see example No. 107 for its preparation) in 100 ml of dimethylformamide was treated with 14 g (0.11) of 2,4-difluoroaniline to 145°–155° C. for about 5 minutes, whereupon a solution formed. After cooling, the product was precipitated in water, filtered off, washed with water and dried. In this way 24 g (83% of theory) of 4,5-dichloro-imidazole-2-carboxylic acid N-(2,4-difluorophenyl)-amide were obtained. Melting point: 290° C. (from o-dichlorobenzene).

EXAMPLE 78

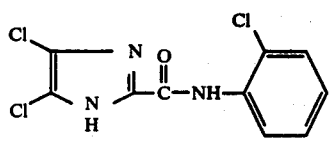 (176)

21.8 g (0.1 mol) of finely powdered 4,5-dichloro-2-dichloromethylene-imidazole were added, at room temperature, to a mixture of 16 g (0.125 mol) of finely powdered 2-chloroaniline, 100 ml of water and 15 g (about 0.15 mol) of 37% strength aqueous hydrochloric acid, while stirring, and the mixture was then heated to about 100° C. for about 1 hour. After the solution had been cooled and the product had been filtered off, washed with water and dried, 21.5 g (74% of theory) of 4,5-dichloroimidazole-2-carboxylic acid 2-chloroanilide with a melting point of 244° C. were obtained. The substance crystallized as colorless needles from chlorobenzene or 1,2-dichlorobenzene. The same compound was also obtained starting from 4,5-dichloro-2-trichloromethylimidazole.

The following 4,5-dichloro-imidazole-2-carboxylic acid anilides of the general formula could be obtained in a similar manner:

Table 22

| Compound No. | R | Melting point, °C. |
|---|---|---|
| 177 | 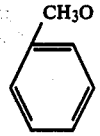 | 243 (acetonitrile) |
| 178 | 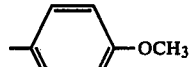 CH₃ | 195 (toluene) |
| 179 | 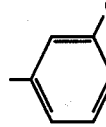 —C₂H₅ | 205 (chlorobenzene or acetonitrile) |
| 180 | 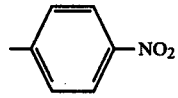 CF₃ | 200 (toluene) |
| 181 | 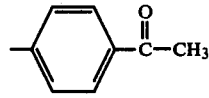 CH₃O | 290 (o-dichlorobenzene) |
| 182 | 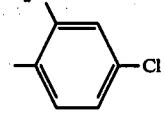 —OCH₃ | 221 (o-dichlorobenzene) |
| 183 | 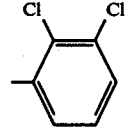 Cl | 258 (chlorobenzene) |
| 184 | 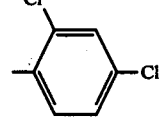 —NO₂ | >290 (o-dichlorobenzene) |
| 185 | 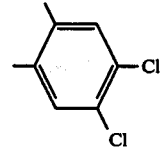 —C(O)—CH₃ | 290 (o-dichlorobenzene) |
| 186 | 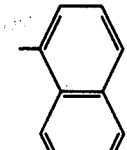 O₂N, Cl | 290 (o-dichlorobenzene) |
| 187 | Cl, Cl  | 260 (o-dichlorobenzene) |
| 188 | Cl, Cl | 260 (o-dichlorobenzene) |
| 189 | Cl, Cl, Cl | >290 (o-dichlorobenzene) |
| 190 | (naphthyl) | 290 |
| 191 | Cl | 264 (chlorobenzene) |

Table 22-continued

| Compound No. | R | Melting point, °C. |
|---|---|---|
| 192 | 4-CF₃, 2-Cl-phenyl | 265 (toluene) |
| 193 | 2-Cl, 4-CF₃-phenyl | 257 (chlorobenzene) |
| 194 | 2,3-diCl-phenyl | 280 (o-dichlorobenzene) |
| 195 | 3,5-di(CF₃)-phenyl | 249 (acetonitrile) |
| 196 | 2,4-di(CH₃)-phenyl | 244 (chlorobenzene) |
| 197 | 2-CH₃, 4-Cl-phenyl | 259 (chlorobenzene) |
| 198 | 3-CF₃, 4-CF₃-phenyl | 228 (acetonitrile) |
| 199 | 4-CF₃-phenyl | 266 (acetonitrile) |
| 200 | 4-F-phenyl | >290 (dioxane) |
| 201 | 2,4-diCl-phenyl | 290 (chlorobenzene) |
| 202 | 3-Br-phenyl | 280 |
| 203 | 3-Cl, 4-OCF₃-phenyl | 205 (acetonitrile) |
| 204 | 3-Cl, 4-SCF₂Cl-phenyl | 244 (acetonitrile) |
| 205 | 3-CF₃, 4-Cl-phenyl | 215 (acetonitrile) |
| 206 | 3,5-diCl-phenyl | >290 (dioxane) |
| 207 | 4-OCF₃-phenyl | 202 (acetonitrile) |
| 208 | 4-SCF₃-phenyl | 254 (acetonitrile) |
| 209 | 2-CF₃, 4-Cl-phenyl | 211 (acetonitrile) |
| 210 | 2-CF₃, 3-Cl-phenyl | 236 (acetonitrile) |
| 211 | 2-CHF₂, 3-Cl-phenyl | 254 (acetonitrile) |
| 212 | 4-OCF₂—CHClF-phenyl | 202 (acetonitrile) |

Table 22-continued

| Compound No. | R | Melting point, °C. |
|---|---|---|
| 213 | 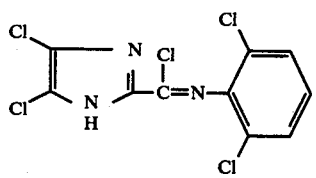 | 218 (acetonitrile) |
| 214 | NC—⟨ ⟩—CF₃ | 280 (acetonitrile) |
| 215 | CF₃—⟨ ⟩—CN | 265 (toluene) |

EXAMPLE 79

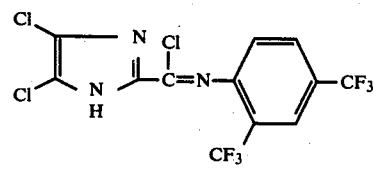 (216)

A solution of 109 g (0.5 mol) of 4,5-dichloro-2-dichloromethylene-imidazole in 125 ml of dioxane was added dropwise in the course of about 10–15 minutes to a mixture of 81 g (0.5 mol) of finely powdered 2,6-dichloroaniline, 500 ml of water and 75 g (about 0.75 mol) of 37% strength aqueous hydrochloric acid at 55°–60° C., while stirring. After stirring for about a further 2 hours, the product was filtered off, washed with water and dried. 159 g (92% of theory) of 4,5-dichloro-imidazole-2-carboxylic acid N-(2,6-dichlorophenyl)-imide-chloride were obtained. Long needles with a decomposition point of about 200° C. from acetonitrile or from chloroform.

In the same manner from 2,4-di(trifluoromethyl)-aniline and 4,5-dichloro-2-dichloromethylene-imidazole there was obtained 4,5-dichloro-imidazole-2-carboxylic acid, N-[2,4-di-(trifluoromethyl)-phenyl]-imide-chloride, melting point 170° C. (cyclohexane) of the formula (217)

EXAMPLE 80

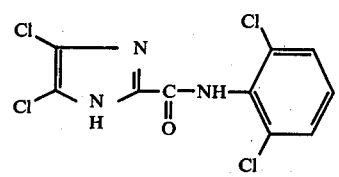 (218)

25 g (0.73 mol) of 4,5-dichloro-imidazole-2-carboxylic acid N-(2,6-dichlorophenyl)-imide-chloride (see Example 79 for the preparation) were stirred with 125 g of concentrated sulphuric acid for about 5 hours. The mixture was then discharged onto ice and the product was filtered off, washed with water until neutral and dried. (18.5 g (78% of theory) of 4,5-dichloro-imidazole-2-carboxylic acid 2,6-dichloroanilide were obtained. Melting point 206° C. (from acetonitrile

EXAMPLE 81

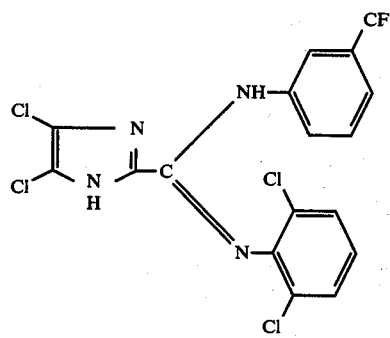 (219)

34.4 g (0.01 mol) of finely poweered 4,5-dichloroimidazole-2-carboxylic acid N-(2,6-dichlorophenyl)-imide-chloride (see Example 79) were added to 19 g (0.12 mol) of 3-trifluoromethyl-aniline in 500 ml of water and the mixture was heated to about 100° C. for 5–10 minutes, while stirring. After cooling, the product was filtered off, washed with water and dried. 46 g (98% of theory) of 4,5-dichloro-imidazole-2-carboxylic acid N-(2,6-dichlorophenyl)-N'-(3-trifluoromethylphenyl)-amidine were obtained.

The following amidines of the general formula

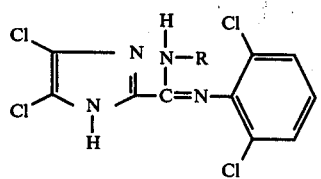

could be obtained in a similar way.

Table 23

| Compound No. | R | Melting point °C. |
|---|---|---|
| 220 | ⟨ ⟩—Cl, CF₃ | 205 (acetonitrile) |

Table 23-continued

| Compound No. | R | Melting point °C. |
|---|---|---|
| 221 | 2-Cl, -S—CF₂Cl phenyl | 165 (acetonitrile) |
| 222 | 4-CF₃ phenyl | 212 (acetonitrile) |
| 223 | 2,4-Cl₂ phenyl | 192 (acetonitrile) |
| 224 | 3,5-(CF₃)₂ phenyl | 195 (acetonitrile) |
| 225 | 2-Cl, 4-CF₃ phenyl | 190 |
| 226 | 2-Cl, 4-CF₃ phenyl | 170 |
| 227 | 2-CF₃, 4-Cl phenyl | 158 |
| 228 | 2,3-Cl₂ phenyl | 250 (acetonitrile/dioxane) |
| 229 | 2,4-Cl₂ phenyl | 182 (acetonitrile) |
| 230 | 2-Cl, 4-OCF₃ phenyl | 200 (acetonitrile) |
| 231 | 4-OCF₂—CHClF phenyl | 165 (acetonitrile) |
| 232 | (structure with F, O) | 187 (acetonitrile) |

EXAMPLE 82

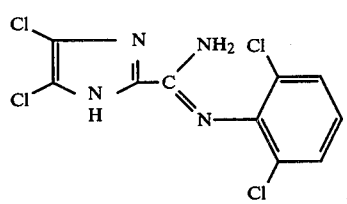

(233)

20 g (0.06 mol) of finely powdered 4,5-dichloro-imidazole-2-carboxylic acid N-(2,6-dichlorophenyl)-imide-chloride (see Example No. 79) were introduced into 200 ml of concentrated aqueous ammonia, while stirring. After stirring for about a further 1 hour, the product was filtered off, washed with water and dried. 15 g (77% of theory) of 4,5-dichloro-imidazole-2-carboxylic acid N-(2,6-dichlorophenyl)-amidine were obtained. Melting point 270° C. (from acetonitrile).

EXAMPLE 83

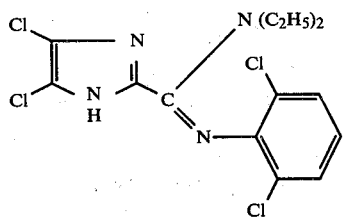

(234)

7.5 of diethylamine were added at 20°–30° C. to a solution of 17.2 g (0.05 mol) of 4,5-dichloro-imidazole-2-carboxylic acid N-(2,6-dichlorophenyl)-imide-chloride (see Example 79). in 200 ml of dioxane. After stirring for a further 1 hour the product was precipitated in water, neutralized with dilute hydrochloric acid, filtered off, washed with water and dried. 18.5 g (97% of theory) of 4,5-dichloro-imidazole-2-carboxylic acid N-(2,6-dichlorophenyl)-N', N'-diethyl-amidine were obtained. Melting point 175° C. (from acetonitrile).

EXAMPLE 84

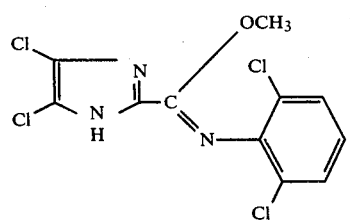

(235)

34.4 g (0.1 mol) of finely powdered 4,5-dichloro-imidazole-2-carboxylic acid N-(2,6-dichlorophenyl)-imide-chloride (see Example 79) were introduced, at about 20° C. into a solution of 10 g (0.18 mol) of potassium hydroxide in 400 ml of methanol, whilst stirring and cooling. After stirring further for about 1 hour at 20° C., the product was precipitated in water, neutralized with dilute hydrochloric acid, filtered off, washed with water and dried. 26 g (77% of theory) of 4,5-dichloro-imidazole-2-carboxylic acid (2,6-dichlorophenylimido)-methyl ester were obtained. Melting point 203° C. (from benzene).

EXAMPLE 85

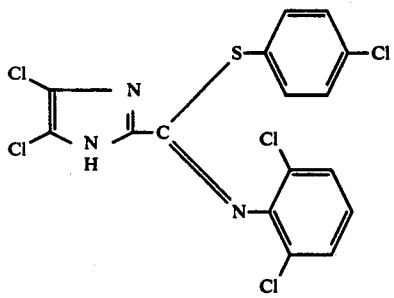

(236)

17.2 g (0.05 mol) of 4,5-dichloro-imidazole-2-carboxylic acid N-(2,6-dichlorophenyl)-imide-chloride (see Example 79) in a finely powdered form were added, at 20°–25° C., to a solution of 4 g (0.071 mol) of potassium hydroxide and 9 g (0.062 mol) of 4-chloro-thiophenol in 200 ml of water, while stirring. After stirring for about a further 5 hours at 20°–25° C., the product was filtered off, washed with water and dried. 18 g (80% of theory) of 4,5-dichloro-imidazole-2-carboxylic acid (2,6-dichlorophenylimido)-(4-chlorophenyl) thioester were obtained. Melting point 190° C. (from a little isopropanol).

EXAMPLE 86

The following compounds could be prepared by a procedure analogous to that described in Example 72:

Table 24

| Compound No. | Formula |
|---|---|
| 237 | 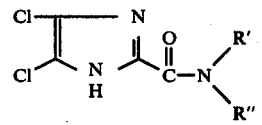 |
| 238 | Cl—C=C(Cl)—N—N=C—C(=O)—NH—C$_3$H$_7$i, Na$^\oplus$ |
| 239 | Cl—C=C(Cl)—N—N=C—C(=O)—N(CHO)—C$_3$H$_7$i, Na$^\oplus$ |

As employed hereinabove, unless otherwise stated, the preferred heterocyclic radicals include those from pyridine, piperidine, morpholine, quinoline, imidazole, pyrazole, diazines, triazines, oxazoles, oxazines, thiazoles, thiazines, oxathiazoles, oxathiazines, furane, thiophene, and the like.

The temperature ranges recited in the general outlines of the process for synthesis are approximate.

It will be appreciated that the instant specification and examples are set forth by way of illustration and not limitation, and that various modifications and changes may be made without departing from the spirit and scope of the present invention.

What is claimed is:

1. A 4,5-dichloro-imidazole-2-carboxylic acid amide of the formula

Cl—C=C(Cl)—N(H)—N=C—C(=O)—N(R')(R'')

wherein R' and R'' independently of one another denote hydrogen, $C_{1-12}$-alkyl optionally substituted by CN, OH, $CONH_2$, COOH, phenyl or N-4,5-dichloroimidazole-2-carboxamide; cyclohexyl, alkenyl or alkynyl with 3-6 carbon atoms; or phenyl or naphthyl, optionally substituted by $C_{1-4}$-alkoxy, $C_{1-4}$-halogenoalkyl, halogen, $C_{1-4}$-halogenoalkyl, halogen, $C_{1-4}$-alkoxy, $C_{1-4}$-halogenoalkoxy, acetyl, or phenoxy, naphthoxy, phenylmercapto or naphthylmercapto optionally substituted by halogen, $C_{1-4}$-alkyl, $CF_3$, $C_{1-4}$-alkoxy, $NO_2$ or $C_{1-4}$-alkylmercapto, or an acid addition salt thereof.

2. A 4,5-dichloro-imidazole-2-carboxylic acid amide according to claim 1,
wherein R' denotes $C_1$–$C_{12}$-alkyl, -alkenyl or -alkinyl, optionally substituted by halogen, $C_1$–$C_4$-alkoxy or cyano; or cycloalkyl with 5 or 6 carbon atoms in the ring, and
R'' denotes hydrogen, $C_1$–$C_4$-alkyl or -alkenyl or the formyl radical -CHO.

3. A 4,5-dichloro-imidazole-2-carboxylic acid amide accoring to claim 1, wherein R' is hydrogen and R'' is phenyl or naphthyl optionally substituted by halogen, $C_{1-4}$-alkyl, $CF_3$, $C_{1-4}$-alkoxy, $NO_2$ or $C_{1-4}$-alkylmercapto.

4. A 4,5-dichloro-imidazole-2-carboxylic acid amide according to claim 1, wherein such amide is 4,5-dichloro-imidazole-2-carboxylic-tert.-butylamide of the formula

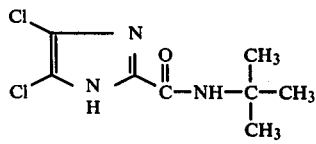

5. A 4,5-dichloro-imidazole-2-carboxylic acid amide according to claim 1, wherein such amide is a 4,5-dichloro-imidazole-2-carboxylic-N-formyl-isopropyl-amide of the formula

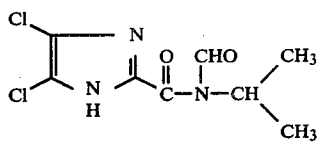

6. A 4,5-dichloro-imidazole-2-carboxylic acid amide according to claim 1, wherein such amide is 4,5-dichloro-imidazole-2-carboxylic-acid-(2-methyl-butin-(3)-yl-2-)-amide of the formula

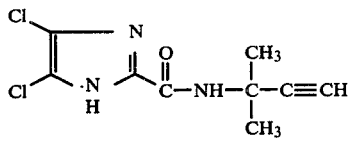

7. A 4,5-dichloroimidazole-2-carboxylic acid amide according to claim 1, wherein such amide is 4,5-dichloro-imidazole-2-carboxylic acid 2'-chloro-4'-trifluoromethylanilide of the formula

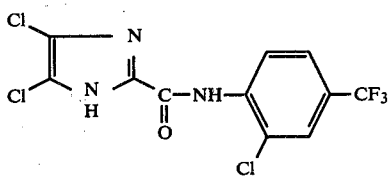

8. A nematicidal composition containing as active ingredient a nematicidally effective amount of a compound according to claim 1 in admixture with a diluent.

9. An arthropodicidal composition containing as active ingredient an arthropodicidally effective amount of a compound according to claim 1 in admixture with a diluent.

10. A fungicidal composition containing as active ingredient a fungidally effective amount of a compound according to claim 1 in admixture with a diluent.

11. A herbicidal composition containing as active ingredient a herbicidally effective amount of a compound according to claim 1 in admixture with a diluent.

12. A method of combating nematodes which comprises applying to the nematodes, or to a habitat thereof, a nematicidally effective amount of a compound according to claim 1.

13. A method of combating arthropods which comprises applying to the arthropods, or to a habitat thereof, an arthropodicidally effective amount of a compound according to claim 1.

14. A method of combating fungi which comprises applying to the fungi, or to a habitat thereof, a fungicidally effective amount of a compound according to claim 1.

15. A method of combating weeds which comprises applying to the weeds, or to a habitat thereof, a herbicidally effective amount of a compound according to claim 1.

16. The method according to claim 12 in which said compound is
4,5-dichloro-imidazole-2-carboxylic-tert.-butylamide,
4,5-dichloro-imidazole-2-carboxylic-N-formyl-isopropyl amide,
4,5-dichloro-imidazole-2-carboxylic-acid-(2-methyl-butin-(3)-yl-2) amide, or
4,5-dichloro-imidazole-2-carboxylic acid 2'-chloro-4'-trifluoromethyl-anilide.

17. A 4,5-dichloroimidazole-2-carboxylic acid amide of the formula

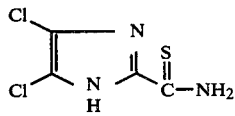

18. A nematicidal composition containing as active ingredient a nematidicidally effective amount of a compound according to claim 17 in admixture with a diluent.

19. An arthropodicidal composition containing as active ingredient an arthropodicidally effective amount of a compound according to claim 17 in admixture with a diluent.

20. A fungicidal composition containing as active ingredient a fungicidally effective amount of a compound according to claim 17 in admixture with a diluent.

21. A herbicidal composition containing as active ingredient a herbicidally effective amount of a compound according to claim 17 in admixture with a diluent.

22. A method of combating nematodes which comprises applying to the nematodes, or to a habitat thereof, a nematicidally effective amount of a compound according to claim 17.

23. A method of combating arthropods which comprises applying to the arthropods, or to a habitat thereof, an arthropodicidally effective amount of a compound according to claim 17.

24. A method of combating fungi which comprises applying to the fungi, or to a habitat thereof, a fungicidally effective amount of a compound according to claim 17.

25. A method of combating weeds which comprises applying to the weeds, or to a habitat thereof, a herbicidally effective amount of a compound according to claim 17.

* * * * *